(12) United States Patent
Chopra et al.

(10) Patent No.: US 11,963,520 B2
(45) Date of Patent: Apr. 23, 2024

(54) TRANSGENIC MOUSE EXPRESSING HUMAN CEREBLON

(71) Applicant: Celgene Corporation, Summit, NJ (US)

(72) Inventors: Rajesh Chopra, Sutton (GB); Anke Klippel, Westfield, NJ (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 16/070,769

(22) PCT Filed: Jan. 18, 2017

(86) PCT No.: PCT/US2017/013909
§ 371 (c)(1),
(2) Date: Jul. 17, 2018

(87) PCT Pub. No.: WO2017/127414
PCT Pub. Date: Jul. 27, 2017

(65) Prior Publication Data
US 2019/0037818 A1     Feb. 7, 2019

Related U.S. Application Data

(60) Provisional application No. 62/280,633, filed on Jan. 19, 2016.

(51) Int. Cl.
*A01K 67/027* (2006.01)
*A01K 67/0278* (2024.01)
*A61K 39/00* (2006.01)
*G01N 33/574* (2006.01)

(52) U.S. Cl.
CPC .. *A01K 67/0278* (2013.01); *A61K 39/001102* (2018.08); *G01N 33/57484* (2013.01); *A01K 2217/072* (2013.01); *A01K 2227/105* (2013.01); *A01K 2267/03* (2013.01); *A01K 2267/0331* (2013.01)

(58) Field of Classification Search
USPC ............................................ 800/18; 435/325
See application file for complete search history.

(56) References Cited

U.S. PATENT DOCUMENTS

| | | | |
|---|---|---|---|
| 7,504,554 B2* | 3/2009 | Liu ................... | A01K 67/0271 800/13 |
| 9,365,640 B2 | 6/2016 | Lopez-Girona et al. | |
| 9,587,281 B2* | 3/2017 | Thakurta .............. | C12Q 1/6886 |
| 9,611,465 B2 | 4/2017 | Handa et al. | |
| 10,047,151 B2 | 8/2018 | Lopez-Girona et al. | |
| 10,092,555 B2 | 10/2018 | Chamberlain et al. | |
| 10,272,117 B2 | 4/2019 | Handa et al. | |
| 10,668,057 B2 | 6/2020 | Chamberlain et al. | |
| 10,816,544 B2 | 10/2020 | Chamberlain et al. | |
| 11,419,861 B2 | 8/2022 | Chamberlain et al. | |
| 11,644,461 B2 | 5/2023 | Chamberlain et al. | |
| 2006/0179501 A1* | 8/2006 | Chan .................. | A01K 67/0275 800/18 |
| 2012/0134969 A1 | 5/2012 | Handa et al. | |
| 2015/0152511 A1* | 6/2015 | Thakurta .............. | C12Q 1/6886 514/235.2 |
| 2017/0362660 A1 | 12/2017 | Thakurta et al. | |
| 2018/0224435 A1 | 8/2018 | Chamberlain et al. | |
| 2019/0030019 A1 | 1/2019 | Chamberlain et al. | |
| 2021/0000813 A1 | 1/2021 | Chamberlain et al. | |
| 2021/0102938 A1 | 4/2021 | Chamberlain et al. | |

FOREIGN PATENT DOCUMENTS

| | | | |
|---|---|---|---|
| JP | 2004533826 A | 11/2004 | |
| JP | 2010514421 A | 5/2010 | |
| WO | WO 1998037757 A1 | 9/1998 | |
| WO | WO 2014028445 A2 | 2/2001 | |
| WO | WO 2002083897 A1 | 10/2002 | |
| WO | WO 2008080052 A1 | 7/2008 | |
| WO | WO 2014028445 A3 | 2/2014 | |
| WO | WO 2014123267 A1 | 8/2014 | |
| WO | WO 2015/077058 * | 5/2015 | |
| WO | WO 2015077058 A2 | 5/2015 | |
| WO | WO 2015077058 A3 | 5/2015 | |

OTHER PUBLICATIONS

Doyle (Transgenic Res., 2012, vol. 21, p. 327-349).*
Saito (Nature Neuroscience, May 2014, vol. 17, No. 5, p. 661-663).*
Garanto (PLoS, Nov. 2013, vol. 8, No. 11, e79369, p. 1-10).*
Manis (NEJM, 2007, vol. 357, p. 2426-2429).*
Song (Nature Cell Biol., 2007, vol. 9, No. 5, p. 573-580).*
Zhu (Nature Comm., 2019, vol. 10, No. 1845, p. 1-13).*
Albertelli (Mol. Endocrinology, 2006, vol. 20, No. 6, p. 1248-1260).*
Kitamoto (Biochemical and Biophysical Res. Comm., 1996, vol. 222, p. 742-747).*
Lute (Blood, 2005, vol. 106, No. 9, p. 3127-3133).*
Jacob (Hum. Genetics, 2017, vol. 136, p. 1043-1057).*
Batt (Nucleic Acids Res., 1994, vol. 22, p. 2811-2816).*
GenBank: BC067811.1; *Homo sapiens* cereblon, mRNA (cDNA clone MGC:87290 IMAGE:5264951), complete cds; Jul. 17, 2006 [retrieved on Apr. 2, 2017 from https://www.ncbi.nlm.nih.gov/nuccore/BC067811] nucleotides 15-1340, 98.7% identity to Seq ID No. 5.

(Continued)

*Primary Examiner* — Michael C Wilson
(74) *Attorney, Agent, or Firm* — JONES DAY

(57) ABSTRACT

Provided are transgenic mice whose genome comprises a nucleic acid sequence encoding human cereblon (CRBN) or a fragment thereof, wherein endogenous mouse CRBN is not expressed in the transgenic mice. Also provided are cells, cell lines, tissues, and organs derivable from the transgenic mice, and methods for producing and using such mice.

7 Claims, 20 Drawing Sheets

Specification includes a Sequence Listing.

(56) References Cited

OTHER PUBLICATIONS

Kim et al., 2014, "Ablation of cereblon attenuates myocardial ischemia-reperfusion injury," Biochem Biophys Res Commun., 447(4):649-654.
Manis, 2007, "Knock out, knock in, knock down—genetically manipulated mice and the Nobel Prize," N. Engl. J. Med., 357(24):2426-2429.
International Search Report and Written Opinion dated Jun. 30, 2017 of International Patent Application No. PCT/US2017/013909 (published as WO 2017127414) (11 pages).
Miura et al., 2018, "Easi-CRISPR for creating knock-in and conditional knockout mouse models using long ssDNA donors," Nat. Protoc., 13(1): 195-215 (Epub 2017).
Willyard, 2018, "New human gene tally reignites debate," Nature, 558(7710):354-355.

* cited by examiner

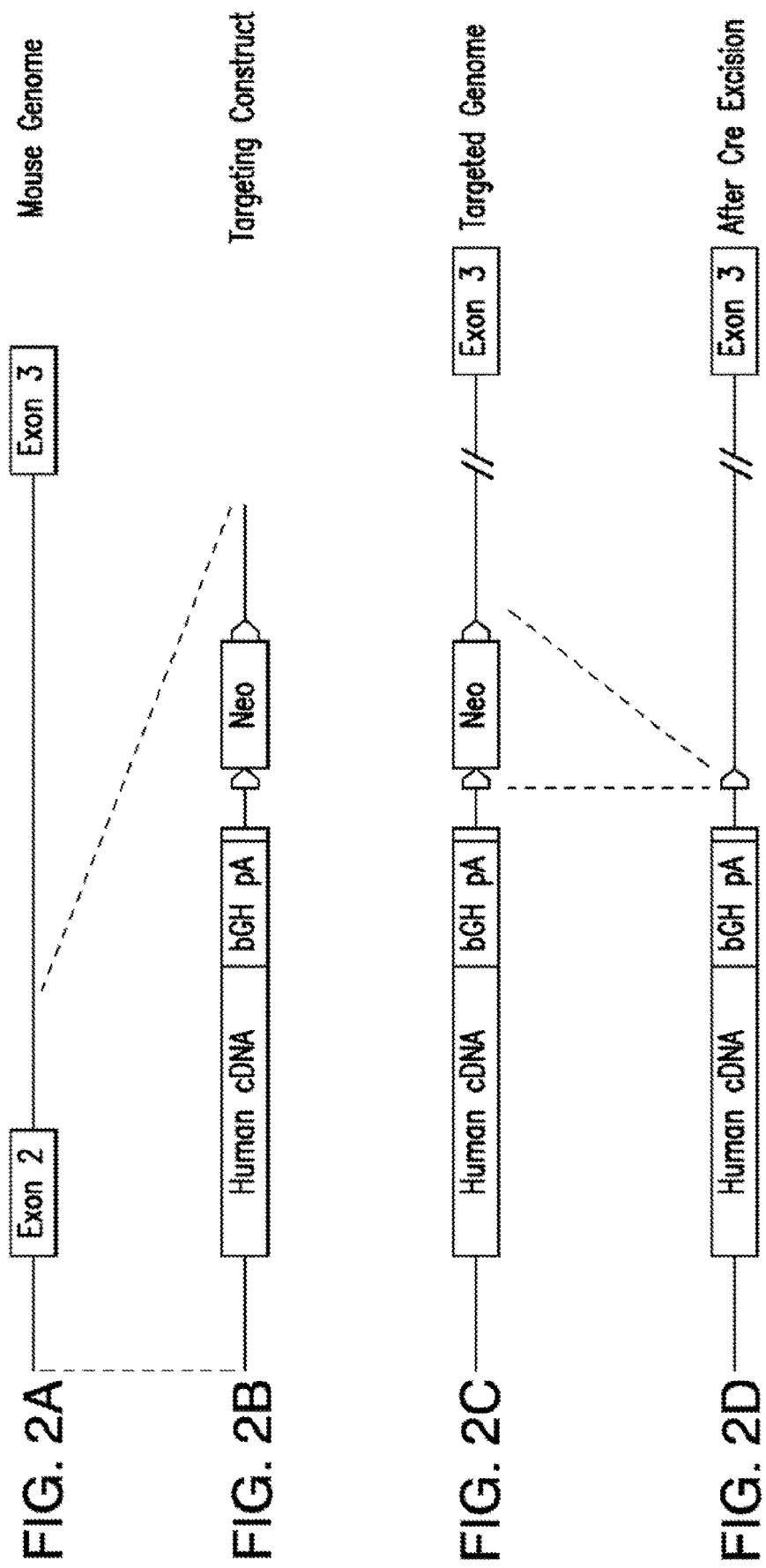

SEQUENCE LISTING

```
<160> NUMBER OF SEQ ID NOS: 17

<210> SEQ ID NO 1
<211> LENGTH: 442
<212> TYPE: PRT
<213> ORGANISM: Homo sapiens
<220> FEATURE:
<223> OTHER INFORMATION: amino acid sequence of human CRBN isoform 1

<400> SEQUENCE: 1

Met Ala Gly Glu Gly Asp Gln Gln Asp Ala Ala His Asn Met Gly Asn
1               5                   10                  15

His Leu Pro Leu Leu Pro Ala Glu Ser Glu Glu Glu Asp Glu Met Glu
            20                  25                  30

Val Glu Asp Gln Asp Ser Lys Glu Ala Lys Lys Pro Asn Ile Ile Asn
        35                  40                  45

Phe Asp Thr Ser Leu Pro Thr Ser His Thr Tyr Leu Gly Ala Asp Met
    50                  55                  60

Glu Glu Phe His Gly Arg Thr Leu His Asp Asp Asp Ser Cys Gln Val
65                  70                  75                  80

Ile Pro Val Leu Pro Gln Val Met Met Ile Leu Ile Pro Gly Gln Thr
                85                  90                  95

Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
    130                 135                 140
```

-continued

Arg Glu Glu Gln Asp Phe Gly Ile Glu Ile Val Lys Val Lys Ala Ile
145                 150                 155                 160

Gly Arg Gln Arg Phe Lys Val Leu Glu Leu Arg Thr Gln Ser Asp Gly
            165                 170                 175

Ile Gln Gln Ala Lys Val Gln Ile Leu Pro Glu Cys Val Leu Pro Ser
        180                 185                 190

Thr Met Ser Ala Val Gln Leu Glu Ser Leu Asn Lys Cys Gln Ile Phe
    195                 200                 205

Pro Ser Lys Pro Val Ser Arg Glu Asp Gln Cys Ser Tyr Lys Trp Trp
210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
            245                 250                 255

Ile Lys Lys Gln Leu Arg Glu Trp Asp Glu Asn Leu Lys Asp Asp Ser
        260                 265                 270

Leu Pro Ser Asn Pro Ile Asp Phe Ser Tyr Arg Val Ala Ala Cys Leu
    275                 280                 285

Pro Ile Asp Asp Val Leu Arg Ile Gln Leu Leu Lys Ile Gly Ser Ala
290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
            325                 330                 335

Ile Phe Ser Leu Ser Leu Cys Gly Pro Met Ala Ala Tyr Val Asn Pro
        340                 345                 350

His Gly Tyr Val His Glu Thr Leu Thr Val Tyr Lys Ala Cys Asn Leu
    355                 360                 365

Asn Leu Ile Gly Arg Pro Ser Thr Glu His Ser Trp Phe Pro Gly Tyr
370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
            405                 410                 415

Leu Thr Arg Ser Ala Leu Leu Pro Thr Ile Pro Asp Thr Glu Asp Glu
        420                 425                 430

Ile Ser Pro Asp Lys Val Ile Leu Cys Leu
    435                 440

<210> SEQ ID NO 2
<211> LENGTH: 441
<212> TYPE: PRT
<213> ORGANISM: homo sapiens
<220> FEATURE:
<223> OTHER INFORMATION: amino acid sequence of human CRBN isoform 2

<400> SEQUENCE: 2

Met Ala Gly Glu Gly Asp Gln Gln Asp Ala Ala His Asn Met Gly Asn
1               5                   10                  15

His Leu Pro Leu Leu Pro Glu Ser Glu Glu Glu Asp Glu Met Glu Val
            20                  25                  30

Glu Asp Gln Asp Ser Lys Glu Ala Lys Lys Pro Asn Ile Ile Asn Phe
        35                  40                  45

Asp Thr Ser Leu Pro Thr Ser His Thr Tyr Leu Gly Ala Asp Met Glu
    50                  55                  60

-continued

Glu Phe His Gly Arg Thr Leu His Asp Asp Ser Cys Gln Val Ile
65                  70                  75                  80

Pro Val Leu Pro Gln Val Met Met Ile Leu Ile Pro Gly Gln Thr Leu
            85                  90                  95

Pro Leu Gln Leu Phe His Pro Gln Glu Val Ser Met Val Arg Asn Leu
                100                 105                 110

Ile Gln Lys Asp Arg Thr Phe Ala Val Leu Ala Tyr Ser Asn Val Gln
        115                 120                 125

Glu Arg Glu Ala Gln Phe Gly Thr Thr Ala Glu Ile Tyr Ala Tyr Arg
    130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
        180                 185                 190

Met Ser Ala Val Gln Leu Glu Ser Leu Asn Lys Cys Gln Ile Phe Pro
    195                 200                 205

Ser Lys Pro Val Ser Arg Glu Asp Gln Cys Ser Tyr Lys Trp Trp Gln
210                 215                 220

Lys Tyr Gln Lys Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
                245                 250                 255

Lys Lys Gln Leu Arg Glu Trp Asp Glu Asn Leu Lys Asp Asp Ser Leu
        260                 265                 270

Pro Ser Asn Pro Ile Asp Phe Ser Tyr Arg Val Ala Ala Cys Leu Pro
    275                 280                 285

Ile Asp Asp Val Leu Arg Ile Gln Leu Leu Lys Ile Gly Ser Ala Ile
290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
                325                 330                 335

Phe Ser Leu Ser Leu Cys Gly Pro Met Ala Ala Tyr Val Asn Pro His
        340                 345                 350

Gly Tyr Val His Glu Thr Leu Thr Val Tyr Lys Ala Cys Asn Leu Asn
    355                 360                 365

Leu Ile Gly Arg Pro Ser Thr Glu His Ser Trp Phe Pro Gly Tyr Ala
370                 375                 380

Trp Thr Val Ala Gln Cys Lys Ile Cys Ala Ser His Ile Gly Trp Lys
                385                 390                 395                 400

Phe Thr Ala Thr Lys Lys Asp Met Ser Pro Gln Lys Phe Trp Gly Leu
        405                 410                 415

Thr Arg Ser Ala Leu Leu Pro Thr Ile Pro Asp Thr Glu Asp Glu Ile
    420                 425                 430

Ser Pro Asp Lys Val Ile Leu Cys Leu
435                 440

<210> SEQ ID NO 3
<211> LENGTH: 444
<212> TYPE: PRT
<213> ORGANISM: mouse
<220> FEATURE:
<223> OTHER INFORMATION: amino acid sequence of mouse CRBN isoform 1

<400> SEQUENCE: 3

```
Met Ala Gly Glu Gly Asp Gln Gln Asp Ala Ala His Asn Met Gly Asn
1               5                   10                  15

His Leu Pro Leu Leu Pro Asp Ser Glu Asp Glu Asp Glu Ile Glu
            20                  25                  30

Met Glu Val Glu Asp Gln Asp Ser Lys Glu Ala Arg Lys Pro Asn Ile
        35                  40                  45

Ile Asn Phe Asp Thr Ser Leu Pro Thr Ser His Thr Tyr Leu Gly Ala
    50                  55                  60

Asp Met Glu Glu Phe His Gly Arg Thr Leu His Asp Asp Ser Cys
65                  70                  75                  80

Gln Val Ile Pro Val Leu Pro Glu Val Leu Met Ile Leu Ile Pro Gly
                85                  90                  95

Gln Thr Leu Pro Leu Gln Leu Ser His Pro Gln Glu Val Ser Met Val
            100                 105                 110

Arg Asn Leu Ile Gln Lys Asp Arg Thr Phe Ala Val Leu Ala Tyr Ser
        115                 120                 125

Asn Val Gln Glu Arg Glu Ala Gln Phe Gly Thr Thr Ala Glu Ile Tyr
    130                 135                 140

Ala Tyr Arg Glu Glu Gln Glu Phe Gly Ile Glu Val Val Lys Val Lys
145                 150                 155                 160

Ala Ile Gly Arg Gln Arg Phe Lys Val Leu Glu Leu Arg Thr Gln Ser
                165                 170                 175

Asp Gly Ile Gln Gln Ala Lys Val Gln Ile Leu Pro Glu Cys Val Leu
            180                 185                 190

Pro Ser Thr Met Ser Ala Val Gln Leu Glu Ser Leu Asn Lys Cys Gln
        195                 200                 205

Val Phe Pro Ser Lys Pro Ile Ser Trp Glu Asp Gln Tyr Ser Cys Lys
    210                 215                 220

Trp Trp Gln Lys Tyr Gln Lys Arg Lys Phe His Cys Ala Asn Leu Thr
225                 230                 235                 240

Ser Trp Pro Arg Trp Leu Tyr Ser Leu Tyr Asp Ala Glu Thr Leu Met
                245                 250                 255

Asp Arg Ile Lys Lys Gln Leu Arg Glu Trp Asp Glu Asn Leu Lys Asp
            260                 265                 270

Asp Ser Leu Pro Glu Asn Pro Ile Asp Phe Ser Tyr Arg Val Ala Ala
        275                 280                 285

Cys Leu Pro Ile Asp Asp Val Leu Arg Ile Gln Leu Leu Lys Ile Gly
    290                 295                 300

Ser Ala Ile Gln Arg Leu Arg Cys Glu Leu Asp Ile Met Asn Lys Cys
305                 310                 315                 320

Thr Ser Leu Cys Cys Lys Gln Cys Gln Glu Thr Glu Ile Thr Thr Lys
                325                 330                 335

Asn Glu Ile Phe Ser Leu Ser Cys Gly Pro Met Ala Ala Tyr Val
            340                 345                 350

Asn Pro His Gly Tyr Val His Glu Thr Leu Thr Val Tyr Lys Ala Ser
        355                 360                 365

Asn Leu Asn Leu Ile Gly Arg Pro Ser Thr Val His Ser Trp Phe Pro
    370                 375                 380

Gly Tyr Ala Trp Thr Ile Ala Gln Cys Lys Ile Cys Ala Ser His Ile
385                 390                 395                 400

Gly Trp Lys Phe Thr Ala Thr Lys Lys Asp Met Ser Pro Gln Lys Phe
```

```
                    405                 410                 415
Trp Gly Leu Thr Arg Ser Ala Leu Leu Pro Thr Ile Pro Glu Thr Glu
                420                 425                 430

Asp Glu Ile Ser Pro Asp Lys Val Ile Leu Cys Leu
            435                 440

<210> SEQ ID NO 4
<211> LENGTH: 445
<212> TYPE: PRT
<213> ORGANISM: mouse
<220> FEATURE:
<223> OTHER INFORMATION: amino acid sequence of mouse CRBN isoform 2

<400> SEQUENCE: 4

Met Ala Gly Glu Gly Asp Gln Gln Asp Ala Ala His Asn Met Gly Asn
1               5                   10                  15

His Leu Pro Leu Leu Pro Ala Asp Ser Glu Asp Glu Asp Asp Glu Ile
            20                  25                  30

Glu Met Glu Val Glu Asp Gln Asp Ser Lys Glu Ala Arg Lys Pro Asn
        35                  40                  45

Ile Ile Asn Phe Asp Thr Ser Leu Pro Thr Ser His Thr Tyr Leu Gly
    50                  55                  60

Ala Asp Met Glu Glu Phe His Gly Arg Thr Leu His Asp Asp Asp Ser
65              70                  75                  80

Cys Gln Val Ile Pro Val Leu Pro Glu Val Leu Met Ile Leu Ile Pro
                85                  90                  95

Gly Gln Thr Leu Pro Leu Gln Leu Ser His Pro Gln Glu Val Ser Met
            100                 105                 110

Val Arg Asn Leu Ile Gln Lys Asp Arg Thr Phe Ala Val Leu Ala Tyr
        115                 120                 125

Ser Asn Val Gln Glu Arg Glu Ala Gln Phe Gly Thr Thr Ala Glu Ile
    130                 135                 140

Tyr Ala Tyr Arg Glu Glu Gln Glu Phe Gly Ile Glu Val Val Lys Val
145                 150                 155                 160

Lys Ala Ile Gly Arg Gln Arg Phe Lys Val Leu Glu Leu Arg Thr Gln
                165                 170                 175

Ser Asp Gly Ile Gln Gln Ala Lys Val Gln Ile Leu Pro Glu Cys Val
            180                 185                 190

Leu Pro Ser Thr Met Ser Ala Val Gln Leu Glu Ser Leu Asn Lys Cys
        195                 200                 205

Gln Val Phe Pro Ser Lys Pro Ile Ser Trp Glu Asp Gln Tyr Ser Cys
    210                 215                 220

Lys Trp Trp Gln Lys Tyr Gln Lys Arg Lys Phe His Cys Ala Asn Leu
225                 230                 235                 240

Thr Ser Trp Pro Arg Trp Leu Tyr Ser Leu Tyr Asp Ala Glu Thr Leu
                245                 250                 255

Met Asp Arg Ile Lys Lys Gln Leu Arg Glu Trp Asp Glu Asn Leu Lys
            260                 265                 270

Asp Asp Ser Leu Pro Glu Asn Pro Ile Asp Phe Ser Tyr Arg Val Ala
        275                 280                 285

Ala Cys Leu Pro Ile Asp Asp Val Leu Arg Ile Gln Leu Leu Lys Ile
    290                 295                 300

Gly Ser Ala Ile Gln Arg Leu Arg Cys Glu Leu Asp Ile Met Asn Lys
305                 310                 315                 320

Cys Thr Ser Leu Cys Cys Lys Gln Cys Gln Glu Thr Glu Ile Thr Thr
```

```
                    325                 330                 335
Lys Asn Glu Ile Phe Ser Leu Ser Leu Cys Gly Pro Met Ala Ala Tyr
                340                 345                 350

Val Asn Pro His Gly Tyr Val His Glu Thr Leu Thr Val Tyr Lys Ala
                355                 360                 365

Ser Asn Leu Asn Leu Ile Gly Arg Pro Ser Thr Val His Ser Trp Phe
            370                 375                 380

Pro Gly Tyr Ala Trp Thr Ile Ala Gln Cys Lys Ile Cys Ala Ser His
385                 390                 395                 400

Ile Gly Trp Lys Phe Thr Ala Thr Lys Lys Asp Met Ser Pro Gln Lys
                405                 410                 415

Phe Trp Gly Leu Thr Arg Ser Ala Leu Leu Pro Thr Ile Pro Glu Thr
                420                 425                 430

Glu Asp Glu Ile Ser Pro Asp Lys Val Ile Leu Cys Leu
                435                 440                 445

<210> SEQ ID NO 5
<211> LENGTH: 1329
<212> TYPE: DNA
<213> ORGANISM: Homo sapiens
<220> FEATURE:
<223> OTHER INFORMATION: cDNA sequence encoding human CRBN isoform 1

<400> SEQUENCE: 5
atggccggcg aaggagatca gcaggacgct gcgcacaaca tgggcaacca cctgccgctc      60
ctgcctgcag agagtgagga agaagatgaa atggaagttg aagaccagga tagtaaagaa     120
gccaaaaaac caaacatcat aaattttgac accagtctgc cgacatcaca tacatacata     180
ggtgctgata tggaagaatt tcatggcagg actttgcacg atgacgacag ctgtcaggtg     240
attccagttc ttccacaagt gatgatgatc ctgattcccg gacagacatt acctcttcag     300
ctttttcacc ctcaagaagt cagtatggtg cggaatttaa ttcagaaaga tagaaccttt     360
gctgttcttg catacagcaa tgtacaggaa agggaagcac agtttggaac aacagcagag     420
atatatgcct atcgagaaga acaggatttt ggaattgaga tagtgaaagt gaaagcaatt     480
ggaagacaaa ggttcaaagt ccttgagcta agaacacagt cagatggaat ccagcaagct     540
aaagtgcaaa ttcttcccga atgtgtgttg ccttcaacca tgtctgcagt tcaattagaa     600
tccctcaata agtgccagat atttccttca aaacctgtct caagaagaa ccaatgttca     660 tataaatggt ggcagaaata ccagaagaga agtttcatt gtgcaaatct aacttcatgg     720
cctcgctggc tgtattcctt atatgatgct gagaccttaa tggacagaat caagaaacag     780
ctacgtgaat gggatgaaaa tctaaaagat gattctcttc cttcaaatcc aatagatttt     840
tcttacagag tagctgcttg tcttcctatt gatgatgtat tgagaattca gctccttaaa     900
attggcagtg ctatccagcg acttcgctgt gaattagaca ttatgaataa atgtacttcc     960
ctttgctgta acaatgtcag aaaacagaa ataacaacca aaatgaaat attcagttta    1020 tccttatgtg ggccgatggc agcttatgtg aatcctcatg gatatgtgca tgagacactt    1080
actgtgtata aggcttgcaa cttgaatctg ataggccggc cttctacaga acacagctgg    1140
tttcctgggt atgcctggac tgttgcccag tgtaagatct gtgcaagcca tattggatgg    1200
aagtttacgg ccaccaaaaa agacatgtca cctcaaaaat tttggggctt aacgcgatct    1260
gctctgttgc ccacgatccc agacactgaa gatgaaataa gtccagacaa agtaatactt    1320
tgcttgtaa                                                            1329
```

<210> SEQ ID NO 6
<211> LENGTH: 1326
<212> TYPE: DNA
<213> ORGANISM: Homo sapiens
<220> FEATURE:
<223> OTHER INFORMATION: cDNA sequence encoding human CRBN isoform 2

<400> SEQUENCE: 6

| | |
|---|---|
| atggccggcg aaggagatca gcaggacgct gcgcacaaca tgggcaacca cctgccgctc | 60 |
| ctgcctgaga gtgaggaaga agatgaaatg gaagttgaag accaggatag taaagaagcc | 120 |
| aaaaaaccaa acatcataaa ttttgacacc agtctgccga catcacatac atacctaggt | 180 |
| gctgatatgg aagaatttca tggcaggact ttgcacgatg acgacagctg tcaggtgatt | 240 |
| ccagttcttc cacaagtgat gatgatcctg attcccggac agacattacc tcttcagctt | 300 |
| tttcaccctc aagaagtcag tatggtgcgg aatttaattc agaaagatag aacctttgct | 360 |
| gttcttgcat acagcaatgt acaggaaagg aagcacagtt tggaacaac agcagagata | 420 |
| tatgcctatc gagaagaaca ggattttgga attgagatag tgaaagtgaa agcaattgga | 480 |
| agacaaaggt tcaaagtcct tgagctaaga cacagtcag atggaatcca gcaagctaaa | 540 |
| gtgcaaattc ttcccgaatg tgtgttgcct tcaaccatgt ctgcagttca attagaatcc | 600 |
| ctcaataagt gccagatatt tccttcaaaa cctgtctcaa gagaagacca atgttcatat | 660 |
| aaatggtggc agaaatacca agagagaaag tttcattgtg caaatctaac ttcatggcct | 720 |
| cgctggctgt attccttata tgatgctgag accttaatgg acagaatcaa gaaacagcta | 780 |
| cgtgaatggg atgaaaatct aaaagatgat tctcttcctt caaatccaat agatttttct | 840 |
| tacagagtag ctgcttgtct tcctattgat gatgtattga gaattcagct ccttaaaatt | 900 |
| ggcagtgcta tccagcgact tcgctgtgaa ttagacatta tgaataaatg tacttccctt | 960 |
| tgctgtaaac aatgtcaaga aacagaaata caaccaaaa atgaaatatt cagtttatcc | 1020 |
| ttatgtgggc cgatggcagc ttatgtgaat cctcatggat atgtgcatga gacacttact | 1080 |
| gtgtataagg cttgcaactt gaatctgata ggccggcctt ctacagaaca cagctggttt | 1140 |
| cctgggtatg cctggactgt tgcccagtgt aagatctgtg caagccatat ggatggaag | 1200 |
| tttacggcca ccaaaaaaga catgtcacct caaaaatttt ggggcttaac gcgatctgct | 1260 |
| ctgttgccca cgatcccaga cactgaagat gaaataagtc cagacaaagt aatactttgc | 1320 |
| ttgtaa | 1326 |

<210> SEQ ID NO 7
<211> LENGTH: 1261
<212> TYPE: DNA
<213> ORGANISM: Artificial Sequence
<220> FEATURE:
<223> OTHER INFORMATION: cDNA sequence encoding a fragment from Glu24 to
      the stop codon of human CRBN isoform 1 or a fragment from Glu23 to
      the stop codon of human CRBN isoform 2

<400> SEQUENCE: 7

| | |
|---|---|
| agagagtgag gaagaagatg aaatggaagt tgaagaccag gatagtaaag aagccaaaaa | 60 |
| accaaacatc ataaattttg acaccagtct gccgacatca catacatacc taggtgctga | 120 |
| tatggaagaa tttcatggca ggactttgca cgatgacgac agctgtcagg tgattccagt | 180 |
| tcttccacaa gtgatgatga tcctgattcc cggacagaca ttacctcttc agcttttca | 240 |
| ccctcaagaa gtcagtatgg tgcggaattt aattcagaaa gatagaacct ttgctgttct | 300 |
| tgcatacagc aatgtacagg aaagggaagc acagtttgga acaacagcag agatatatgc | 360 |

```
ctatcgagaa gaacaggatt ttggaattga gatagtgaaa gtgaaagcaa ttggaagaca      420
aaggttcaaa gtccttgagc taagaacaca gtcagatgga atccagcaag ctaaagtgca      480
aattcttccc gaatgtgtgt tgccttcaac catgtctgca gttcaattag aatccctcaa      540
taagtgccag atatttcctt caaaacctgt ctcaagagaa gaccaatgtt catataaatg      600
gtggcagaaa taccagaaga gaaagtttca ttgtgcaaat ctaacttcat ggcctcgctg      660
gctgtattcc ttatatgatg ctgagacctt aatggacaga atcaagaaac agctacgtga      720
atgggatgaa aatctaaaag atgattctct tccttcaaat ccaatagatt tttcttacag      780
agtagctgct tgtcttccta ttgatgatgt attgagaatt cagctcctta aaattggcag      840
tgctatccag cgacttcgct gtgaattaga cattatgaat aaatgtactt ccctttgctg      900
taaacaatgt caagaaacag aaataacaac caaaaatgaa atattcagtt tatccttatg      960
tgggccgatg gcagcttatg tgaatcctca tggatatgtg catgagacac ttactgtgta     1020
taaggcttgc aacttgaatc tgataggccg gccttctaca gaacacagct ggtttcctgg     1080
gtatgcctgg actgttgccc agtgtaagat ctgtgcaagc catattggat ggaagtttac     1140
ggccaccaaa aaagacatgt cacctcaaaa attttgggc ttaacgcgat ctgctctgtt      1200
gcccacgatc ccagacactg aagatgaaat aagtccagac aaagtaatac tttgcttgta     1260
a                                                                     1261
```

<210> SEQ ID NO 8
<211> LENGTH: 6282
<212> TYPE: DNA
<213> ORGANISM: Artificial Sequence
<220> FEATURE:
<223> OTHER INFORMATION: nucleic acid sequence of targeting construct

<400> SEQUENCE: 8

```
aagaacagct cacacttgat agaataccac ttctagaaag tagcgttgtg ttttgtttct       60
tcagactttc atctctgccc ttggcagcat catgttatca ggtggatcag cttagctttc      120
atttcatttc aaaaaaaaaa gtgcaggtag agttcttaag atatctcctt ttgccaggca      180
gtggtggcgc actcctttaa tcccagcact gggaggcag aggcaggcag atttctgagt       240
tcgaggccag cctggtctac agagtgagtt ccaggacagc cagggctaca tagagaaacc      300
ctgtctccaa aaactcgaaa aacagaaaag aaagaaaaa aaaaaagac atctccttta       360 aaatgtattt tctttgggcc aactttattt ttaaattgag aatgacaaag cgatgtttta      420
tgaaaaataa ttgcaaacat ttcacgttta aatatgacgg tgagccaggt tttaatggta      480
ttttttttcc cagtttcatt aacagacctt tcttgcctgc ttgtgttttc cttgctttct      540
ttttcacaga gaaactttgt agctaaagtc tgaagaacc tcatagatta ctttgttcaa       600
gccttcattg ttttttttt caaatgaaaa aacagcttta atcaattgga attcattgtg       660
taaggtgtca ggattagtag tgatggagaa gataagactc atccatgcag gagatggcc      720 taattcagcc acgtcagtcg ttaggctgga cctagtgatc tgcttttccaa ccgtgtacgg     780 tgtaactgcg gggcaggggc gagggggttt acagagaagg aagctggcgg ctgtttctga      840
ccagaaatca aggggaacat cagccctgg gtcaggctga ctgtacgtac ccttgatgtg       900
cggtgaggaa taggcgttgt ccctagcaga actctaatag agaatgacat ctattcccta      960
ttgagggatg ctgtgtaaag tcctgataag gaagacagaa catccagcat gcgtgtacca     1020
caggcagcaa aggagccata cctaaatata gcatggtgtc ctggaggggt aacaggaaat     1080
```

-continued

```
ggagaatagc tgaaaatcaa aggcaatcca aataagataa ggcatttagt taacagtaat   1140
gtgccaatat cgacgactta gttgtcacaa gaataccaga tgcatggacc atgctaacaa   1200
tggaggaaga tagtcttggc atgctagaat tctattttc caacattcca ggaaatctta    1260
aagtgtccta agatagttga ttgttaaaaa cagggaaaaa agaaaggaaa ggaaaagaaa   1320
ggaaaaggcg ccatgacaga aagagcacag acccagcctc tgccgctgtc tctgcacagc   1380
tttcctttta agagtgtctt tcttcaattc agggtgtgtg aatggaacca gaactgactt   1440
gctttttct tttcttttt ttttttta atgaatctca tttttccct ctattattct         1500
ccttcagcag agagtgagga agaagatgaa atggaagttg aagaccagga tagtaaagaa   1560
gccaaaaaac caaacatcat aaattttgac accagtctgc cgacatcaca tacataccta   1620
ggtgctgata tggaagaatt tcatggcagg actttgcacg atgacgacag ctgtcaggtg   1680
attccagttc ttccacaagt gatgatgatc ctgattcccg acagacatt acctcttcag    1740
cttttttcacc ctcaagaagt cagtatggtg cggaatttaa ttcagaaaga tagaaccttt  1800
gctgttcttg catacagcaa tgtacaggaa agggaagcac agtttggaac aacagcagag   1860
atatatgcct atcgagaaga acaggatttt ggaattgaga tagtgaaagt gaaagcaatt   1920
ggaagacaaa ggttcaaagt ccttgagcta agaacacagt cagatggaat ccagcaagct   1980
aaagtgcaaa ttcttcccga atgtgtgttg ccttcaacca tgtctgcagt tcaattagaa   2040
tccctcaata agtgccagat atttccttca aaacctgtct caagagaaga ccaatgttca   2100
tataaatggt ggcagaaata ccagaagaga aagtttcatt gtgcaaatct aacttcatgg   2160
cctcgctggc tgtattcctt atatgatgct gagaccttaa tggacagaat caagaaacag   2220
ctacgtgaat gggatgaaaa tctaaaagat gattctcttc cttcaaatcc aatagatttt   2280
tcttacagag tagctgcttg tcttcctatt gatgatgtat tgagaattca gctccttaaa   2340
attggcagtg ctatccagcg acttcgctgt gaattagaca ttatgaataa atgtacttcc   2400
ctttgctgta aacaatgtca agaaacagaa ataacaacca aaaatgaaat attcagttta   2460
tccttatgtg ggccgatggc agcttatgtg aatcctcatg gatatgtgca tgagacactt   2520
actgtgtata aggcttgcaa cttgaatctg ataggccggc cttctacaga acacagctgg   2580
tttcctgggt atgcctggac tgttgcccag tgtaagatct gtgcaagcca tattggatgg   2640
aagtttacgg ccaccaaaaa agacatgtca cctcaaaaat tttggggctt aacgcgatct   2700
gctctgttgc ccacgatccc agacactgaa gatgaaataa gtccagacaa agtaatactt   2760
tgcttgtaag tgcacctaga gctcgctgat cagcctcgac tgtgccttct agttgccagc   2820
catctgttgt ttgcccctcc cccgtgcctt ccttgaccct ggaaggtgcc actcccactg   2880
tcctttccta ataaaatgag gaaattgcat cgcattgtct gagtaggtgt cattctattc   2940
tgggggtgg ggtgggcag acagcaagg gggaggattg gaagacaat agcaggcatg       3000
ctggggatgc ggtgggctct atggcttctg aggcggaaag aaccagctgg gctcgacta    3060
gagcttgcgg aacccttcgt atgtggttta gtcattgagc aaatgcagta tgcggacctt   3120
tatctatggc tggaatttgg tacctttgc tagcataact tcgtatagca tacattatac    3180
gaagttatcc taggtaattc taccgggtag gggaggcgct tttcccaagg cagtctggag   3240
catgcgcttt agcagccccg ctgggcactt ggcgctacac aagtggcctc tggcctcgca   3300
cacattccac atccaccggt aggcgccaac cggctccgtt ctttggtggc ccttcgcgc    3360
cacttctac tcctcccta gtcaggaagt tcccccgc cccgcagctc gcgtcgtgca       3420
ggacgtgaca aatggaagta gcacgtctca ctagtctcgt gcagatggac agcaccgctg   3480
```

```
agcaatggaa gcgggtaggc ctttggggca gcggccaata gcagctttgc tccttcgctt    3540
tctgggctca gaggctggga aggggtgggt ccggggggcgg gctcagggggc gggctcaggg   3600
gcggggcggg cgcccgaagg tcctccggag gcccggcatt ctgcacgctt caaaagcgca    3660
cgtctgccgc gctgttctcc tcttcctcat ctccggggcct ttcgacctgc agcctgttga   3720
caattaatca tcggcatagt atatcggcat agtataatac gacaaggtga ggaactaaac    3780
cagatctgcc accatgattg aacaagatgg attgcacgca ggttctccgg ccgcttgggt    3840
ggagaggcta ttcggctatg actgggcaca acagacaatc ggctgctctg atgccgccgt    3900
gttccggctg tcagcgcagg ggcgcccggt tctttttgtc aagaccgacc tgtccggtgc    3960
cctgaatgaa ctgcaggacg aggcagcgcg gctatcgtgg ctggccacga cgggcgttcc    4020
ttgcgcagct gtgctcgacg ttgtcactga agcgggaagg gactggctgc tattgggcga    4080
agtgccgggg caggatctcc tgtcatctca ccttgctcct gccgagaaag tatccatcat    4140
ggctgatgca atgcggcggc tgcatacgct tgatccggct acctgcccat tcgaccacca    4200
agcgaaacat cgcatcgagc gagcacgtac tcggatggaa gccggtcttg tcgatcagga    4260
tgatctggac gaagagcatc agggggctcgc gccagccgaa ctgttcgcca ggctcaaggc    4320
gcgcatgccc gacggcgagg atctcgtcgt gacccatggc gatgcctgct tgccgaatat    4380
catggtggaa aatggccgct tttctggatt catcgactgt ggccggctgg gtgtggcgga    4440
ccgctatcag gacatagcgt tggctacccg tgatattgct gaagagcttg gcggcgaatg    4500
ggctgaccgc ttcctcgtgc tttacggtat cgccgctccc gattcgcagc gcatcgcctt    4560
ctatcgcctt cttgacgagt tcttctgact taagaacttg tttattgcag cttataatgg    4620
ttacaaataa agcaatagca tcacaaattt cacaaataaa gcatttttt cactgcattc     4680
tagttgtggt ttgtccaaac tcatcaatgt atcttatcat gtctgcaatt gataacttcg    4740
tatagcatac attatacgaa gttatgaatt cttttctcga gcctaagtgc agggagccac    4800
actaggggac tagtgcaggg gactgactag agggttcctg catattcgct gaccctagaa    4860
tccgtgcatg agaacagact tattttccag tgcatagcat gtaattttag aaatggaagc    4920
cgtgtcgtac tatatcctca tgtgattctt gactattttc taatatgtaa gctgatatgt    4980
aaacattaaa gctaacatat agctttatgt ttaaacttat cttgggaggg actctttgag    5040
gaattgtctt cctctgaagg gttctgctag taactgagcc attaagtgtt cttaatgttg    5100
tttcagaact gctgggatgt ggggcggtat tataggtact aaaattctgt cctatgcttt    5160
gtcagttttg gacatagagg agtttggtg aaaatatttt gaattacaaa ataatgatcg    5220
attcttgata aaaattggga gttctaatag gaaatactag atcaaaaatt agagtttgat    5280
ggaggcatgc ttatataaca gattatttaa ataaacatgt gctctgttta gtgttttcct    5340
ctgctttatt ctttagtagg ttgacgtgta gtaagtgtgt gtcttgactc tgtgctcttg    5400
agtagtacct gggagctgat atggaggagt tccacgggag aactttgcat gacgacgaca    5460
gctgccaggt gatcccagtc cttcctgagg tgctgatgat cctgattcct gggcagacac    5520
tcccactgca gctctctcac ccacaggaag tcagcatggt gcggaactta atccagaaag    5580
acaggaccatt tgcagtcctt gcatacaggt aagagattag acagatctgc ttaccaccct    5640
gccaaagtca gtgcgacagc taaagccaac ggggatttgc agatactgga caggagtgtg    5700
aagcaaacgg tcttgtgtca catttcagt gtttcgctgt ttttacagtg tagctgtgtt    5760
tggctcttga aaaacttcca ctcacttaat ggaaaacctc cctgttcaga actgtcttta    5820
```

```
tttaaaaata gctaagtttt aaaattttca ataaaggtta cttttctaaa gtgaagctgt    5880
tcttcagtag cctgtggcaa atgagggaac cgtggtggag gcaggaaatg gaaacaggaa    5940
acctcccatc accccgctg accctccct cagacagtca cagtgctgcc agttagtgcg      6000
accatcattg cctgccaaag tgaaggatg ctcattttgt gaaataacga tttaaaactt     6060
cttagcactg gttatctcag tgaagcctaa aagtctacct ttattctaaa atatgctgtt    6120
tgccttccgg ggccttgtgt gtcagcttcc tagtgagggt tagctgctgt aattgtcaca    6180
gtgtttgccc gatctgtgtc gcttttgcca cctttacata attatgagcc agagctgaaa    6240
actctgtcca tttttgtctt tgaagtaatg tgcaagaaag gg                       6282

<210> SEQ ID NO 9
<211> LENGTH: 50
<212> TYPE: DNA
<213> ORGANISM: Artificial Sequence
<220> FEATURE:
<223> OTHER INFORMATION: TALEN 1 targeting sequence

<400> SEQUENCE: 9
tatgcggacc tttatctatg gctggaattt cctaagtgca gggagccaca              50

<210> SEQ ID NO 10
<211> LENGTH: 49
<212> TYPE: DNA
<213> ORGANISM: Artificial Sequence
<220> FEATURE:
<223> OTHER INFORMATION: TALEN 2 targeting sequence

<400> SEQUENCE: 10
tgcagtatgc ggacctttat ctatggctgg aatttcctaa gtgcaggga                49

<210> SEQ ID NO 11
<211> LENGTH: 48
<212> TYPE: DNA
<213> ORGANISM: Artificial Sequence
<220> FEATURE:
<223> OTHER INFORMATION: TALEN 3 targeting sequence

<400> SEQUENCE: 11
tctgccaacc tcacatacag tatgtggttt agtcattgag caaatgca                 48

<210> SEQ ID NO 12
<211> LENGTH: 20
<212> TYPE: DNA
<213> ORGANISM: Artificial Sequence
<220> FEATURE:
<223> OTHER INFORMATION: forward primer for detecting CRBN 5-prime
      targeting

<400> SEQUENCE: 12
ctgcattacc ggggttttta                                                20

<210> SEQ ID NO 13
<211> LENGTH: 20
<212> TYPE: DNA
<213> ORGANISM: Artificial Sequence
<220> FEATURE:
<223> OTHER INFORMATION: reverse primer for detecting CRBN 5-prime
      targeting

<400> SEQUENCE: 13
gctgttgttc caaactgtgc                                                20
```

```
<210> SEQ ID NO 14
<211> LENGTH: 20
<212> TYPE: DNA
<213> ORGANISM: Artificial Sequence
<220> FEATURE:
<223> OTHER INFORMATION: forward primer for detecting CRBN 3-prime
      targeting

<400> SEQUENCE: 14
cggaccgcta tcaggacata                                              20

<210> SEQ ID NO 15
<211> LENGTH: 20
<212> TYPE: DNA
<213> ORGANISM: Artificial Sequence
<220> FEATURE:
<223> OTHER INFORMATION: reverse primer for detecting CRBN 3-prime
      targeting

<400> SEQUENCE: 15
gccttccaat tgctttcact                                              20

<210> SEQ ID NO 16
<211> LENGTH: 20
<212> TYPE: DNA
<213> ORGANISM: Artificial Sequence
<220> FEATURE:
<223> OTHER INFORMATION: forward primer for genotyping

<400> SEQUENCE: 16
tgtgttgcct tcaaccatgt                                              20

<210> SEQ ID NO 17
<211> LENGTH: 20
<212> TYPE: DNA
<213> ORGANISM: Artificial Sequence
<220> FEATURE:
<223> OTHER INFORMATION: reverse primer for genotyping

<400> SEQUENCE: 17
cagcatgcct gctattgtct                                              20
```

TRANSGENIC MOUSE EXPRESSING HUMAN CEREBLON

CROSS-REFERENCE TO RELATED APPLICATIONS

The present application is a U.S. National Stage Application under 35 U.S.C. § 371 of International Patent Application No. PCT/US2017/013909, filed on Jan. 18, 2017, which claims priority to U.S. Provisional Patent Application No. 62/280,633 filed Jan. 19, 2016, the entirety of each of which is incorporated herein by reference.

1. FIELD

Provided herein are transgenic mice whose genome comprises a nucleic acid sequence encoding human cereblon (CRBN) or a fragment thereof. Also provided herein are methods for producing such transgenic mice. Further provided herein are methods for using these transgenic mice, for example, in evaluating efficacy, specificity, toxicity, pharmacokinetics, pharmacodynamics, mechanism of action of certain compounds in treating various diseases (such as cancer); optimizing dosing regimens of these compounds; and studying combinational therapies with other therapeutics for such diseases.

2. BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). A tremendous demand exists for new methods, treatments, and compositions that can be used to treat patients with cancer.

In the past decade, a group of immunomodulatory compounds, including thalidomide, lenalidomide, and pomalidomide, have been shown to elicit remarkable responses in patients with multiple myeloma, lymphoma, and other hematological diseases such as myelodysplastic syndrome. See Galustian et al., *Expert Opin. Pharmacother.* 2009, 10:125-133. These treatment compounds display a broad spectrum of activity, including anti-angiogenic properties, modulation of proinflammatory cytokines, co-stimulation of T cells, increased NK cell toxicity, direct anti-tumor effects, and modulation of stem cell differentiation.

A key molecular target that has recently been identified to bind to thalidomide is CRBN. See Ito et al., *Science* 2010, 327:1345-1350. At least two human CRBN isoforms have been identified, isoform 1 (442 amino acids) and isoform 2 (441 amino acids). Human isoform 2 is different from isoform 1 only in the deletion of amino acid 23 Alanine from isoform 1. CRBN and its associated proteins form an E3 ubiquitin ligase complex, which mediates ubiquitination and subsequent proteasomal degradation of target proteins. Thalidomide was found to inhibit auto-ubiquitination of CRBN in vitro, suggesting that thalidomide is an E3 ubiquitin ligase inhibitor. Id. Importantly, auto-ubiquitination of CRBN was inhibited by thalidomide in wild-type cells, but not in cells with CRBN mutations that prevent thalidomide binding. Id. The thalidomide binding site was mapped to a highly conserved C-terminal 104 amino acid region in CRBN. Id. Individual point mutants in CRBN isoform 1, Y384A and W386A, were both defective for thalidomide binding, with the double mutant having the lowest thalidomide-binding activity. Id.

Understanding the interactions between these compounds and CRBN or CRBN-associated proteins will facilitate elucidating molecular mechanisms of drug efficacy and/or toxicity and may lead to development of new drugs with improved efficacy and toxicity profiles.

An animal model suitable for studying the interaction between CRBN and CRBN E3 ubiquitin ligase modulating compounds (CMC) and the safety and efficacy of such compounds is indispensable. This disclosure fulfills these and other needs.

3. SUMMARY OF THE INVENTION

In one aspect, provided herein is a transgenic mouse whose genome comprises a nucleic acid sequence encoding human CRBN or a fragment thereof, wherein endogenous mouse CRBN is not expressed in the transgenic mouse. In one embodiment, the genome of the transgenic mouse comprises a nucleic acid sequence encoding human CRBN. In certain embodiments, the nucleic acid sequence encoding the human CRBN is stably integrated into a chromosome. In another embodiment, the genome of the transgenic mouse comprises a nucleic acid sequence encoding a fragment of human CRBN. In certain embodiments, the nucleic acid sequence encoding the fragment of the human CRBN is stably integrated into a chromosome. In some embodiments, the nucleic acid comprises a mouse-human chimeric CRBN gene. In certain embodiments, the nucleic acid sequence encodes a fragment of human CRBN that comprises a polypeptide that starts at codon 24 Glutamate of human CRBN isoform 1 and ends at the last codon of human CRBN isoform 1. In other embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In one embodiment, the transgenic mouse expresses a full-length human CRBN. In yet another embodiment, the transgenic mouse expresses a fragment of human CRBN.

In another aspect, provided is a cell derived from a transgenic mouse provided herein, wherein the cell comprises a nucleic acid sequence encoding human CRBN or a fragment thereof. In certain embodiments, the cell is obtained from the transgenic mouse. In one embodiment, the cell is an isolated cell. In one embodiment, the nucleic acid sequence encodes human CRBN. In certain embodiments, the nucleic acid sequence encoding the human CRBN is stably integrated into a chromosome of the transgenic mouse. In another embodiment, the nucleic acid sequence encodes a fragment of human CRBN. In certain embodiments, the nucleic acid sequence encoding the fragment of the human CRBN is stably integrated into a chromosome of the transgenic mouse. In some embodiments, the nucleic acid comprises a mouse-human chimeric CRBN gene. In certain embodiments, the nucleic acid sequence encodes a fragment of human CRBN that comprises a polypeptide that starts at codon 24 Glutamate of human CRBN isoform 1 and ends at the last codon of human CRBN isoform 1. In other embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In one embodiment, the cell expresses a full-length human CRBN. In yet another embodiment, the cell expresses a fragment of human CRBN.

In another aspect, provided is a cell line derived from a transgenic mouse provided herein, wherein the cell line comprises a nucleic acid sequence encoding human CRBN or a fragment thereof. In one embodiment, the cell line is an isolated cell line. In one embodiment, the nucleic acid sequence encodes human CRBN. In certain embodiments, the nucleic acid sequence encoding the human CRBN is stably integrated into a chromosome of the transgenic mouse. In another embodiment, the nucleic acid sequence encodes a fragment of human CRBN. In certain embodiments, the nucleic acid sequence encoding the fragment of the human CRBN is stably integrated into a chromosome of the transgenic mouse. In some embodiments, the nucleic acid comprises a mouse-human chimeric CRBN gene. In certain embodiments, the nucleic acid sequence encodes a fragment of human CRBN that comprises a polypeptide that starts at codon 24 Glutamate of human CRBN isoform 1 and ends at the last codon of human CRBN isoform 1. In other embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In one embodiment, the cell line is a transformed cell line. In another embodiment, the transformed cell line expresses a full-length human CRBN. In yet another embodiment, the transformed cell line expresses a fragment of human CRBN.

In another aspect, provided is a tissue derived from a transgenic mouse provided herein, wherein the tissue comprises a nucleic acid sequence encoding human CRBN or a fragment thereof. In certain embodiments, the tissue is obtained from the transgenic mouse. In one embodiment, the tissue is an isolated tissue. In one embodiment, the nucleic acid sequence encodes human CRBN. In certain embodiments, the nucleic acid sequence encoding the human CRBN is stably integrated into a chromosome of the transgenic mouse. In another embodiment, the nucleic acid sequence encodes a fragment of human CRBN. In certain embodiments, the nucleic acid sequence encoding the fragment of the human CRBN is stably integrated into a chromosome of the transgenic mouse. In some embodiments, the nucleic acid comprises a mouse-human chimeric CRBN gene. In certain embodiments, the nucleic acid sequence encodes a fragment of human CRBN that comprises a polypeptide that starts at codon 24 Glutamate of human CRBN isoform 1 and ends at the last codon of human CRBN isoform 1. In other embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In one embodiment, the tissue expresses a full-length human CRBN. In yet another embodiment, the tissue expresses a fragment of human CRBN.

In another aspect, provided is an organ derived from a transgenic mouse provided herein, wherein the organ comprises a nucleic acid sequence encoding human CRBN or a fragment thereof. In certain embodiments, the organ is obtained from the transgenic mouse. In one embodiment, the organ is an isolated organ. In one embodiment, the nucleic acid sequence encodes human CRBN. In certain embodiments, the nucleic acid sequence encoding the human CRBN is stably integrated into a chromosome of the transgenic mouse. In another embodiment, the nucleic acid sequence encodes a fragment of human CRBN. In certain embodiments, the nucleic acid sequence encoding the fragment of the human CRBN is stably integrated into a chromosome of the transgenic mouse. In some embodiments, the nucleic acid comprises a mouse-human chimeric CRBN gene. In certain embodiments, the nucleic acid sequence encodes a fragment of human CRBN that comprises a polypeptide that starts at codon 24 Glutamate of human CRBN isoform 1 and ends at the last codon of human CRBN isoform 1. In other embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In one embodiment, the organ expresses a full-length human CRBN. In yet another embodiment, the organ expresses a fragment of human CRBN.

In certain aspects, provided herein is a transgenic mouse expressing human CRBN or a fragment thereof. In certain embodiments, the transgenic mouse expresses a full-length human CRBN. In other embodiments, the transgenic mouse expresses a fragment of human CRBN.

In certain embodiments, the human CRBN is expressed from a mouse-human chimeric CRBN gene. In certain embodiments, the nucleic acid sequence encodes a fragment of human CRBN that comprises a polypeptide that starts at codon 24 Glutamate of human CRBN isoform 1 and ends at the last codon of human CRBN isoform 1. In other embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In certain embodiments, the expression of the human CRBN is controlled by a homologous mouse promoter. In a specific embodiment, the expression of the human CRBN is controlled by a homologous mouse CRBN promoter.

In another aspect, provided herein is a method for producing a transgenic mouse expressing human CRBN, comprising: (a) introducing a polynucleotide construct into a mouse egg, wherein the polynucleotide construct comprises a nucleic acid sequence encoding human CRBN or a fragment thereof; and (b) transferring the mouse egg into a female mouse. Also provided herein is a method for producing a transgenic mouse expressing human CRBN, comprising: (a) introducing a polynucleotide construct into a mouse embryo, wherein the polynucleotide construct comprises a nucleic acid sequence encoding human CRBN or a fragment thereof; and (b) transferring the mouse embryo into a female mouse. Also provided herein is a method for producing a transgenic mouse expressing human CRBN, comprising: (a) introducing a polynucleotide construct into a mouse embryonic stem (ES) cell, wherein the polynucleotide construct comprises a nucleic acid sequence encoding human CRBN or a fragment thereof; and (b) transferring the mouse ES cell into a female mouse. In certain embodiments, the nucleic acid sequence encodes human CRBN. In certain embodiments, the nucleic acid sequence encoding the human CRBN is stably integrated into a chromosome of the egg, embryo, or ES cell. In other embodiments, the nucleic acid sequence encodes a fragment of human CRBN. In certain embodiments, the nucleic acid sequence encoding the fragment of the human CRBN is stably integrated into a chromosome of the egg, embryo, or ES cell. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8.

In certain embodiments, the method further comprises breeding the female mouse. In other embodiments, the method further comprises selecting offspring having the nucleic acid sequence encoding the human CRBN or a fragment thereof. In some embodiments, the method further comprises breeding the female mouse, and selecting offspring having the nucleic acid sequence encoding the human CRBN or a fragment thereof. Thus, further provided herein is a method for producing a transgenic mouse expressing human CRBN, comprising: (a) introducing a polynucleotide construct into a mouse egg, wherein the polynucleotide construct comprises a nucleic acid sequence encoding human CRBN or a fragment thereof; (b) transferring the mouse egg into a female mouse; and (c) breeding the female mouse, and selecting an offspring transgenic mouse expressing the human CRBN or fragment thereof. Also provided herein is a method for producing a transgenic mouse expressing human CRBN, comprising: (a) introducing a polynucleotide construct into a mouse embryo, wherein the polynucleotide construct comprises a nucleic acid sequence encoding human CRBN or a fragment thereof; (b) transferring the mouse embryo into a female mouse; and (c) breeding the female mouse, and selecting an offspring transgenic mouse expressing the human CRBN or fragment thereof. Also provided herein is a method for producing a transgenic mouse expressing human CRBN, comprising: (a) introducing a polynucleotide construct into a mouse ES cell, wherein the polynucleotide construct comprises a nucleic acid sequence encoding human CRBN or a fragment thereof; (b) transferring the mouse ES cell into a female mouse; and (c) breeding the female mouse, and selecting an offspring transgenic mouse expressing the human CRBN or fragment thereof.

In yet another aspect, provided herein is a transgenic mouse expressing human CRBN or a fragment thereof produced by a method, comprising: (a) introducing a polynucleotide construct into a mouse egg, wherein the polynucleotide construct comprises a nucleic acid sequence encoding human CRBN or a fragment thereof; and (b) transferring the mouse egg into a female mouse. Also provided herein is a transgenic mouse expressing human CRBN or a fragment thereof produced by a method, comprising: (a) introducing a polynucleotide construct into a mouse embryo, wherein the polynucleotide construct comprises a nucleic acid sequence encoding human CRBN or a fragment thereof; and (b) transferring the mouse embryo into a female mouse. Also provided herein is a transgenic mouse expressing human CRBN or a fragment thereof produced by a method, comprising: (a) introducing a polynucleotide construct into a mouse ES cell, wherein the polynucleotide construct comprises a nucleic acid sequence encoding human CRBN or a fragment thereof; and (b) transferring the mouse ES cell into a female mouse. Further provided herein is a transgenic mouse expressing human CRBN or a fragment thereof produced by a method, comprising: (a) introducing a polynucleotide construct into a mouse egg, wherein the polynucleotide construct comprises a nucleic acid sequence encoding human CRBN or a fragment thereof; (b) transferring the mouse egg into a female mouse; and (c) breeding the female mouse, and selecting an offspring transgenic mouse expressing the human CRBN or fragment thereof. Also provided herein is a transgenic mouse expressing human CRBN or a fragment thereof produced by a method, comprising: (a) introducing a polynucleotide construct into a mouse embryo, wherein the polynucleotide construct comprises a nucleic acid sequence encoding human CRBN or a fragment thereof (b) transferring the mouse embryo into a female mouse; and (c) breeding the female mouse, and selecting an offspring transgenic mouse expressing the human CRBN or fragment thereof. Also provided herein is a transgenic mouse expressing human CRBN or a fragment thereof produced by a method, comprising: (a) introducing a polynucleotide construct into a mouse ES cell, wherein the polynucleotide construct comprises a nucleic acid sequence encoding human CRBN or a fragment thereof; (b) transferring the mouse ES cell into a female mouse; and (c) breeding the female mouse, and selecting an offspring transgenic mouse expressing the human CRBN or fragment thereof. In certain embodiments, the nucleic acid sequence encodes human CRBN. In certain embodiments, the nucleic acid sequence encoding the human CRBN is stably integrated into a chromosome of the egg, embryo, or ES cell. In other embodiments, the nucleic acid sequence encodes a fragment of human CRBN. In certain embodiments, the nucleic acid sequence encoding the fragment of the human CRBN is stably integrated into a chromosome of the egg, embryo, or ES cell. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8.

In specific embodiments herein, reference to a "human CRBN" refers to a full-length human CRBN.

In still another aspect, provided herein is a method for producing a transgenic mouse expressing human CRBN in a particular genetic background, wherein the method comprises breeding a transgenic mouse expressing human CRBN or a fragment thereof provided herein with a mouse of the genetic background. Also provided herein is a transgenic mouse expressing human CRBN in a particular genetic background produced by a method, comprising breeding a transgenic mouse expressing human CRBN or a fragment thereof provided herein with a mouse of the genetic background. In certain embodiments, the mouse of a genetic background is a NSG/NOG mouse model. In other embodiments, the mouse of a genetic background is a Vk*myc multiple myeloma mouse model. In yet other embodiments, the mouse of a genetic background is a Eu-v-abl/Eu-c-Myc multiple myeloma mouse model. In still other embodiments, the mouse of a genetic background is a Eu-c-Myc lymphoma mouse model. In one embodiment, the mouse of a genetic background is a human IKZF1 transgenic mouse model. In another embodiment, the mouse of a genetic background is a human IKZF3 transgenic mouse model.

In other aspects, provided are methods for using a transgenic mouse expressing human CRBN or a fragment thereof as provided herein.

In yet another aspect, provided herein is a method for evaluating the effect of a compound in a transgenic mouse expressing human CRBN or a fragment thereof, comprising:
   (a) administering the compound to the transgenic mouse;
   (b) obtaining a sample from the transgenic mouse;
   (c) measuring the level of a biomarker in the sample; and
   (d) comparing the level of the biomarker with a base level of the biomarker;
   wherein the biomarker is a CRBN-associated protein (CAP).

In yet another aspect, provided herein is a method for evaluating the effect of a combination of compounds in a transgenic mouse expressing human CRBN or a fragment thereof, comprising:
   (a) administering a first compound and a second compound to the transgenic mouse;
   (b) obtaining a sample from the transgenic mouse;
   (c) measuring the level of a biomarker in the sample; and
   (d) comparing the level of the biomarker with a base level of the biomarker;
   wherein the biomarker is a CAP.

In some embodiments, the method for evaluating the effect of a combination of compounds comprises administering a first compound, a second compound, and a third compound in the combination. In other embodiments, the method comprises administering more than three compounds in the combination. In certain embodiments, the compounds are administered concurrently. In other embodiments, the compounds are administered sequentially.

In certain embodiments, various transgenic mice used herein comprise a nucleic acid sequence encoding human CRBN. In certain embodiments, the nucleic acid sequence encoding the human CRBN is stably integrated into a mouse chromosome. In other embodiments, the nucleic acid sequence encodes a fragment of human CRBN. In certain embodiments, the nucleic acid sequence encoding the fragment of the human CRBN is stably integrated into a mouse chromosome. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8.

In certain embodiments, the base level of the biomarker is the level of the biomarker when no compound is administered to the transgenic mouse. In some embodiments, the base level of the biomarker is the level of the biomarker when only one compound is administered to the transgenic mouse. In certain embodiments, the only one compound is the first compound. In other embodiments, the only one compound is the second compound. In yet other embodiments, the only one compound is the third compound. In still other embodiments, the only one compound is a control compound. In some embodiments, the base level of the biomarker is the level of the biomarker when a reference combination of two compounds is administered to the transgenic mouse. In certain embodiments, the reference combination comprises the first compound and another compound. In other embodiments, the reference combination comprises the second compound and another compound. In yet other embodiments, the reference combination comprises the third compound and another compound. In still other embodiments, the reference combination comprises the first compound and the second compound. In certain embodiments, the reference combination comprises two or more other compounds (i.e., not the first compound or the second compound).

In certain embodiments, the effect of a compound (or a combination of compounds) is the effect on antigen-specific T-cell killing.

In another aspect, provided herein is a method for optimizing dosing amounts and/or schedules of a compound in a transgenic mouse expressing human CRBN or a fragment thereof, comprising:
   (a) administering the compound to the transgenic mouse;
   (b) obtaining a sample from the transgenic mouse;
   (c) measuring the level of a biomarker in the sample; and
   (d) adjusting the dosing amount and/or schedule of the compound based on the level of the biomarker;
   wherein the biomarker is a CAP.

In certain embodiments, the method is a method for optimizing dosing amounts. In other embodiments, the method is a method for optimizing dosing schedules. In certain embodiments, the method is a method for optimizing dosing schedules and dosing amounts. In certain embodiments, the transgenic mouse comprises a nucleic acid sequence encoding human CRBN. In certain embodiments, the nucleic acid sequence encoding the human CRBN is stably integrated into a mouse chromosome. In other embodiments, the nucleic acid sequence encodes a fragment of human CRBN. In certain embodiments, the nucleic acid sequence encoding the fragment of the human CRBN is stably integrated into a mouse chromosome. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8.

In some embodiments of the various methods provided herein, the biomarker comprises one or more biomarkers. In certain embodiments, the dosing amount of the compound is adjusted if the level of the biomarker is higher than a base level of the biomarker. In other embodiments, the dosing schedule of the compound is adjusted if the level of the biomarker is higher than a base level of the biomarker. In other embodiments, both the dosing amount and the dosing schedule of the compound are adjusted if the level of the biomarker is higher than a base level of the biomarker. In certain embodiments, the dosing amount of the compound is adjusted if the level of the biomarker is lower than a base level of the biomarker. In other embodiments, the dosing schedule of the compound is adjusted if the level of the biomarker is lower than a base level of the biomarker. In other embodiments, both the dosing amount and the dosing schedule of the compound are adjusted if the level of the biomarker is lower than a base level of the biomarker.

In some embodiments of the various method provided herein, the biomarker is eRF3a, eRF3b, eRF3c, IKZF1, IKZF3, CK1a, PABP1, eRF1, BIP, eEF1α, PERK, GCN2, eIF2a, ATF4, ATF3, DDIT3, PPP1R15A, TNFRSF10B, GADD45A, TNFRSF1A, TNFRSF1B, FAS, FADD, IRE1, XBP1, SEC24D, DNAJB9, EDEM1, EDEM2, HYOU1, ATF6, HSPA5, Caspase 8, BID, Caspase 9, Caspase 7, Caspase 3, PARP, Mcl-1, or BAD. In other embodiments of the various method provided herein, the biomarker is CDKN1A, Myc, IRF4, IRF7, IFIT1, IFIT3, RIG-I, MDA-5, TBK1, IKKe, ZFP91, ZNF198, MVP, Parp4, Ron, PDE6D, TLR3, STAT1, STAT2, STAT3, IFNa, IFNb, OAS1, OAS2, OAS3, IFIT2, ISG15, ISG20, IFI21, IFI35, IFI6, IFITM3, IFITM2WIZ, GBP2, GBP4, SELL, SNX20, KLF13, GBP1, MARCKS, SLAMF1, or SASH1. Each of the biomarkers provided herein includes various isoforms, phosphorylated forms, cleaved forms, modified forms, and splicing variants thereof. Combinations of these biomarkers are also contemplated.

In some embodiments of the various methods provided herein, the compound is an immunomodulatory compound. In certain embodiments, the immunomodulatory compound is selected from the group consisting of thalidomide, lenalidomide, and pomalidomide. In one embodiment, the immunomodulatory compound is thalidomide. In another embodiment, the immunomodulatory compound is lenalidomide. In yet another embodiment, the immunomodulatory compound is pomalidomide.

In certain embodiments of the various methods provided herein, the compound is a Pattern Recognition Receptor (PRR) agonist. In some embodiments, the PRR agonist is selected from the group consisting of TLR3 agonist, TLR7 agonist, TLR8 agonist, TLR9 agonist, RIG-1 agonist, MDA5 agonist, and AIM2 agonist. In one embodiment, the PRR agonist is TLR3 agonist. In another embodiment, the PRR agonist is TLR7 agonist. In yet another embodiment, the PRR agonist is TLR8 agonist. In still another embodiment, the PRR agonist is TLR9 agonist. In one embodiment, the PRR agonist is RIG-1 agonist. In another embodiment, the PRR agonist is MDA5 agonist. In yet another embodiment, the PRR agonist is AIM2 agonist.

In other embodiments of the various methods provided herein, the compound is an antibody. In some embodiments, the antibody is selected from the group consisting of PD-1 antibody, PD-L1 antibody, PD-L2 antibody, CTLA-4 antibody, CD38 antibody, and SLAMF7 antibody. In one embodiment, the antibody is PD-1 antibody. In another embodiment, the antibody is PD-L1 antibody. In yet another embodiment, the antibody is PD-L2 antibody. In still another embodiment, the antibody is CTLA-4 antibody. In one embodiment, the antibody is CD38 antibody. In another embodiment, the antibody is SLAMF7 antibody.

In some embodiments, the antibody is selected from the group consisting of nivolumab (i.e., BMS-936558, MDX-1106, ONO-4538), MK-3475 (i.e., pembrolizumab, lambrolizumab), pidilizumab (i.e., CT-011), MEDI-0680 (i.e., AMP-514), PDR-001, durvalumab (i.e., MEDI-4736), BMS-936559 (i.e., MDX-1105), avelumab (i.e., MSB0010718C), atezolizumab (i.e., MPDL-3280A), ipilimumab, daratumumab, and elotuzumab. In one embodiment, the antibody is nivolumab. In another embodiment, the antibody is MK-3475. In yet another embodiment, the antibody is pidilizumab. In still another embodiment, the antibody is MEDI-0680. In one embodiment, the antibody is PDR-001. In another embodiment, the antibody is durvalumab. In yet another embodiment, the antibody is BMS-936559. In still another embodiment, the antibody is avelumab. In one embodiment, the antibody is atezolizumab. In another embodiment, the antibody is ipilimumab. In yet another embodiment, the antibody is daratumumab. In still another embodiment, the antibody is elotuzumab.

In yet other embodiments of the various methods provided herein, the compound is a molecular mimic. In some embodiments, the molecular mimic is selected from the group consisting of azacytidine, romidepsin, ATRA, cyclophosphamid, and Celebrex®. In one embodiment, the molecular mimic is azacytidine. In another embodiment, the molecular mimic is romidepsin. In yet another embodiment, the molecular mimic is ATRA. In still another embodiment, the molecular mimic is cyclophosphamid. In one embodiment, the molecular mimic is Celebrex®.

In still other embodiments of the various methods provided herein, the compound is an inhibitor of an enzyme (e.g., histone deacetylase (HDAC)) or a protein degradation apparatus (e.g., proteasome). In some embodiments, the compound is an inhibitor of a HDAC. In a particular embodiment, the compound is an inhibitor of HADC6. In a specific embodiment, the compound is ACY-241. In other embodiments, the compound is an inhibitor of a proteasome. In one embodiment, the compound is carfilzomib. In another embodiment, the compound is ixazomib.

In some embodiments, the compound is an anti-cancer compound. In certain embodiments, the compound is an anthracycline.

In one embodiment, one of the compounds in the combination is dexamethasone. In another embodiment, one of the compounds in the combination is a CMC. In yet another embodiment, one of the compounds in the combination is an immunomodulatory compound. In still another embodiment, one of the compounds in the combination is an immunomodulatory compound selected from the group consisting of thalidomide, lenalidomide, and pomalidomide. In one embodiment, one of the compounds in the combination is thalidomide. In another embodiment, one of the compounds in the combination is lenalidomide. In yet another embodiment, one of the compounds in the combination is pomalidomide.

In certain embodiments, one of the compounds in the combination is selected from the group consisting of ixazomib, carfilzomib, elotuzumab, daratumumab, azacytidine, ACY-241, cyclophosphamide, durvalumab, abraxane, and nivolumab. In one embodiment, one of the compounds in the combination is ixazomib. In another embodiment, one of the compounds in the combination is carfilzomib. In yet another embodiment, one of the compounds in the combination is elotuzumab. In still another embodiment, one of the compounds in the combination is daratumumab. In one embodiment, one of the compounds in the combination is azacytidine. In another embodiment, one of the compounds in the combination is ACY-241. In yet another embodiment, one of the compounds in the combination is cyclophosphamide. In still another embodiment, one of the compounds in the combination is durvalumab. In one embodiment, one of the compounds in the combination is abraxane. In another embodiment, one of the compounds in the combination is nivolumab.

In one embodiment, the combination of compounds comprises dexamethasone and a CMC. In another embodiment, the combination of compounds comprises dexamethasone and an immunomodulatory compound. In yet another embodiment, the combination of compounds comprises dexamethasone and an immunomodulatory compound selected from the group consisting of thalidomide, lenalidomide, and pomalidomide. In one embodiment, the combination of compounds comprises dexamethasone and thalidomide. In another embodiment, the combination of compounds comprises dexamethasone and lenalidomide. In yet another embodiment, the combination of compounds comprises dexamethasone and pomalidomide.

In one embodiment, the combination of compounds comprises dexamethasone, a CMC, and a compound selected from the group consisting of ixazomib, carfilzomib, elotuzumab, daratumumab, azacytidine, ACY-241, cyclophosphamide, durvalumab, abraxane, and nivolumab. In another embodiment, the combination of compounds comprises dexamethasone, an immunomodulatory compound, and a compound selected from the group consisting of ixazomib, carfilzomib, elotuzumab, daratumumab, azacytidine, ACY-241, cyclophosphamide, durvalumab, abraxane, and nivolumab. In yet another embodiment, the combination of compounds comprises dexamethasone, thalidomide, and a compound selected from the group consisting of ixazomib, carfilzomib, elotuzumab, daratumumab, azacytidine, ACY-241, cyclophosphamide, durvalumab, abraxane, and nivolumab. In still another embodiment, the combination of compounds comprises dexamethasone, lenalidomide, and a compound selected from the group consisting of ixazomib, carfilzomib, elotuzumab, daratumumab, azacytidine, ACY-241, cyclophosphamide, durvalumab, abraxane, and nivolumab. In still another embodiment, the combination of compounds comprises dexamethasone, pomalidomide, and a compound selected from the group consisting of ixazomib, carfilzomib, elotuzumab, daratumumab, azacytidine, ACY-241, cyclophosphamide, durvalumab, abraxane, and nivolumab.

In one embodiment, the combination of compounds comprises dexamethasone, a CMC, and ixazomib. In another embodiment, the combination of compounds comprises dexamethasone, a CMC, and carfilzomib. In yet another embodiment, the combination of compounds comprises dexamethasone, a CMC, and elotuzumab. In still another embodiment, the combination of compounds comprises dexamethasone, a CMC, and daratumumab. In one embodiment, the combination of compounds comprises dexamethasone, a CMC, and azacytidine. In another embodiment, the combination of compounds comprises dexamethasone, a CMC, and ACY-241. In yet another embodiment, the combination of compounds comprises dexamethasone, a CMC, and a cyclophosphamide. In still another embodiment, the combination of compounds comprises dexamethasone, a CMC, and durvalumab. In one embodiment, the combination of compounds comprises dexamethasone, a CMC, and abraxane. In another embodiment, the combination of compounds comprises dexamethasone, a CMC, and nivolumab.

In one embodiment, the combination of compounds comprises dexamethasone, an immunomodulatory compound, and ixazomib. In another embodiment, the combination of compounds comprises dexamethasone, an immunomodulatory compound, and carfilzomib. In yet another embodiment, the combination of compounds comprises dexamethasone, an immunomodulatory compound, and elotuzumab. In still another embodiment, the combination of compounds comprises dexamethasone, an immunomodulatory compound, and daratumumab. In one embodiment, the combination of compounds comprises dexamethasone, an immunomodulatory compound, and azacytidine. In another embodiment, the combination of compounds comprises dexamethasone, an immunomodulatory compound, and ACY-241. In yet another embodiment, the combination of compounds comprises dexamethasone, an immunomodulatory compound, and a cyclophosphamide. In still another embodiment, the combination of compounds comprises dexamethasone, an immunomodulatory compound, and durvalumab. In one embodiment, the combination of compounds comprises dexamethasone, an immunomodulatory compound, and abraxane. In another embodiment, the combination of compounds comprises dexamethasone, an immunomodulatory compound, and nivolumab.

In one embodiment, the combination of compounds comprises dexamethasone, thalidomide, and ixazomib. In another embodiment, the combination of compounds comprises dexamethasone, thalidomide, and carfilzomib. In yet another embodiment, the combination of compounds comprises dexamethasone, thalidomide, and elotuzumab. In still another embodiment, the combination of compounds comprises dexamethasone, thalidomide, and daratumumab. In one embodiment, the combination of compounds comprises dexamethasone, thalidomide, and azacytidine. In another embodiment, the combination of compounds comprises dexamethasone, thalidomide, and ACY-241. In yet another embodiment, the combination of compounds comprises dexamethasone, thalidomide, and a cyclophosphamide. In still another embodiment, the combination of compounds comprises dexamethasone, thalidomide, and durvalumab. In one embodiment, the combination of compounds comprises dexamethasone, thalidomide, and abraxane. In another embodiment, the combination of compounds comprises dexamethasone, thalidomide, and nivolumab.

In one embodiment, the combination of compounds comprises dexamethasone, lenalidomide, and ixazomib. In another embodiment, the combination of compounds comprises dexamethasone, lenalidomide, and carfilzomib. In yet another embodiment, the combination of compounds comprises dexamethasone, lenalidomide, and elotuzumab. In still another embodiment, the combination of compounds comprises dexamethasone, lenalidomide, and daratumumab. In one embodiment, the combination of compounds comprises dexamethasone, lenalidomide, and azacytidine. In another embodiment, the combination of compounds comprises dexamethasone, lenalidomide, and ACY-241. In yet another embodiment, the combination of compounds comprises dexamethasone, lenalidomide, and a cyclophosphamide. In still another embodiment, the combination of compounds comprises dexamethasone, lenalidomide, and durvalumab. In one embodiment, the combination of compounds comprises dexamethasone, lenalidomide, and abraxane. In another embodiment, the combination of compounds comprises dexamethasone, lenalidomide, and nivolumab.

In one embodiment, the combination of compounds comprises dexamethasone, pomalidomide, and ixazomib. In another embodiment, the combination of compounds comprises dexamethasone, pomalidomide, and carfilzomib. In yet another embodiment, the combination of compounds comprises dexamethasone, pomalidomide, and elotuzumab. In still another embodiment, the combination of compounds comprises dexamethasone, pomalidomide, and daratumumab. In one embodiment, the combination of compounds comprises dexamethasone, pomalidomide, and azacytidine. In another embodiment, the combination of compounds comprises dexamethasone, pomalidomide, and ACY-241. In yet another embodiment, the combination of compounds comprises dexamethasone, pomalidomide, and a cyclophosphamide. In still another embodiment, the combination of compounds comprises dexamethasone, pomalidomide, and durvalumab. In one embodiment, the combination of compounds comprises dexamethasone, pomalidomide, and abraxane. In another embodiment, the combination of compounds comprises dexamethasone, pomalidomide, and nivolumab.

4. BRIEF DESCRIPTION OF THE FIGURES

FIG. 1 shows the flow chart of producing a human CRBN knock-in transgenic mouse.

FIG. 2 shows the design of knocking in human CRBN in a mouse genome: (A) a portion of the mouse CRBN gene (including exon 2 and exon 3) in a mouse genome; (B) a targeting construct containing part of the human CRBN cDNA (starting from codon 24 of human CRBN isoform 1), bGH pA, and a Neomycin selection cassette flanked by two loxP sites; (C) the targeted genome after human CRBN knock-in; (D) the targeted genome after Cre excision of the Neomycin selection cassette.

FIGS. 3A-3C illustrate the cloning strategy for one example of donor vectors, CRBN KI Vector V2-pUC. FIG. 3A illustrates the synthesized CRBN KI Targeting Construct lacking a Neomycin selection cassette. Kpn I and Xho I restriction sites are the insertion site for the Neomycin selection cassette. FIG. 3B shows the map of PB-MV1Neo, which includes the Neomycin selection cassette, a 1637 bp piece that will be cut out by Kpn I and Xho I then inserted into the CRBN KI Targeting Construct. FIG. 3C shows the map of CRBN KI Vector V2-pUC, comprising (1) the backbone of a pUC57-Simple cloning vector, (2) a human cDNA sequence encoding a fragment of CRBN (starting from codon 24, Glutamate, and ending at the stop codon) consisting of the nucleic acid sequence of SEQ ID NO: 7, followed by a recombinant poly(A) sequence (e.g., bGH pA) and a Neomycin selection cassette controlled by a PGK-EM7 promoter and flanked by two loxP sites, and (3) a 5' homology arm consisting of nucleotides 1-1508 of the nucleic acid sequence of SEQ ID NO: 8 and a 3' homology arm consisting of nucleotides 4782-6282 of SEQ ID NO: 8.

Figure 8A:
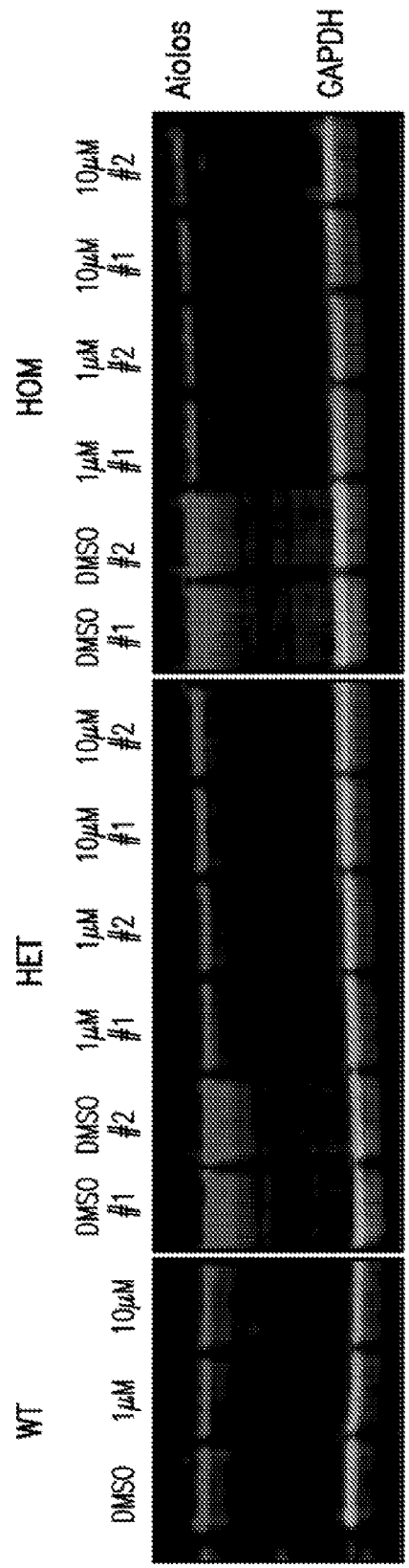
Figure 8B:
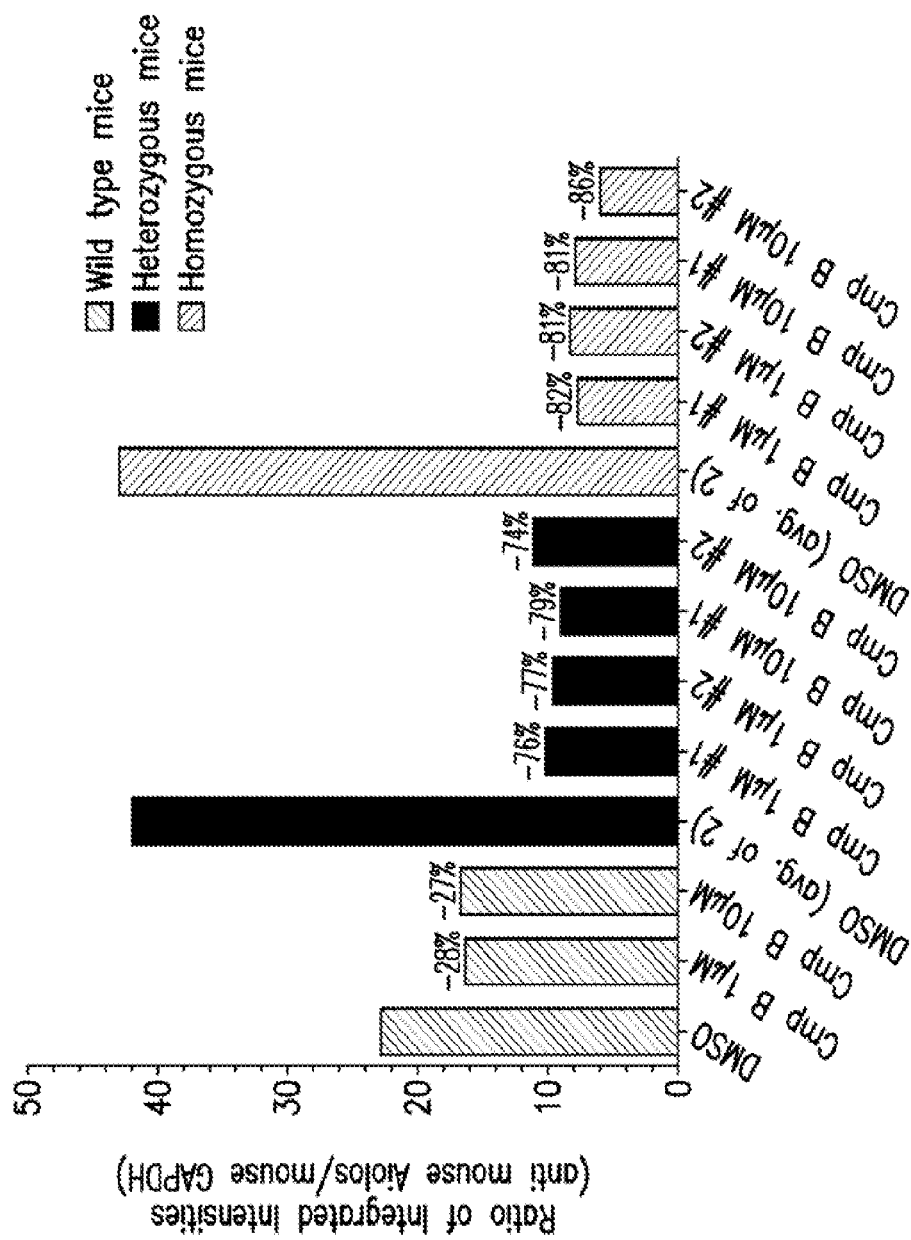

FIGS. 8A and 8B show degradation of Aiolos in splenocytes isolated from wild type mouse, heterozygous human CRBN transgenic mouse, or homozygous human CRBN transgenic mouse, following a 24 hr ex vivo treatment of Compound B at 1 µM or 10 µM. FIG. 8A shows the Western Blots. FIG. 8B shows the ratio of integrated intensities (Aiolos verus internal control GAPDH).

Figure 9A:
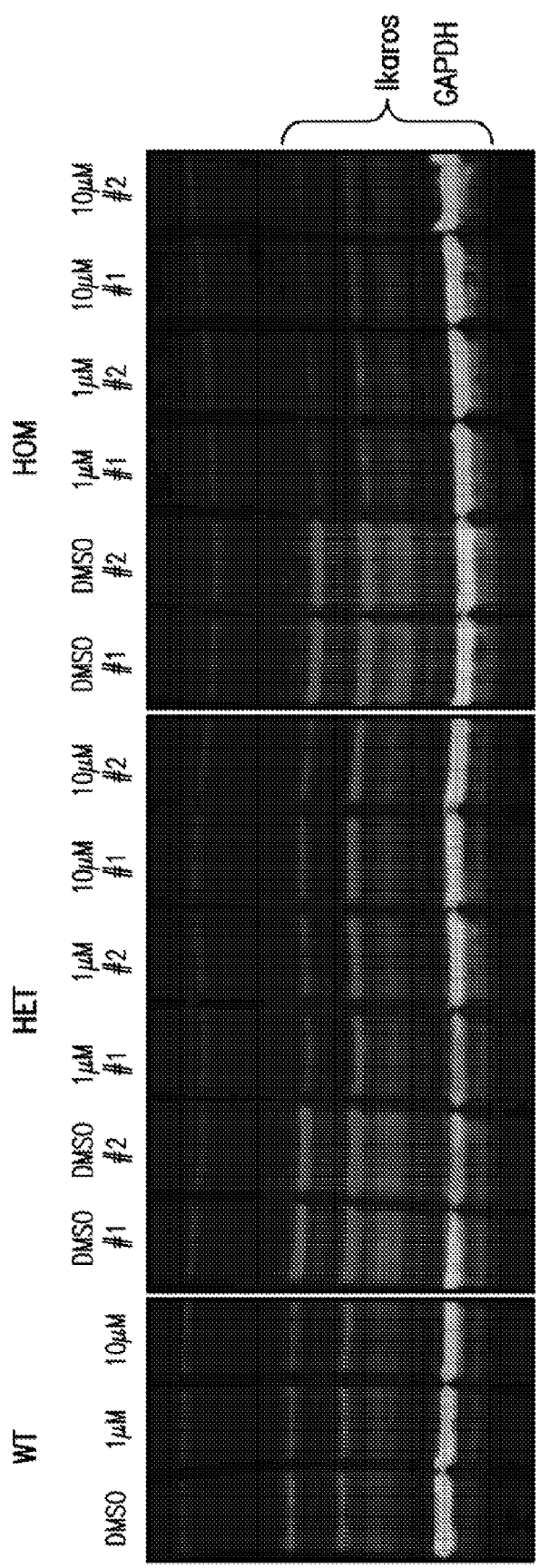
Figure 9B:
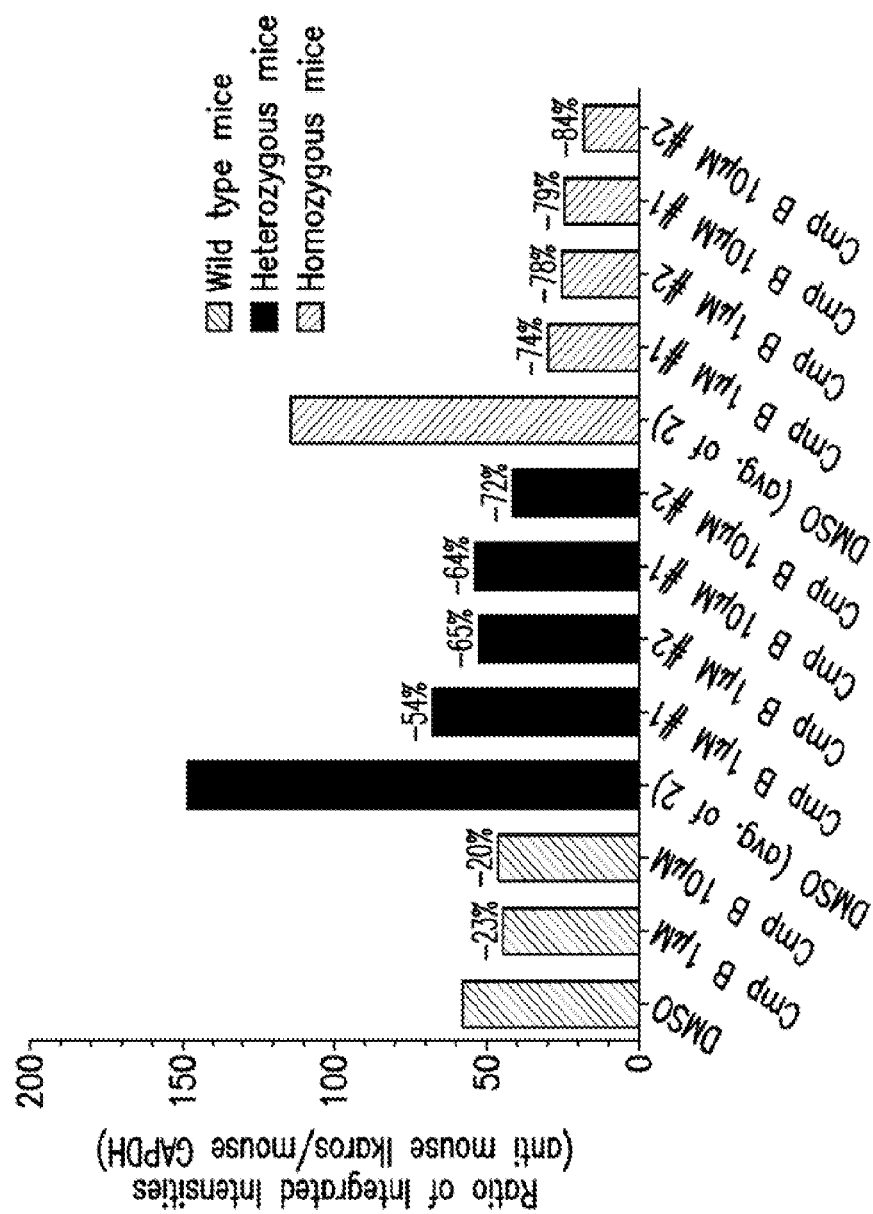

FIGS. 9A and 9B show degradation of Ikaros in splenocytes isolated from wild type mouse, heterozygous human CRBN transgenic mouse, or homozygous human CRBN transgenic mouse, following a 24 hr ex vivo treatment of Compound B at 1 µM or 10 µM. FIG. 9A shows the Western Blots. FIG. 9B shows the ratio of integrated intensities (Ikaros verus internal control GAPDH).

Figure 10A:
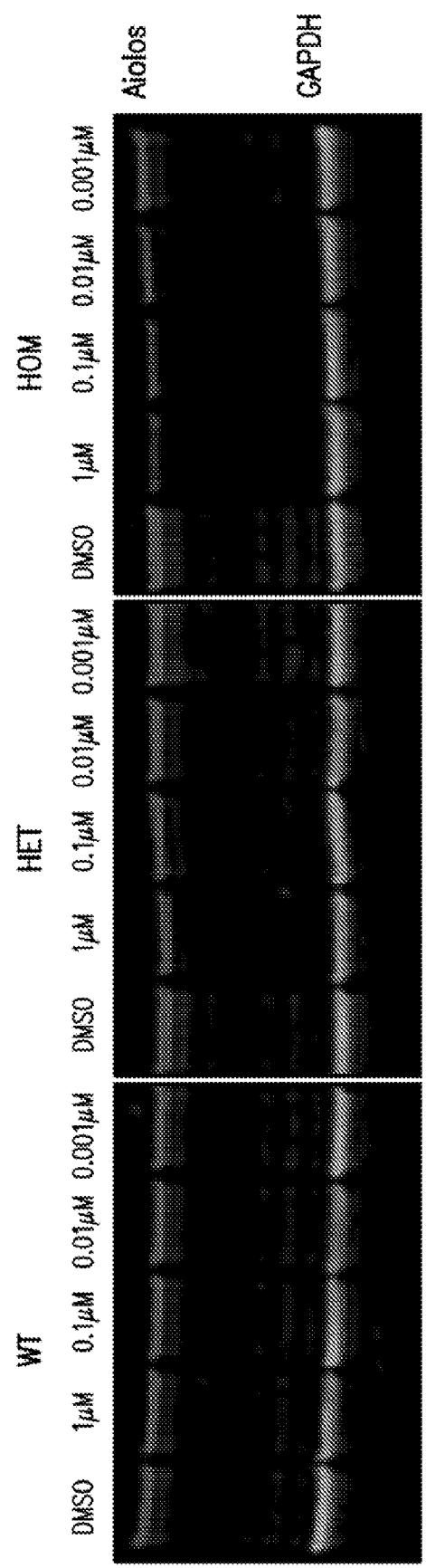
Figure 10B:
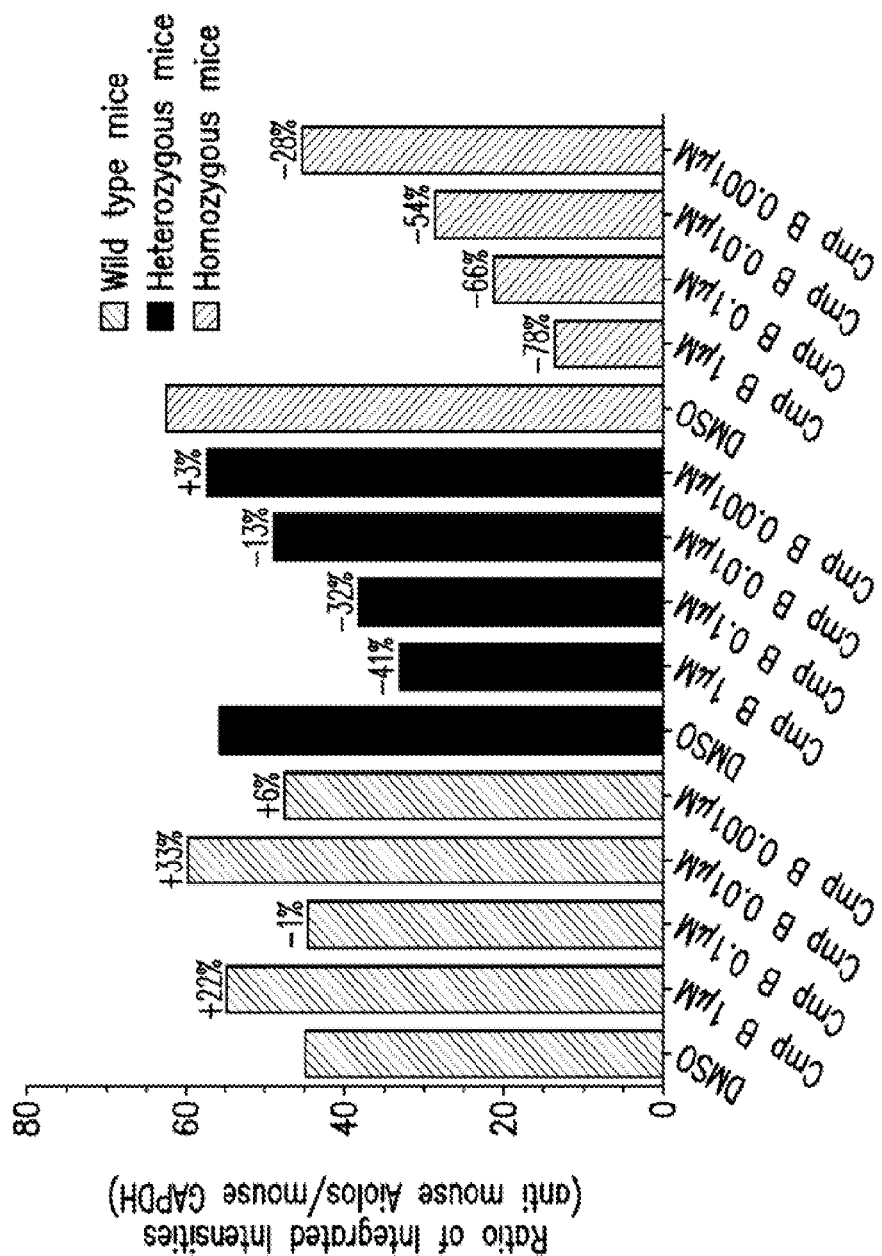

FIGS. 10A and 10B show that degradation of Aiolos was dependent on the concentration of Compound B in splenocytes isolated from wild type mouse, heterozygous human CRBN transgenic mouse, or homozygous human CRBN transgenic mouse, following a 6 hr ex vivo treatment of Compound B at 0.001 µM, 0.01 µM, 0.1 µM, or 1 µM. FIG. 10A shows the Western Blots. FIG. 10B shows the ratio of integrated intensities (Aiolos verus internal control GAPDH).

Figure 11A:
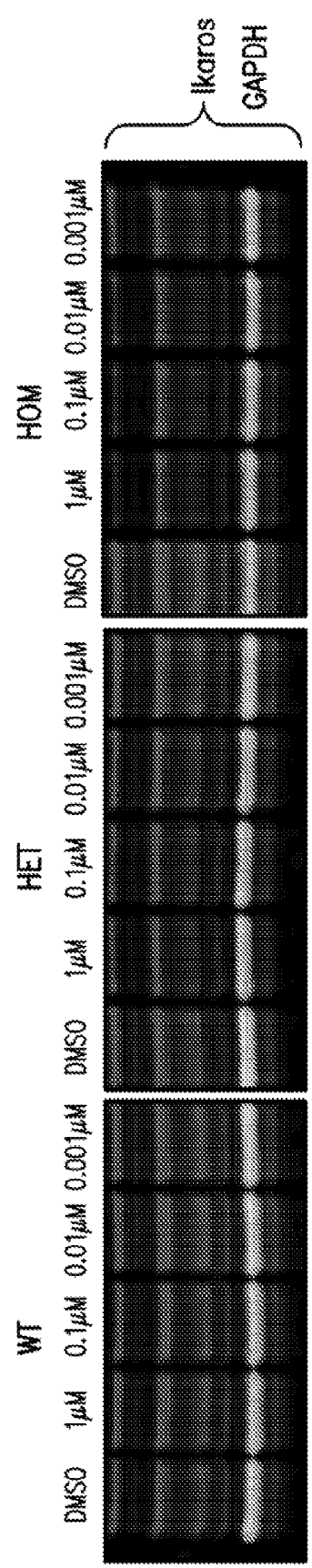
Figure 11B:
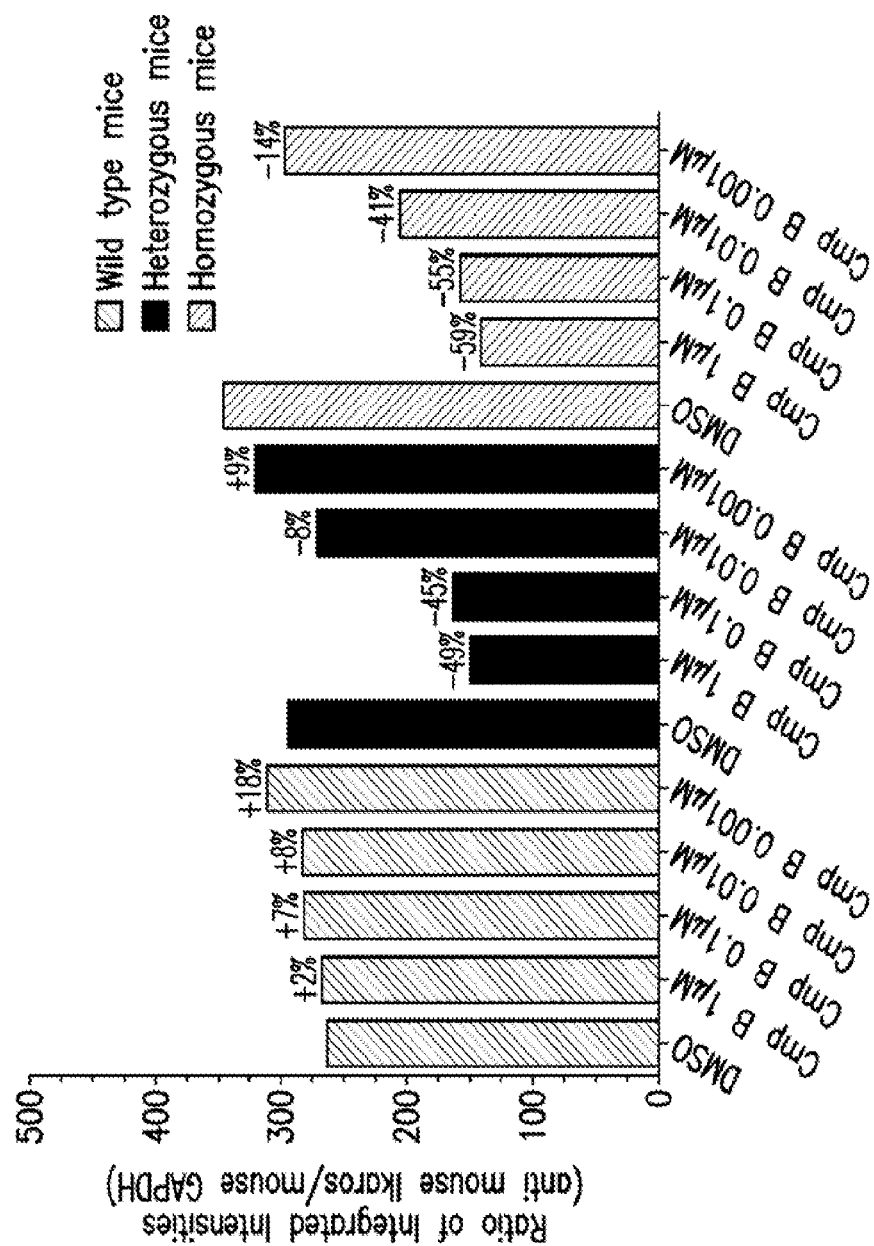

FIGS. 11A and 11B show that degradation of Ikaros was dependent on the concentration of Compound B in splenocytes isolated from wild type mouse, heterozygous human CRBN transgenic mouse, or homozygous human CRBN transgenic mouse, following a 6 hr ex vivo treatment of Compound B at 0.001 µM, 0.01 µM, 0.1 µM, or 1 µM. FIG. 11A shows the Western Blots. FIG. 11B shows the ratio of integrated intensities (Ikaros verus internal control GAPDH).

Figure 12A:
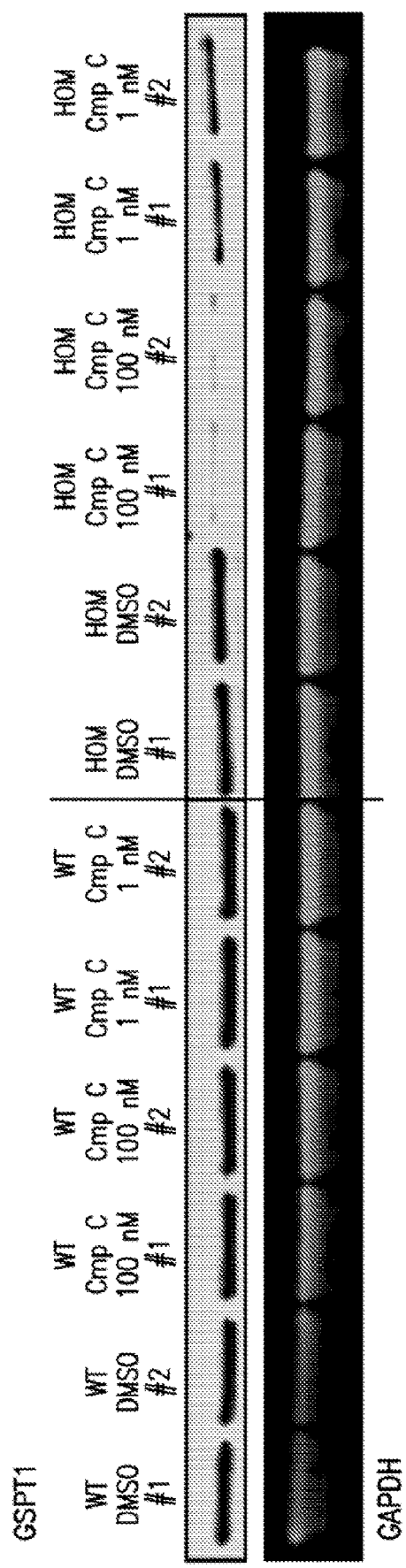
Figure 12B:
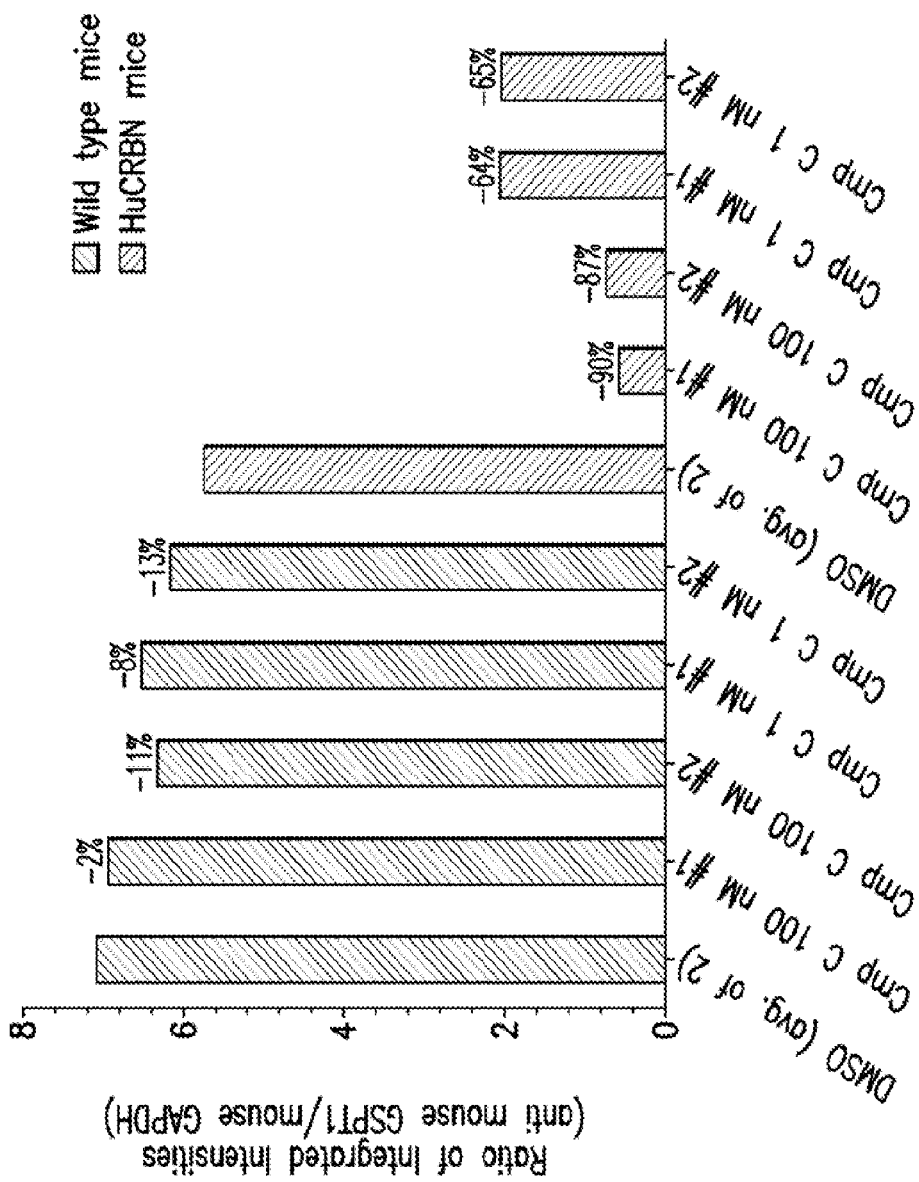

FIGS. 12A and 12B show degradation of GSPT1 in splenocytes isolated from wild type mouse or homozygous human CRBN transgenic mouse, following a 4 hr ex vivo treatment of Compound C at 1 nM or 100 nM. FIG. 12A shows the Western Blots. FIG. 12B shows the ratio of integrated intensities (GSPT1 verus internal control GAPDH).

Figure 13A:
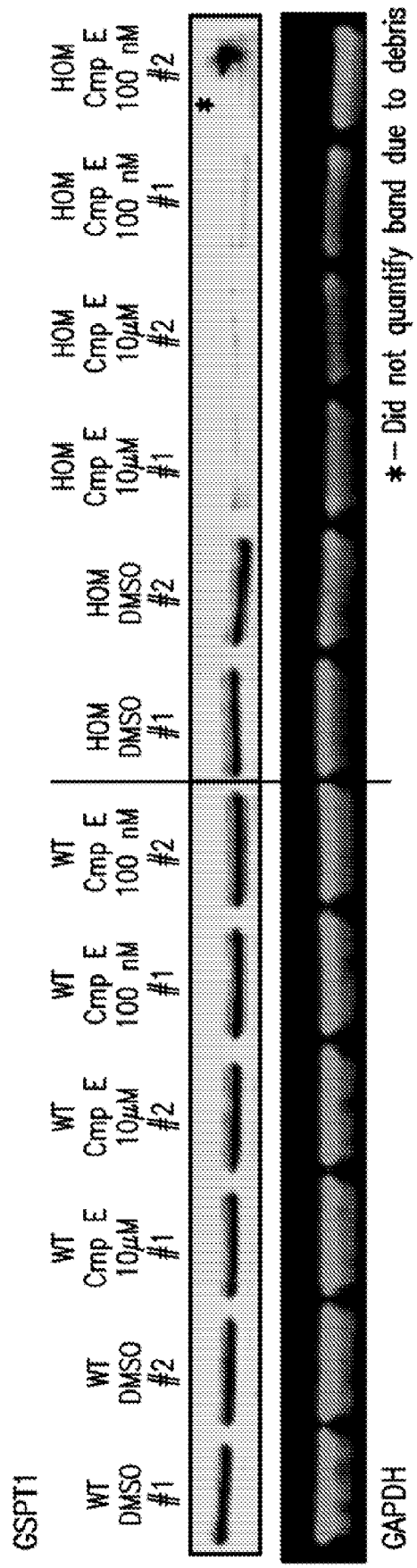
Figure 13B:
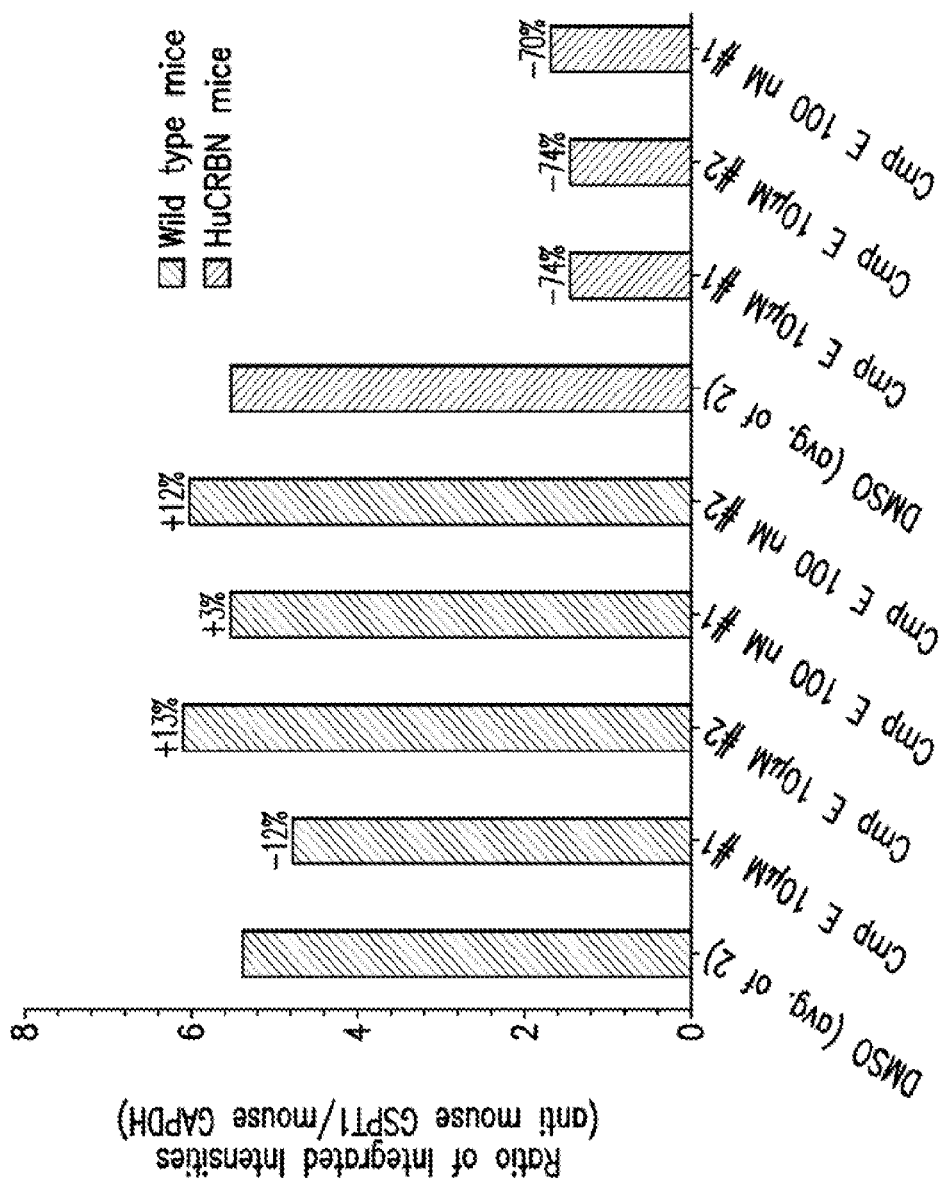

FIGS. 13A and 13B show degradation of GSPT1 in splenocytes isolated from wild type mouse or homozygous human CRBN transgenic mouse, following a 4 hr ex vivo treatment of Compound E at 100 nM or 10 µM. FIG. 13A shows the Western Blots. FIG. 13B shows the ratio of integrated intensities (GSPT1 verus internal control GAPDH).

5. DETAILED DESCRIPTION OF THE INVENTION

The methods provided herein are based, in part, on the discovery that the mouse E3 ubiquitin ligase complex can be activated by human CRBN without requiring other humanized subunits of the complex.

Provided herein are human CRBN transgenic animals, and cells, cell lines, tissues, or organs therefrom that express human CRBN. Also provided are methods for producing human CRBN transgenic animals and methods for using such transgenic animals.

An animal model suitable for studying the interaction between CRBN and a CMC and the safety and efficacy of a CMC is provided herein. A mouse is a useful animal model; however, mouse CRBN does not properly engage with certain compounds that bind to human CRBN (such as thalidomide). As a result, many essential questions regarding such compounds cannot be adequately answered in a mouse model. Thus, the transgenic mice expressing human CRBN provided herein are useful in addressing important questions related to the development of new drugs targeting CRBN, such as efficacy, toxicity, specificity, and mechanism of action, etc. Also, this transgenic mouse can be bred with other disease model mice to create a broader spectrum of genetic background for further studies.

Before the present disclosure is further described, it is to be understood that the disclosure is not limited to the particular embodiments set forth herein, and it is also to be understood that the terminology used herein is for the purpose of describing particular embodiments only, and is not intended to be limiting.

5.1 Definitions

The term "human cereblon," "human CRBN," or "hCRBN" refers to the polypeptides ("polypeptides," "peptides," and "proteins" are used interchangeably herein) comprising the amino acid sequence of a human CRBN protein (e.g., human CRBN isoform 1, GenBank Accession No. NP_057386, which has an amino acid sequence as follows:

(SEQ ID NO: 1)
MAGEGDQQDAAHNMGNHLPLLPAESEEEDEMEVEDQDSKEAKKPNIINFD

TSLPTSHTYLGADMEEFHGRTLHDDDSCQVIPVLPQVMMILIPGQTLPLQ

LFHPQEVSMVRNLIQKDRTFAVLAYSNVQEREAQFGTTAEIYAYREEQDF

GIEIVKVKAIGRQRFKVLELRTQSDGIQQAKVQILPECVLPSTMSAVQLE

SLNKCQIFPSKPVSREDQCSYKWWQKYQKRKFHCANLTSWPRWLYSLYDA

ETLMDRIKKQLREWDENLKDDSLPSNPIDFSYRVAACLPIDDVLRIQLLK

IGSAIQRLRCELDIMNKCTSLCCKQCQETEITTKNEIFSLSLCGPMAAYV

NPHGYVHETLTVYKACNLNLIGRPSTEHSWFPGYAWTVAQCKICASHIGW

KFTATKKDMSPQKFWGLTRSALLPTIPDTEDEISPDKVILCL;

or human CRBN isoforms 2, GenBank Accession No. NP_001166953, which has an amino acid sequence as follows:

(SEQ ID NO: 2)
MAGEGDQQDAAHNMGNHLPLLPESEEEDEMEVEDQDSKEAKKPNIINFDT

SLPTSHTYLGADMEEFHGRTLHDDDSCQVIPVLPQVMMILIPGQTLPLQL

FHPQEVSMVRNLIQKDRTFAVLAYSNVQEREAQFGTTAEIYAYREEQDFG

IEIVKVKAIGRQRFKVLELRTQSDGIQQAKVQILPECVLPSTMSAVQLES

LNKCQIFPSKPVSREDQCSYKWWQKYQKRKFHCANLTSWPRWLYSLYDAE

TLMDRIKKQLREWDENLKDDSLPSNPIDFSYRVAACLPIDDVLRIQLLKI

GSAIQRLRCELDIMNKCTSLCCKQCQETEITTKNEIFSLSLCGPMAAYVN

PHGYVHETLTVYKACNLNLIGRPSTEHSWFPGYAWTVAQCKICASHIGWK

FTATKKDMSPQKFWGLTRSALLPTIPDTEDEISPDKVILCL, each of which is herein incorporated by reference in its entirety), and related polypeptides, including SNP variants thereof. Related human CRBN polypeptides include allelic variants (e.g., SNP variants), splice variants, fragments, derivatives, substitution variant, deletion variant, insertion variant, fusion polypeptides, and interspecies homologs, which, in certain embodiments, retain human CRBN activity and/or are sufficient to generate an anti-hCRBN immune response.

The term "mouse cereblon," "mouse CRBN," or "mCRBN" refers to the polypeptides ("polypeptides," "peptides," and "proteins" are used interchangeably herein) comprising the amino acid sequence of a mouse CRBN protein (e.g., mouse CRBN isoform 1, GenBank Accession No. NP_067424.2, which has an amino acid sequence as follows:

(SEQ ID NO: 3)
MAGEGDQQDAAHNMGNHLPLLPDSEDEDDEIEMEVEDQDSKEARKPNIIN

FDTSLPTSHTYLGADMEEFHGRTLHDDDSCQVIPVLPEVLMILIPGQTLP

LQLSHPQEVSMVRNLIQKDRTFAVLAYSNVQEREAQFGTTAEIYAYREEQ

EFGIEVVKVKAIGRQRFKVLELRTQSDGIQQAKVQILPECVLPSTMSAVQ

LESLNKCQVFPSKPISWEDQYSCKWWQKYQKRKFHCANLTSWPRWLYSLY

DAETLMDRIKKQLREWDENLKDDSLPENPIDFSYRVAACLPIDDVLRIQL

LKIGSAIQRLRCELDIMNKCTSLCCKQCQETEITTKNEIFSLSLCGPMAA

YVNPHGYVHETLTVYKASNLNLIGRPSTVHSWFPGYAWTIAQCKICASHI

GWKFTATKKDMSPQKFWGLTRSALLPTIPETEDEISPDKVILCL;

or mouse CRBN isoforms 2, GenBank Accession No. NP_780566.1, which has an amino acid sequence as follows:

(SEQ ID NO: 4)
MAGEGDQQDAAHNMGNHLPLLPADSEDEDDEIEMEVEDQDSKEARKPNII

NFDTSLPTSHTYLGADMEEFHGRTLHDDDSCQVIPVLPEVLMILIPGQTL

PLQLSHPQEVSMVRNLIQKDRTFAVLAYSNVQEREAQFGTTAEIYAYREE

QEFGIEVVKVKAIGRQRFKVLELRTQSDGIQQAKVQILPECVLPSTMSAV

QLESLNKCQVFPSKPISWEDQYSCKWWQKYQKRKFHCANLTSWPRWLYSL

YDAETLMDRIKKQLREWDENLKDDSLPENPIDFSYRVAACLPIDDVLRIQ

LLKIGSAIQRLRCELDIMNKCTSLCCKQCQETEITTKNEIFSLSLCGPMA

AYVNPHGYVHETLTVYKASNLNLIGRPSTVHSWFPGYAWTIAQCKICASH

IGWKFTATKKDMSPQKFWGLTRSALLPTIPETEDEISPDKVILCL, each of which is herein incorporated by reference in its entirety), and related polypeptides, including SNP variants thereof. Related mouse CRBN polypeptides include allelic variants (e.g., SNP variants), splice variants, fragments, derivatives, substitution variant, deletion variant, insertion variant, fusion polypeptides, and interspecies homologs, which, in certain embodiments, retain mouse CRBN activity and/or are sufficient to generate an anti-mCRBN immune response.

As used herein, the term "cereblon-associated protein," "CRBN-associated protein," or "CAP" refers to a protein that interacts with or binds to a CRBN protein from any species (e.g., hCRBN or mCRBN) directly or indirectly. For example, the term refers to any protein that directly binds to cereblon, as well as any protein that is an indirect downstream effector of cereblon pathways. In certain embodiments, a "CAP" is a substrate of CRBN, for example, a protein substrate of the E3 ubiquitin ligase complex involving CRBN, or a downstream substrate thereof.

The term "animal" as used herein includes all vertebrate and invertebrate animals, except humans. It also includes an individual animal in all stages of development, including embryonic and fetal stages.

The term "transgenic animal" refers to an animal (e.g., mouse, rat, hamster, pig, cow, etc.), having a non-endogenous (i.e., exogenous) nucleic acid sequence as an extra-chromosomal element in some or all of its cells or stably integrated into its germ line DNA (i.e., in the genomic sequence of most or all of its cells). Heterologous nucleic acid is introduced into the germ line of such transgenic animals by genetic manipulation of, for example, eggs, embryos, or embryonic stem cells of the host animal and subsequent breeding of offspring animals that are generated from the genetically manipulated eggs, embryos, or embryonic stem cells.

A transgenic animal with "germline transmission" refers to a transgenic animal in which the genetic information was introduced into a germline cell, thereby conferring the ability to transfer the genetic information to offspring. If such offspring in fact possess some or all of that genetic information, the offspring are also transgenic animals.

The term "transfection" refers to the uptake of non-endogenous (i.e., exogenous or foreign) DNA by a cell. Transfection can be either transient transfection (i.e., the introduced DNA remains extrachromosomal and is diluted out during cell division) or stable transfection (i.e., the introduced DNA integrates into the cell genome or is maintained as a stable episomal element).

The term "biologically active" or "functional," when used herein as a modifier of human CRBN, refers to a polypeptide that exhibits at least one of the functional characteristics attributed to native human CRBN, such as the ability to form an E3 ubiquitin-ligase complex and mediates the ubiquitination and subsequent proteasomal degradation of target proteins.

The term "knockout" of a gene means an alteration in the sequence of the gene that results in a decrease in the expression and/or function of the target gene, preferably the target gene expression is undetectable or insignificant. A knockout of an endogenous gene means that the expression and/or function of the gene has been substantially decreased so that it is not detectable or only present at insignificant levels. "Knockout" transgenics can be transgenic animals having a heterozygous knockout of a gene or a homozygous knockout of a gene. "Knockouts" also include conditional knockouts, where alteration of the target gene can occur upon satisfaction of certain conditions, such as, exposure of the animal to a substance that promotes target gene alteration, introduction of an enzyme that promotes recombination at the target gene site (e.g., Cre in the Cre-lox system), or other conditions that direct the target gene alteration postnatally.

The term "knockin" of a target gene means an alteration in a host cell genome that results in altered (e.g., increased (including ectopic)) expression of the target gene, e.g., by introduction of one or more copies of the target gene, or by operatively inserting a regulatory sequence that enhances expression of the target gene. The target gene may be endogenous or non-endogenous. "Knockin" transgenic animals of interest for the present invention are transgenic animals having a knockin of a human or humanized CRBN or a fragment thereof. Such transgenic animals can be heterozygous knockin for the human or humanized CRBN gene or homozygous for the knockin of the human or humanized CRBN gene. Similarly to conditional "knockouts," "knockins" also encompass conditional knock-ins, where altered expression of the target gene can occur upon satisfaction of certain conditions.

The term "construct" refers to a recombinant nucleic acid, generally recombinant DNA, that has been generated for the purpose of the expression of a specific nucleotide sequence, or is to be used in the construction of other recombinant nucleotide sequences.

The term "vector" refers to a nucleic acid assembly capable of transferring gene sequences to target cells (e.g., viral vectors, non-viral vectors, particulate carriers, and liposomes). The term "expression vector" refers to a nucleic acid assembly containing a promoter that is capable of directing the expression of a sequence or gene of interest in a cell. As used interchangeably herein, "vector construct," "expression vector," "expression construct," and "gene transfer vector," refer to any nucleic acid construct capable of transferring a gene sequence to target cells and directing the expression of the gene in target cells. Thus, the term includes cloning and expression vehicles, as well as viral vectors.

The terms "promoter element" and "promoter," as used interchangeably herein, refer to a DNA regulatory sequence capable of binding an RNA polymerase in a cell (e.g., directly or through other promoter-bound proteins or substances) and initiating transcription of a coding sequence. The promoter may be operably associated with other expression control sequences, including enhancer and repressor sequences.

The term "operably linked" means that a DNA sequence encoding a target gene and a DNA regulatory sequence (e.g., promoter) are connected in such a way as to permit expression of the target gene when appropriate molecules (e.g., transcription factors) bind to the regulatory sequence.

The term "corresponds to" or "corresponding to" refer to homologous to, substantially equivalent to, or functionally equivalent to the designated sequence.

The term "transgenic construct," "transgenic gene construct," or "targeting construct" refers to a nucleic acid molecule, containing the subject polynucleotide, e.g., the human CRBN polynucleotide or a fragment thereof, which can be introduced into a host cell and is capable of expressing the polynucleotide in the host cell.

The terms "nucleic acid," "oligonucleotide," and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The terms "peptide," "polypeptide," and "protein," as used interchangeably herein, refer to a polymer of three or more amino acids in a serial array, linked through peptide bonds. The term "polypeptide" includes proteins, protein fragments, protein analogues, oligopeptides, and the like. The term "polypeptide" as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., glycopolypeptides, glycoproteins, or glycopeptides; or lipopolypeptides, lipoproteins, or lipopeptides.

The term "a cell" or "cells" refers not only to the particular subject cell, but to the progeny or potential progeny of such cell(s). The scope of the term as used herein encompasses the progeny that may not in fact be identical to the parent cell because certain modifications may occur in succeeding generations due to either mutation or environmental influences.

As used herein, the terms "cancer" and "cancerous" refer to or describe the physiological condition in mammals that is typically characterized by unregulated cell growth. Examples of cancer include, but are not limited to, blood-borne cancers (e.g., multiple myeloma, lymphoma and leukemia), and solid cancers. The term "cancer" refers to disease of tissues or organs, including but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, skin, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

As used herein, and unless otherwise specified, the terms "treat," "treating," and "treatment" refer to an action that occurs while a patient is suffering from a specified disease, which reduces the severity of the disease or retards or slows the progression of the disease.

As used interchangeably herein, the terms "compound" and "treatment compound" include a molecule in any pharmaceutically acceptable form, including a stereoisomer or a mixture of stereoisomers, tautomer, pharmaceutically acceptable salt, solvate, isotopologue, prodrug, hydrate, co-crystal, clathrate, or a polymorph thereof. In particular, if a compound is optically active, reference to the compound can include each of the compound's enantiomers as well as racemic mixtures of the enantiomers.

The term "CRBN E3 ubiquitin ligase modulating compound" or "CMC" refers to a molecule that directly or indirectly modulating the CRBN E3 ubiquitin ligase complex. In some embodiments, the CMC can bind directly to CRBN and induce conformational change in the CRBN protein. In other embodiments, the CMC can bind directly to other subunits in the CRBN E3 ubiquitin ligase complex.

The term "immunomodulatory compound" refers to a molecule that has immunomodulatory activity, i.e., modulating immune or inflammatory responses, in vitro (e.g., in an isolated cell, cell line, tissue, or organ) or in vivo (e.g., in an animal). Non-limiting examples of immunomodulatory compounds include thalidomide, lenalidomide, pomalidomide.

A "biological marker" or "biomarker" is a substance whose detection indicates a particular biological state, such as, for example, the presence of a disease. In some embodiments, biomarkers can be determined individually. In other embodiments, several biomarkers can be measured simultaneously. In some embodiments, a "biomarker" indicates a change in the level of mRNA expression that may correlate with the risk or progression of a disease, or with the susceptibility of the disease to a given treatment. In some embodiments, the biomarker is a nucleic acid, such as mRNA or cDNA. The relative level of nucleic acids can be determined by methods known in the art. For example, northern blot, RT-PCR, or other methods can be used. In additional embodiments, a "biomarker" indicates a change in the level of polypeptide or protein expression that may correlate with the risk or progression of a disease, or patient's susceptibility to treatment. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

The term "antibody," "immunoglobulin," or "Ig" as used interchangeably herein, encompasses fully assembled antibodies and antibody fragments that retain the ability to specifically bind to the antigen. Antibodies provided herein include, but are not limited to, synthetic antibodies, monoclonal antibodies, polyclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to CRBN antigen (e.g., one or more complementarity determining regions (CDRs) of an anti-CRBN antibody). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. In some embodiments, the anti-CRBN antibodies are fully human, such as fully human monoclonal CRBN antibodies. In certain embodiments, antibodies provided herein are IgG antibodies, or a subclass thereof (e.g., human IgG1 or IgG4).

The term "expressed" or "expression" as used herein refers to the transcription from a gene (e.g., a DNA sequence encoding the gene) to yield a messenger RNA (mRNA) molecule at least complementary in part to a region of one of the two nucleic acid strands of the gene. The term "expressed" or "expression" as used herein also refers to the translation from the mRNA molecule to produce a protein, a polypeptide, or a portion thereof.

The term "level" refers to the amount, accumulation, or rate of a biomarker molecule. A level can be represented, for example, by the amount or the rate of synthesis of an mRNA encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Assessing the presence of" can include determining the amount of something present, as well as determining whether it is present or absent.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g., if they produce a given or detectable level of signal in a hybridization assay. Portions of polynucleotides are complementary to each other if they follow conventional base-pairing rules, e.g., A pairs with T (or U) and G pairs with C, although small regions (e.g., fewer than about 3 bases) of mismatch, insertion, or deleted sequence may be present.

"Sequence identity" or "identity" in the context of two nucleic acid sequences refers to the residues in the two sequences that are the same when aligned for maximum correspondence over a specified comparison window, and can take into consideration of additions, deletions, and substitutions. Those skilled in the art can determine appropriate parameters for aligning sequences, including any algorithms needed to achieve maximal alignment over the full length of the sequences being compared.

The term "substantial identity" or "homologous" in their various grammatical forms in the context of polynucleotides generally means that a polynucleotide comprises a sequence that has a desired identity, for example, at least 60% identity, at least 70% identity, at least 80% identity, at least 90% identity, at least 95% identity, or at least 99% identity as compared to a reference sequence. Another indication that nucleotide sequences are substantially identical is if two molecules hybridize to each other under stringent conditions.

The terms "isolated" and "purified," when used with a substance (such as mRNA, DNA, or protein), refer to isolation of the substance (such as mRNA, DNA, or protein) such that the substance comprises a substantial portion of the sample in which it resides, i.e., greater than the portion of the substance that is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

As used herein, the term "bound" indicates direct or indirect attachment. In the context of chemical structures, "bound" (or "bonded") may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and embodiments where the attachment is indirect.

The term "sample" as used herein relates to a material or mixture of materials, typically, although not necessarily, in fluid form, containing one or more components of interest. A "sample" can be a biological sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include, but are not limited to, whole blood, partially purified blood, PBMC, tissue biopsies, and the like.

The term "polymerase chain reaction" or "PCR" as used herein generally refers to a procedure wherein small amounts of a nucleic acid, RNA and/or DNA, are amplified as described, for example, in U.S. Pat. No. 4,683,195. Generally, sequence information from the ends or beyond of the region of interest needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 1987, 51:263-273; *PCR Technology* (Stockton Press, NY, Erlich, ed., 1989).

"Tautomer" as used herein refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

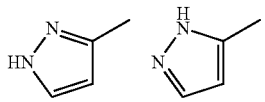

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like. Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts (calcium, magnesium, sodium, or potassium salts in particular). Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof that further includes a stoichiometric or non-stoichiometric amount of solvent bound by non-covalent intermolecular forces. Where the solvent is water, the solvate is a hydrate.

As used herein and unless otherwise indicated, the term "co-crystal" means a crystalline form that contains more than one compound in a crystal lattice. Co-crystals include crystalline molecular complexes of two or more non-volatile compounds bound together in a crystal lattice through non-ionic interactions. As used herein, co-crystals include pharmaceutical co-crystals wherein the crystalline molecular complexes containing a therapeutic compound and one or more additional non-volatile compound(s) (referred to herein as counter-molecule(s)). A counter-molecule in a pharmaceutical co-crystal is typically a non-toxic pharmaceutically acceptable molecule, such as, for example, food additives, preservatives, pharmaceutical excipients, or other active pharmaceutical ingredients (API). In some embodiments, pharmaceutical co-crystals enhance certain physico-chemical properties of drug products (e.g., solubility, dissolution rate, bioavailability, and/or stability) without compromising the chemical structural integrity of the API. See, e.g., Jones et al., *MRS Bulletin* 2006, 31,875-879; Trask, *Mol. Pharmaceutics* 2007, 4(3):301-309; Schultheiss & Newman, *Crystal Growth & Design* 2009, 9(6):2950-2967; Shan & Zaworotko, *Drug Discovery Today* 2008, 13(9/10):440-446; and Vishweshwar et al., *J. Pharm. Sci.* 2006, 95(3):499-516.

As used herein, and unless otherwise specified, the term "stereoisomer" encompasses all enantiomerically/stereomerically pure and enantiomerically/stereomerically enriched compounds of this invention.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises, within measurement error, greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, even more preferably greater than about 97% by weight of one stereoisomer of the compound and less than about 3% by weight of the other stereoisomers of the compound, even more preferably greater than about 99% by weight of one stereoisomer of the compound and less than about 1% by weight of the other stereoisomers of the compound, even more preferably greater than about 99.9% by weight of one stereoisomer of the compound and less than about 0.1% by weight of the other stereoisomers of the compound, and most preferably about 100% by weight of one stereoisomer of the compound and about 0% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff, ed., 5th ed. 1995), and *Design of Prodrugs* (H. Bundgaard, ed., Elsevier, New York 1985).

It should also be noted compounds can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues are deuterium, carbon-13, or nitrogen-15 enriched compounds. In some embodiments, isotopologues provided herein are deuterium enriched compounds. In some embodiments, isotopologues provided herein are deuterium enriched compounds, where the deuteration occurs on the chiral center. In some embodiments, provided herein are isotopologues of the compounds of Formula I, where deuteration occurs on the chiral center. In some embodiments, provided herein are isotopologues of Compound C, where deuteration occurs on the chiral center.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning: A Laboratory Manual* (2d ed. 1989); Glover, ed., *DNA Cloning*, Volumes I and II (1985); Gait, ed., *Oligonucleotide Synthesis* (1984); Hames & Higgins, eds., *Nucleic Acid Hybridization* (1984); Hames & Higgins, eds., *Transcription and Translation* (1984); Freshney, ed., *Animal Cell Culture: Immobilized Cells and Enzymes* (IRL Press, 1986); *Immunochemical Methods in Cell and Molecular Biology* (Academic Press, London); Scopes, *Protein Purification: Principles and Practice* (Springer Verlag, N.Y., 2d ed. 1987); and Weir & Blackwell, eds., *Handbook of Experimental Immunology*, Volumes I-IV (1986).

5.2 Transgenic Mouse Expressing Human CRBN

In certain embodiments, the transgenic animals are transgenic non-human mammals, e.g., cows, pigs, goats, horses, rodents (such as, rats, mice, or hamsters), etc. In some embodiments, the transgenic animals are transgenic rodents, e.g., rats, mice, hamsters, etc. In specific embodiments, the transgenic animals are transgenic mice.

Transgenic animals contain an exogenous nucleic acid sequence as either an extrachromosomal element or stably integrated in all or a portion of its cells (e.g., somatic cells and/or germ cells). In certain embodiments, the exogenous nucleic acid sequence exists as an extrachromosomal element (e.g., minichromosome, bacterial artificial chromosome (BAC), yeast artificial chromosomes (YAC)) in the transgenic animals. In other embodiments, the exogenous nucleic acid sequence is stably integrated in the genome of the transgenic animals. In some embodiments, the exogenous nucleic acid sequence exists in all the cells of the transgenic animals, including somatic cells and germ cells. In other embodiments, the exogenous nucleic acid sequence exists in a portion of the cells of the transgenic animals, including a portion of somatic cells and/or a portion of germ cells. In certain embodiments, a transgenic animal comprises stable changes to the germline sequence, i.e., the exogenous nucleic acid sequence stably integrated in the genome of germ cells.

During the initial construction of transgenic animals, "chimeras" or "chimeric animals" are generated, in which only a subset of cells have the altered genome. Chimeras are primarily used for breeding to generate transgenic animals with germline transmission, i.e., transgenic animals with an exogenous nucleic acid sequence stably integrated in the genome of germ cells. Animals having a germline heterozygous alteration are produced by breeding of chimeras. Male and female heterozygotes with germline transmission are then bred to produce homozygous transgenic animals. Homozygous transgenic animals can further be bred with animals of different genetic backgrounds (e.g., xenograft animal model, various disease animal models, or transgenic animals with different transgenes) to produce transgenic animals with the particular genetic backgrounds. Thus, in some embodiments, the transgenic animals are chimeric transgenic animals. In certain embodiments, the transgenic animals are heterozygous transgenic animals. In other embodiments, the transgenic animals are homozygous transgenic animals. In yet other embodiments, the transgenic animals are homozygous transgenic animals with particular genetic backgrounds (e.g., xenograft animal model, various disease animal models, or transgenic animals with different transgenes).

In certain embodiments, the transgenic animals are produced by introducing a human CRBN gene or a fragment thereof into the germline of the non-human animal (e.g., mouse). In some embodiments, the transgenic animals are transgenic mice, produced by introducing a human CRBN gene or a fragment thereof into the germline of mice. In one embodiment, the human CRBN gene may be of natural or artificial origin. In another embodiment, the human CRBN gene may be genomic DNA, complementary DNA (cDNA), hybrid sequences, synthetic sequences, or semi-synthetic sequences.

In certain embodiments, the transgenic mice are produced by introducing a human CRBN cDNA or a fragment thereof into the germline of mice. In yet other embodiments, the transgenic mice are produced by introducing a full-length human CRBN cDNA (e.g., human CRBN isoform 1 or human CRBN isoform 2) into the germline of the transgenic mice. In one embodiment, the transgenic mice are produced by introducing a full-length human CRBN isoform 1 cDNA into the germline of the transgenic mice, wherein the full-length human CRBN isoform 1 cDNA has a nucleic acid sequence as follows:

```
                                             (SEQ ID NO: 5)
atggccggcg aaggagatca gcaggacgct gcgcacaaca tgggcaacca cctgccgctc ctgcctgcag agagtgagga agaagatgaa atggaagttg aagaccagga tagtaaagaa gccaaaaaac caaacatcat aaattttgac accagtctgc cgacatcaca tacataccta ggtgctgata tggaagaatt tcatggcagg actttgcacg atgacgacag ctgtcaggtg attccagttc ttccacaagt gatgatgatc ctgattcccg gacagacatt acctcttcag cttttttcacc ctcaagaagt cagtatggtg cggaatttaa ttcagaaaga tagaaccttt gctgttcttg catacagcaa tgtacaggaa agggaagcac agtttggaac aacagcagag atatatgcct atcgagaaga acaggatttt ggaattgaga tagtgaaagt gaaagcaatt ggaagacaaa ggttcaaagt ccttgagcta agaacacagt cagatggaat ccagcaagct aaagtgcaaa ttcttcccga atgtgtgttg ccttcaacca tgtctgcagt tcaattagaa tccctcaata agtgccagat atttccttca aaacctgtct caagagaaga ccaatgttca tataaatggt ggcagaaata ccagaagaga agtttcatt gtgcaaatct aacttcatgg cctcgctggc tgtattcctt atatgatgct gagaccttaa tggacagaat caagaaacag ctacgtgaat gggatgaaaa tctaaaagat gattctcttc cttcaaatcc aatagatttt tcttacagag tagctgcttg tcttcctatt gatgatgtat tgagaattca gctccttaaa attggcagtg ctatccagcg acttcgctgt gaattagaca ttatgaataa atgtacttcc ctttgctgta aacaatgtca agaaacagaa ataacaacca aaaatgaaat attcagttta tccttatgtg ggccgatggc agcttatgtg aatcctcatg gatatgtgca tgagacactt actgtgtata aggcttgcaa cttgaatctg ataggccggc
```

In some embodiments, the full-length human CRBN isoform 1 cDNA is stably integrated into a mouse chromosome.

In another embodiment, the transgenic mice are produced by introducing a full-length human CRBN isoform 2 cDNA into the germline of the transgenic mice, wherein the full-length human CRBN isoform 2 cDNA has a nucleic acid sequence as follows:

```
                                             (SEQ ID NO: 6)
atggccggcg aaggagatca gcaggacgct gcgcacaaca tgggcaacca cctgccgctc ctgcctgaga gtgaggaaga agatgaaatg gaagttgaag accaggatag taaagaagcc aaaaaaccaa acatcataaa ttttgacacc agtctgccga catcacatac atacctaggt gctgatatgg aagaatttca tggcaggact ttgcacgatg acgacagctg tcaggtgatt ccagttcttc cacaagtgat gatgatcctg attcccggac agacattacc tcttcagctt tttcaccctc aagaagtcag tatggtgcgg aatttaattc agaaagatag aacctttgct gttcttgcat acagcaatgt acaggaaagg gaagcacagt ttggaacaac agcagagata tatgcctatc gagaagaaca ggattttgga attgagatag tgaaagtgaa agcaattgga agacaaaggt tcaaagtcct tgagctaaga acacagtcag atggaatcca gcaagctaaa gtgcaaattc ttcccgaatg tgtgttgcct tcaaccatgt ctgcagttca attagaatcc ctcaataagt gccagatatt tccttcaaaa cctgtctcaa gagaagacca atgttcatat aaatggtggc agaaatacca agagagaaag tttcattgtg caaatctaac ttcatggcct cgctggctgt attccttata tgatgctgag accttaatgg acagaatcaa gaaacagcta cgtgaatggg atgaaaatct aaaagatgat tctcttcctt caaatccaat agattttct tacagagtag ctgcttgtct tcctattgat gatgtattga gaattcagct ccttaaaatt ggcagtgcta tccagcgact tcgctgtgaa ttagacatta tgaataaatg tacttccctt tgctgtaaac aatgtcaaga
```

```
aacagaaata acaaccaaaa atgaaatatt cagtttatcc ttatgtgggc cgatggcagc ttatgtgaat cctcatggat atgtgcatga gacacttact gtgtataagg cttgcaactt gaatctgata ggccggcctt ctacagaaca cagctggttt cctgggtatg cctggactgt tgcccagtgt aagatctgtg caagccatat tggatggaag tttacggcca ccaaaaaaga catgtcacct caaaaatttt ggggcttaac gcgatctgct ctgttgccca cgatcccaga cactgaagat gaaataagtc cagacaaagt aatactttgc ttgtaa.
```

In some embodiments, the full-length human CRBN isoform 2 cDNA is stably integrated into a mouse chromosome.

In other embodiments, the transgenic mice are produced by introducing a fragment of human CRBN cDNA (e.g., a fragment of human CRBN isoform 1 or a fragment of human CRBN isoform 2) into the germline of the transgenic mice. In a particular embodiment, the transgenic mice are produced by introducing a fragment of human CRBN isoform 1 cDNA into the germline of the transgenic mice. In another particular embodiment, the transgenic mice are produced by introducing a fragment of human CRBN isoform 2 cDNA into the germline of the transgenic mice. In some embodiments, the transgenic mice are produced by introducing into the germline of the transgenic mice a fragment of human CRBN cDNA that comprises a nucleic acid sequence encoding a portion of human CRBN isoform 1. In another embodiment, the transgenic mice are produced by introducing into the germline of the transgenic mice a fragment of human CRBN cDNA that comprises a nucleic acid sequence encoding a portion of human CRBN isoform 2. In other embodiments, the transgenic mice are produced by introducing into the germline of the transgenic mice a fragment of human CRBN isoform 1 cDNA comprising a nucleic acid sequence that starts at the nucleic acid sequence encoding codon 24 (Glutamate) of the human CRBN isoform 1 and ends at the stop codon of the human CRBN isoform 1. In yet other embodiments, the transgenic mice are produced by introducing into the germline of the transgenic mice a fragment of human CRBN isoform 2 cDNA comprising a nucleic acid sequence that starts at the nucleic acid sequence encoding codon 23 (Glutamate) of the human CRBN isoform 2 and ends at the stop codon of the human CRBN isoform 2. In yet other embodiments, the transgenic mice are produced by introducing into the germline of the transgenic mice a fragment of human CRBN cDNA (e.g., a fragment of human CRBN isoform 1 or a fragment of human CRBN isoform 2) that comprises a nucleic acid sequence as follows:

```
                                       (SEQ ID NO: 7)
ag agagtgagga agaagatgaa atggaagttg aagaccagga tagtaaagaa gccaaaaaac caaacatcat aaatttgac accagtctgc cgacatcaca tacataccta ggtgctgata tggaagaatt tcatggcagg actttgcacg atgacgacag ctgtcaggtg attccagttc ttccacaagt gatgatgatc ctgattcccg gacagacatt acctcttcag cttttcacc ctcaagaagt cagtatggtg cggaatttaa ttcagaaaga tagaaccttt gctgttcttg catacagcaa tgtacaggaa agggaagcac agtttggaac aacagcagag atatatgcct atcgagaaga acaggatttt ggaattgaga tagtgaaagt gaaagcaatt ggaagacaaa ggttcaaagt ccttgagcta agaacacagt cagatggaat ccagcaagct aaagtgcaaa ttcttcccga atgtgtgttg ccttcaacca tgtctgcagt tcaattagaa tccctcaata agtgccagat atttccttca aaacctgtct caagagaaga ccaatgttca tataaatggt ggcagaaata ccagaagaga aagtttcatt gtgcaaatct aacttcatgg cctcgctggc tgtattcctt atatgatgct gagaccttaa tggacagaat caagaaacag ctacgtgaat gggatgaaaa tctaaaagat gattctcttc cttcaaatcc aatagatttt tcttacagag tagctgcttg tcttcctatt gatgatgtat tgagaattca gctccttaaa attggcagtg ctatccagcg acttcgctgt gaattagaca ttatgaataa atgtacttcc ctttgctgta aacaatgtca agaaacagaa ataacaacca aaaatgaaat attcagttta tccttatgtg ggccgatggc agcttatgtg aatcctcatg gatatgtgca tgagacactt actgtgtata aggcttgcaa cttgaatctg ataggccggc cttctacaga acacagctgg tttcctgggt atgcctggac tgttgcccag tgtaagatct gtgcaagcca tattggatgg aagtttacgg ccaccaaaaa agacatgtca cctcaaaaat tttggggctt aacgcgatct gctctgttgc ccacgatccc agacactgaa gatgaaataa gtccagacaa agtaatactt tgcttgtaa.
```

In some embodiments, a fragment of human CRBN isoform 1 cDNA is stably integrated into a mouse chromosome. In other embodiments, a fragment of human CRBN isoform 2 cDNA is stably integrated into a mouse chromosome.

In yet another embodiment, the transgenic mice are produced by introducing a fragment of human CRBN cDNA (e.g., a fragment of human CRBN isoform 1 or a fragment of human CRBN isoform 2) into the germline of the transgenic mice through homologous recombination between the mouse CRBN genomic DNA and a target construct comprising a fragment of human CRBN cDNA (e.g., a fragment of human CRBN isoform 1 or a fragment of human CRBN isoform 2). In a specific embodiment, the targeting construct comprises a nucleic acid sequence as follows:

(SEQ ID NO: 8)

aagaacagctcacacttgatagaataccacttctagaaa
gtagcgttgtgttttgtttcttcagactttcatctctg
cccttggcagcatcatgttatcaggtggatcagcttagc
tttcatttcatttcaaaaaaaaagtgcaggtagagtt
cttaagatatctcctttgccaggcagtggtggcgcact
cctttaatcccagcacttgggaggcagaggcaggcaga
tttctgagttcgaggccagcctggtctacagagtgagtt
ccaggacagccagggctacatagagaaaccctgtctcc
aaaaactcgaaaaacagaaaagaaagaaaaaaaaaa
gacatctcctttaaaatgtattttctttgggccaactt
tattttaaattgagaatgacaaagcgatgttttatgaa
aaataattgcaaacatttcacgtttaaatatgacggtg
agccaggttttaatggtatttttttcccagtttcatta
acagacctttcttgcctgcttgtgttttccttgctttc
tttttcacagagaaactttgtagctaaagtctgaaagaa
cctcatagattactttgttcaagccttcattgtttttt
tttcaaatgaaaaaacagctttaatcaattggaattca
ttgtgtaaggtgtcaggattagtagtgatggagaagat
aagactcatccatgcaggagatgggcctaattcagccac
gtcagtcgttaggctggacctagtgatctgctttccaa
ccgtgtacggtgtaactgcggggcaggggcgagggggtt
tacagagaaggaagctggcggctgtttctgaccagaaa
tcaaggggaacatcagcccctgggtcaggctgactgtac
gtacccttgatgtgcggtgaggaataggcgttgtccct
agcagaactctaatagagaatgacatctattccctattg
agggatgctgtgtaaagtcctgataaggaagacagaac
atccagcatgcgtgtaccacaggcagcaaggagccata
cctaaatatagcatggtgtcctggaggggtaacaggaa
atggagaatagctgaaaatcaaaggcaatccaaataaga
taaggcatttagttaacagtaatgtgccaatatcgacg
acttagttgtcacaagaataccagatgcatggaccatgc
taacaatggaggaagatagtcttggcatgctagaattc
tattttccaacattccaggaaatcttaaagtgtcctaa
gatagttgattgttaaaaacagggaaaaagaaaggaa
aggaaaagaaaggaaaggcgccatgacagaaagagcac
agacccagcctctgccgctgtctctgcacagctttcct
tttaagagtgtctttcttcaattcagggtgtgtgaatgg
aaccagaactgacttgcttttttcttttcttttttttt
tttttaatgaatctcattttttccctctattattctcc
ttcagcagagagtgaggaagaagatgaaatggaagttg -continued aagaccaggatagtaaagaagccaaaaaaccaaacatca
taaattttgacaccagtctgccgacatcacatacatac
ctaggtgctgatatggaagaatttcatggcaggactttg
cacgatgacgacagctgtcaggtgattccagttcttcc
acaagtgatgatgatcctgattcccggacagacattacc
tcttcagcttttcaccctcaagaagtcagtatggtgc
ggaatttaattcagaaagatagaacctttgctgttcttg
catacagcaatgtacaggaaagggaagcacagtttgga
acaacagcagagatatatgcctatcgagaagaacaggat
tttggaattgagatagtgaaagtgaaagcaattggaag
acaaaggttcaaagtccttgagctaagaacacagtcaga
tggaatccagcaagctaaagtgcaaattcttcccgaat
gtgtgttgccttcaaccatgtctgcagttcaattagaat
ccctcaataagtgccagatatttccttcaaaacctgtc
tcaagagaagaccaatgttcatataaatggtggcagaaa
taccagaagagaaagtttcattgtgcaaatctaacttc
atggcctcgctggctgtattccttatatgatgctgagac
cttaatggacagaatcaagaaacagctacgtgaatggg
atgaaaatctaaaagatgattctcttccttcaaatccaa
tagattttcttacagagtagctgcttgtcttcctatt
gatgatgtattgagaattcagctccttaaaattggcagt
gctatccagcgacttcgctgtgaattagacattatgaa
taaatgtacttcccttttgctgtaaacaatgtcaagaaac
agaaataacaaccaaaaatgaaatattcagtttatcct
tatgtgggccgatggcagcttatgtgaatcctcatggat
atgtgcatgagacacttactgtgtataaggcttgcaac
ttgaatctgataggccggccttctacagaacacagctgg
tttcctgggtatgcctggactgttgccagtgtaagat
ctgtgcaagccatattggatggaagtttacggccaccaa
aaaagacatgtcacctcaaaaattttgggcttaacgc
gatctgctctgttgcccacgatcccagacactgaagatg
aaataagtccagacaaagtaatactttgcttgtaagtg
cacctagagctcgctgatcagcctcgactgtgccttcta
gttgccagccatctgttgtttgcccctccccgtgcct
tccttgaccctggaaggtgccactcccactgtcctttcc
taataaaatgaggaaattgcatcgcattgtctgagtag
gtgtcattctattctgggggtggggtggggcaggacag
caaggggaggattgggaagacaatagcaggcatgctg
gggatgcggtgggctctatggcttctgaggcggaaagaa
ccagctggggctcgactagagcttgcggaacccttcgt
atgtggtttagtcattgagcaaatgcagtatgcggacct -continued ttatctatggctggaatttggtaccttttgctagcata
acttcgtatagcatacattatacgaagttatcctaggta
attctaccgggtaggggaggcgcttttcccaaggcagt
ctggagcatgcgctttagcagcccgctgggcacttggc
gctacacaagtggcctctggcctcgcacacattccaca
tccaccggtaggcgccaaccggctccgttctttggtggc
cccttcgcgccaccttctactcctcccctagtcaggaa
gttccccccgcccgcagctcgcgtcgtgcaggacgtg
acaaatggaagtagcacgtctcactagtctcgtgcaga
tggacagcaccgctgagcaatggaagcgggtaggccttt
ggggcagcggccaatagcagctttgctccttcgctttc
tgggctcagaggctgggaaggggtgggtccggggcggg
ctcaggggcgggctcaggggcggggcgggcgcccgaag
gtcctccggaggcccggcattctgcacgcttcaaaagcg
cacgtctgccgcgctgttctcctcttcctcatctccgg
gcctttcgacctgcagcctgttgacaattaatcatcggc
atagtatatcggcatagtataatacgacaaggtgagga
actaaaccagatctgccaccatgattgaacaagatggat
tgcacgcaggttctccggccgcttgggtggagaggcta
ttcggctatgactgggcacaacagacaatcggctgctct
gatgccgccgtgttccggctgtcagcgcaggggcgccc
ggttcttttttgtcaagaccgacctgtccggtgccctgaa
tgaactgcaggacgaggcagcgcggctatcgtggctgg
ccacgacgggcgttccttgcgcagctgtgctcgacgttg
tcactgaagcgggaagggactggctgctattgggcgaa
gtgccggggcaggatctcctgtcatctcaccttgctcct
gccgagaaagtatccatcatggctgatgcaatgcggcg
gctgcatacgcttgatccggctacctgcccattcgacca
ccaagcgaaacatcgcatcgagcgagcacgtactcgga
tggaagccggtcttgtcgatcaggatgatctggacgaag
agcatcaggggctcgcgccagccgaactgttcgccagg
ctcaaggcgcgcatgcccgacggcgaggatctcgtcgtg
acccatggcgatgcctgcttgccgaatatcatggtgga
aaatggccgcttttctggattcatcgactgtggccggct
gggtgtggcggaccgctatcaggacatagcgttggcta
cccgtgatattgctgaagagcttggcggcgaatgggctg
accgcttcctcgtgctttacggtatcgccgctcccgat
tcgcagcgcatcgccttctatcgccttcttgacgagttc
ttctgacttaagaacttgtttattgcagcttataatgg
ttacaaataaagcaatagcatcacaaatttcacaaataa -continued agcatttttttcactgcattctagttgtggtttgtcca
aactcatcaatgtatcttatcatgtctgcaattgataac
ttcgtatagcatacattatacgaagttatgaattctttt
tctcgagcctaagtgcagggagccacactaggggactag
tgcaggggactgactagagggttcctgcatattcgctg
accctagaatccgtgcatgagaacagacttattttccag
tgcatagcatgtaattttagaaatggaagccgtgtcgt
actatatcctcatgtgattcttgactattttctaatatg
taagctgatatgtaaacattaaagctaacatatagctt
tatgtttaaacttatcttggagggactctttgaggaat
tgtcttcctctgaaggggtctgctagtaactgagccat
taagtgttcttaatgttgtttcagaactgctgggatgtg
gggcggtattataggtactaaaattctgtcctatgctt
tgtcagttttggacatagaggagttttggtgaaaatatt
ttgaattacaaaataatgatcgattcttgataaaaatt
gggagttctaataggaaatactagatcaaaaattagagt
ttgatggaggcatgcttatataacagattatttaaata
aacatgtgctctgtttagtgttttcctctgctttattct
ttagtaggttgacgtgtagtaagtgtgtgtcttgactc
tgtgctcttgagtagtacctgggagctgatatggaggag
ttccacgggagaactttgcatgacgacgacagctgcca
ggtgatcccagtccttcctgaggtgctgatgatcctgat
tcctgggcagacactcccactgcagctctctcacccac
aggaagtcagcatggtgcggaacttaatccagaaagaca
ggacctttgcagtccttgcatacaggtaagagattaga
cagatctgcttaccaccctgccaaagtcagtgcgacagc
taaagccaacggggatttgcagatactggacaggagtg
tgaagcaaacggtcttgtgtcacattttcagtgtttcgc
tgttttttacagtgtagctgtgtttggctcttgaaaaac
ttccactcacttaatggaaaacctccctgttcagaactg
tctttatttaaaaatagctaagttttaaaatttttcaat
aaaggttacttttctaaagtgaagctgttcttcagtagc
ctgtggcaaatgagggaaccgtggtggaggcaggaaat
ggaaacaggaaacctcccatcacccccgctgaccctccc
ctcagacagtcacagtgctgccagttagtgcgaccatc
attgcctgccaaagtgaaaggatgctcattttgtgaaat
aacgatttaaaacttcttagcactggttatctcagtga
agcctaaaagtctacctttattctaaaatatgctgtttg
ccttccggggccttgtgtgtcagcttcctagtgagggt
tagctgctgtaattgtcacagtgtttgcccgatctgtgt
cgcttttgccacctttacataattatgagccagagctg -continued

```
aaaactctgtccattttttgtctttgaagtaatgtgcaag
aaaggg.
```

In some embodiments, the targeting construct is stably integrated into a mouse chromosome.

In some embodiments, the transgenic mice are produced by introducing a variant (e.g., mutation, deletion, or insertion) of human CRBN gene or a fragment thereof into the germline of mice. In one embodiment, the transgenic mice are produced by introducing human CRBN gene or a fragment thereof that contains mutation into the germline of mice. In another embodiment, the transgenic mice are produced by introducing human CRBN gene or a fragment thereof that contains deletion into the germline of mice. In yet another embodiment, the transgenic mice are produced by introducing human CRBN gene or a fragment thereof that contains insertion into the germline of mice. In still another embodiment, the transgenic mice are produced by introducing human CRBN gene or a fragment thereof that contains mutation, deletion, and/or insertion into the germline of mice. In some embodiments, the transgenic mice are produced by introducing human CRBN gene or a fragment thereof that contains mutation and deletion into the germline of mice. In certain embodiments, the transgenic mice are produced by introducing human CRBN gene or a fragment thereof that contains mutation and insertion into the germline of mice. In other embodiments, the transgenic mice are produced by introducing human CRBN gene or a fragment thereof that contains deletion and insertion into the germline of mice. In yet other embodiments, the transgenic mice are produced by introducing human CRBN gene or a fragment thereof that contains mutation, deletion, and insertion into the germline of mice.

In certain embodiments, the transgenic mice are produced by introducing a variant (e.g., mutation, deletion, or insertion) of human CRBN gene or a fragment thereof that has at least about 50, 60, 70, 80, 90, or 95% identity to the wild-type human CRBN gene into the germline of mice. In certain embodiments, the transgenic mice are produced by introducing a variant (e.g., mutation, deletion, or insertion) of human CRBN gene or a fragment thereof that has at least about 90, 91, 92, 93, 94, 95, 96, 97, 98, or 99% identity to the wild-type human CRBN gene into the germline of mice. In certain embodiments, the transgenic mice are produced by introducing a variant (e.g., mutation, deletion, or insertion) of human CRBN gene or a fragment thereof that has about 90, 91, 92, 93, 94, 95, 96, 97, 98, or 99% identity to the wild-type human CRBN gene into the germline of mice.

The variants of human CRBN gene or a fragment thereof comprise homologous hCRBN amino acid sequences having one or more mutations, deletions, and/or insertions, as long as the required level of sequence identity across the full length or the fragment thereof of hCRBN is achieved. Sequence identity can be determined using known programs such as BLAST, ALIGN, and CLUSTAL using standard parameters. See, e.g., Altschul et al., *J. Mol. Biol.* 1990, 215:403-410; Henikoff et al., *Proc. Natl. Acad. Sci. USA* 1989, 89:10915; Karin et al., *Proc. Natl. Acad. Sci. USA* 1993, 90:5873; Higgins et al., *Gene* 1988, 73:237-244. Software for performing BLAST analyses is publicly available through the National Center for Biotechnology Information. Databases may also be searched using FASTA. See Pearson et al., *Proc. Natl. Acad. Sci. USA* 1988, 85:2444-2448.

In certain embodiments, the hCRBN transgenic animal comprises one or more copies of the nucleotide sequence encoding human CRBN or a fragment thereof. In some embodiments, the hCRBN transgenic animal comprises more than about 1, more than about 2, more than about 3, more than about 4, more than about 5, more than about 6, more than about 7, more than about 8, more than about 9, more than about 10, more than about 11, more than about 12, more than about 13, more than about 14, or more than about 15 copies of the nucleotide sequence encoding human CRBN or a fragment thereof. In other embodiments, the hCRBN transgenic animal comprises about 1, about 2, about 3, about 4, about 5, about 6, about 7, about 8, about 9, about 10, about 11, about 12, about 13, about 14, or about 15 copies of the nucleotide sequence encoding human CRBN or a fragment thereof. For example, provided herein are transgenic animals comprising a nucleotide sequence encoding human CRBN or a fragment thereof, wherein the human CRBN is expressed in the transgenic animal, wherein the hCRBN transgenic animal comprises about 1 to about 2 copies of the nucleotide sequence encoding human CRBN.

In certain embodiments, the hCRBN transgenic animal expresses different levels of human CRBN. In some embodiments, the levels of human CRBN expression are directly or indirectly determined by the copy number of hCRBN gene, the genomic site where the nucleic acid sequence encoding hCRBN is integrated, and/or the promoter and/or regulatory regions operably linked to the nucleic acid sequence encoding hCRBN. In certain embodiments, the nucleic acid sequence encoding hCRBN is integrated into a chromosome or a locus that is different from the chromosome or the locus where endogenous CRBN gene is located. In other embodiments, the nucleic acid sequence encoding hCRBN is integrated into a chromosome or a locus that is the same chromosome or the same locus where endogenous CRBN gene is located. In some embodiments, the nucleic acid sequence encoding hCRBN is integrated into the endogenous CRBN gene and disrupts the expression of the endogenous CRBN gene.

In certain embodiments, the promoter and/or regulatory regions are homologous (e.g., mouse promoter and/or regulatory regions for a transgenic mouse). In one embodiment, the promoter is homologous. In another embodiment, the regulatory regions are homologous. In yet another embodiment, the promoter and the regulatory regions are homologous. In one particular embodiment, the promoter is homologous mouse CRBN promoter. In another embodiment, the regulatory regions are homologous mouse CRBN regulatory regions. In yet another embodiment, the promoter and the regulatory regions are homologous mouse CRBN promoter and regulatory regions. In some embodiments, the promoter and/or regulatory regions are heterologous (e.g., non-mouse eukaryotic, bacterial, or viral promoter and/or regulatory regions in a transgenic mouse). In one embodiment, the promoter is heterologous. In another embodiment, the regulatory regions are heterologous. In yet another embodiment, the promoter and the regulatory regions are heterologous. Non-limiting examples of viral promoters that are commonly used include adenovirus EIA promoter, adenovirus major late promoter (MLP), human cytomegalovirus (HCMV) promoter, and Rous sarcoma virus (RSV) promoters and the like. Promoters can be constitutive or regulated (e.g., induced or repressed). Regulatory regions may be used to regulate (e.g., increase or decrease) the expression level of CRBN or to designate the expression of CRBN to specific tissues or to certain stages of development. In some embodiments, the regulatory region increases expression of CRBN. In other embodiments, the regulatory region decreases expression of CRBN. In yet other embodiments, the regulatory region designates the expression of CRBN to specific tissues or to certain stages of development. In certain embodiments, the regulatory regions comprise a 5' region for functional transcription of a gene of interest, and a region situated 3' of the gene of interest, which specifies a signal for termination of transcription and a poly(A) site.

In some embodiments of transgenic mice, the expression of human CRBN is controlled by heterologous (e.g., non-mouse eukaryotic, bacterial, or viral) promoter and/or regulatory regions. In one embodiment, the expression of human CRBN is controlled by heterologous promoter. In one embodiment, the expression of human CRBN is controlled by heterologous regulatory regions. In yet one embodiment, the expression of human CRBN is controlled by heterologous promoter and regulatory regions. In certain embodiments, the expression of human CRBN is controlled by non-mouse eukaryotic (e.g., human, monkey, rat, etc.) promoter and/or regulatory regions. In one embodiment, the expression of human CRBN is controlled by non-mouse eukaryotic promoter. In another embodiment, the expression of human CRBN is controlled by non-mouse eukaryotic regulatory regions. In yet another embodiment, the expression of human CRBN is controlled by non-mouse eukaryotic promoter and regulatory regions. In some embodiments, the expression of human CRBN is controlled by bacterial promoter and/or regulatory regions. In one embodiment, the expression of human CRBN is controlled by bacterial promoter. In another embodiment, the expression of human CRBN is controlled by bacterial regulatory regions. In yet another embodiment, the expression of human CRBN is controlled by bacterial promoter and regulatory regions. In some embodiments, the expression of human CRBN is controlled by viral (e.g., EIA, MLP, HCMV, RSV, etc.) promoter and/or regulatory regions. In one embodiment, the expression of human CRBN is controlled by viral promoter. In another embodiment, the expression of human CRBN is controlled by viral regulatory regions. In yet another embodiment, the expression of human CRBN is controlled by viral promoter and regulatory regions. In still other embodiments, the expression of human CRBN is controlled by homologous (e.g., mouse) promoter and/or regulatory regions. In one embodiment, the expression of human CRBN is controlled by mouse promoter. In another embodiment, the expression of human CRBN is controlled by mouse regulatory regions. In yet another embodiment, the expression of human CRBN is controlled by mouse promoter and regulatory regions. In a particular embodiment of transgenic mice, the expression of human CRBN is controlled by mouse CRBN promoter and/or regulatory regions. In one embodiment, the expression of human CRBN is controlled by mouse CRBN promoter. In another embodiment, the expression of human CRBN is controlled by mouse CRBN regulatory regions. In yet another embodiment, the expression of human CRBN is controlled by mouse CRBN promoter and regulatory regions.

In another embodiment, tetracycline-inducible systems can be used to generate transgenic mice, in which expression of a gene of interest can be controlled by the presence or absence of tetracycline or its derivatives (e.g., doxycycline). See Hickman-Davis et al., *Pediatric Respiratory Reviews* 2006, 7: 49. In these systems, two separate transgenic mouse lines are generated: a transactivator mouse, in which a tetracycline-controlled transactivator is expressed, and a responder mouse, in which expression of a gene of interest (e.g., CRBN) is under the control of a tetracycline-dependent promoter. The breeding of the transactivator mouse and the responder mouse produces a double-transgenic mouse, in which expression of the gene of interest (e.g., CRBN) responds to tetracycline or its derivatives (e.g., doxycycline). In some embodiments, the absence of tetracycline or its derivatives (e.g., doxycycline) allows for transcription of the transgene, and the presence of tetracycline or its derivatives (e.g., doxycycline) causes transcriptional downregulation (tet-OFF). In other embodiments, the presence of tetracycline or its derivatives (e.g., doxycycline) allows for transcription of the transgene, and removal of tetracycline or its derivatives (e.g., doxycycline) results in transcriptional downregulation (tet-ON).

In certain embodiments, the human CRBN is expressed in a similar expression pattern in the transgenic mice as mouse CRBN is expressed in mice. In other embodiments, the human CRBN is expressed in a similar expression pattern in the transgenic mice as human CRBN is expressed in humans. In some embodiments, the level of expression of human CRBN in the transgenic mice is similar to the level of expression of mouse CRBN in mice. In other embodiments, the level of expression of human CRBN in the transgenic mice is similar to the level of expression of human CRBN in humans. In yet other embodiments, the level of expression of human CRBN in the transgenic mice is different from the level of expression of mouse CRBN in mice. In still other embodiments, the level of expression of human CRBN in the transgenic mice is different from the level of expression of human CRBN in humans. In one embodiment, the level of expression of human CRBN in the transgenic mice is higher than the level of expression of mouse CRBN in mice. In another embodiment, the level of expression of human CRBN in the transgenic mice is lower than the level of expression of mouse CRBN in mice. In yet another embodiment, the level of expression of human CRBN in the transgenic mice is higher than the level of expression of human CRBN in humans. In still another embodiment, the level of expression of human CRBN in the transgenic mice is lower than the level of expression of human CRBN in humans. In certain embodiments, the level of expression of human CRBN in the transgenic mice is about 1, about 2, about 3, about 4, or about 5-fold the level of expression of mouse CRBN in mice. In certain embodiments, the level of expression of human CRBN in the transgenic mice is about 1, about 2, about 3, about 4, or about 5-fold the level of expression of human CRBN in humans.

The patterns of expression of human or mouse CRBN can be measured by methods well know in the art, including but not limited to, in situ hybridization, immunohistochemical staining (HM), etc. The levels of expression of human or mouse CRBN can be measured by methods well know in the art, including but not limited to, Northern blot, Western blot, RT-PCR, or quantitative RT-PCR. The expression levels of various housekeeping genes (e.g., GADPH, β-actin, ubiquitin, or hsp 90) can be measured using similar methods. Relative expression levels of human or mouse CRBN that are normalized based on the expression levels of housekeeping genes from the same samples can be compared.

In certain embodiments, the transgenic animals comprise alterations to the endogenous gene (e.g., mouse CRBN gene) as well as the introduced genetic alterations (e.g., human CRBN gene). For example, the host animals may be either "knockouts" and/or "knockins" for a target gene (e.g., CRBN). That is, the host animal's endogenous CRBN gene (e.g., mouse CRBN) may be "knocked out," and/or a human CRBN gene may be "knocked in." Knockouts have a partial or complete loss of function in one or both alleles of an endogenous gene (e.g., mouse CRBN). Knockins have an introduced genetic alteration (e.g., human CRBN) with different sequence and/or function from the endogenous gene (e.g., mouse CRBN). Knockouts and knockins may be combined such that the endogenous gene is disabled and an altered form is introduced. For example, in certain embodiments, it is preferable to knockout the host animal's endogenous CRBN gene, while introducing human CRBN gene. In one embodiment, the mouse CRBN gene is knocked out while the human CRBN gene is knocked in.

In certain embodiments, the target gene expression is undetectable or insignificant in a knockout animal. For example, a knockout of CRBN gene means that the expression of CRBN gene is not detectable or only present at insignificant levels; consequently, the function of the CRBN gene has been substantially decreased. Knockout may be achieved by a variety of mechanisms well known in the art, including but not limited to, introducing a disruption of the coding sequence, e.g., insertion of one or more stop codons, insertion of a DNA fragment, etc., deleting a portion of the coding sequence, substituting stop codons for the coding sequence, etc. In some embodiments, a chromosomal deletion of all or part of the target gene (e.g., CRBN) may be achieved by deletions of all or part of the coding region or deletions of the non-coding regions, which include the promoter region, 3' regulatory sequences, and/or enhancers, etc. In some embodiments, knockout of a target gene (e.g., CRBN) can be achieved by deletions of gene that is necessary for activating expression of the target gene (e.g., CRBN). In other embodiments, a functional knockout can be achieved by introducing an antisense construct that blocks expression of the target gene (e.g., CRBN). See Li and Cohen, *Cell* 1996, 85:319-329. In certain embodiments, "knockouts" also include conditional knockouts, for example, where alteration of the target gene (e.g., CRBN) occurs when certain conditions are satisfied, including but not limited to, exposure of the animal to a substance that promotes target gene alteration, introduction of an enzyme that promotes recombination at the target gene site (e.g., Cre in the Cre-lox system), or other method for directing the target gene alteration postnatally.

A "knockin" of a gene (e.g., human CRBN) means an alteration in a host (e.g., mouse) cell genome that results in expression and/or function of the gene (e.g., human CRBN). In certain embodiments, increased (including ectopic) expression of the gene (e.g., human CRBN) can be achieved by introduction of an additional copy of the gene (e.g., human CRBN), or by operatively inserting a regulatory sequence that enhances expression of the gene (e.g., human CRBN). In some embodiments, the knockin is constitutive, i.e., the expression of the gene (e.g., human CRBN) is constitutive. In other embodiments, the knockin is conditional, i.e., the expression of the gene (e.g., human CRBN) is dependent on the presence of an activator or a repressor. In yet other embodiments, a knockin of a gene can be a knockin of an endogenous gene (e.g., mouse CRBN) in a host (e.g., mouse). This can be achieved by introduction of an additional copy of the endogenous gene (e.g., mouse CRBN), or by operatively inserting a regulatory sequence that enhances expression of the endogenous gene (e.g., mouse CRBN).

In certain embodiments, the hCRBN transgenic mouse has a knockin of the human CRBN gene (including but not limited to, full-length, a fragment thereof, wild-type, variants, etc.). In one embodiment, the hCRBN transgenic mouse has a knockin of full-length human CRBN gene. In another embodiment, the hCRBN transgenic mouse has a knockin of a fragment of human CRBN gene. In some embodiments, the hCRBN transgenic mouse has a knockout of the mouse CRBN gene. In other embodiments, the hCRBN transgenic mouse has a knockin of the human CRBN gene (including but not limited to, full-length, a fragment thereof, wild-type, variants, etc.) and a knockout of the mouse CRBN gene. In one embodiment, the hCRBN transgenic mouse has a knockin of full-length human CRBN gene and a knockout of the mouse CRBN gene. In another embodiment, the hCRBN transgenic mouse has a knockin of a fragment of human CRBN gene and a knockout of the mouse CRBN gene.

In certain embodiments, the hCRBN transgenic mouse expresses human CRBN (including but not limited to, full-length, a fragment thereof, wild-type, variants, etc.). In one embodiment, the hCRBN transgenic mouse expresses full-length human CRBN gene. In another embodiment, the hCRBN transgenic mouse expresses a fragment of human CRBN gene. In some embodiments, the hCRBN transgenic mouse does not express endogenous mouse CRBN. In other embodiments, the hCRBN transgenic mouse expresses human CRBN (including but not limited to, full-length, a fragment thereof, wild-type, variants, etc.) but does not express endogenous mouse CRBN. In one embodiment, the hCRBN transgenic mouse expresses full-length human CRBN gene but does not express endogenous mouse CRBN. In another embodiment, the hCRBN transgenic mouse expresses a fragment of human CRBN gene but does not express endogenous mouse CRBN.

In some embodiments, the hCRBN transgenic mouse expresses human CRBN isoform 1. In other embodiments, the hCRBN transgenic mouse expresses human CRBN isoform 2. In certain embodiments, the hCRBN transgenic mouse expresses human CRBN isoform 1 and isoform 2. In some embodiments, the hCRBN transgenic mouse expresses full-length human CRBN isoform 1. In other embodiments, the hCRBN transgenic mouse expresses full-length human CRBN isoform 2. In certain embodiments, the hCRBN transgenic mouse expresses full-length human CRBN isoform 1 and full-length isoform 2. In some embodiments, the hCRBN transgenic mouse expresses a fragment of human CRBN isoform 1. In other embodiments, the hCRBN transgenic mouse expresses a fragment of human CRBN isoform 2. In certain embodiments, the hCRBN transgenic mouse expresses a fragment of human CRBN isoform 1 and a fragment of isoform 2.

In certain embodiments, the human CRBN protein is expressed from a full-length human CRBN gene. In some embodiments, the human CRBN protein is expressed from a full-length human CRBN cDNA. In other embodiments, the human CRBN protein is expressed from a full-length human CRBN cDNA, wherein of the human CRBN cDNA comprises a nucleic acid sequence of SEQ ID NO:5. In yet other embodiments, the human CRBN protein is expressed from a full-length human CRBN cDNA, wherein of the human CRBN cDNA comprises a nucleic acid sequence of SEQ ID NO:6. In some embodiments, the human CRBN protein is expressed from a mouse-human chimeric CRBN gene. In yet other embodiments, the human CRBN protein is expressed from a mouse-human chimeric CRBN gene that comprises a portion of the mouse CRBN cDNA and a portion of the human CRBN cDNA. In still other embodiments, the human CRBN protein is expressed from a mouse-human chimeric CRBN gene that comprises a portion of the mouse CRBN genomic DNA and a portion of the human CRBN genomic DNA. In one embodiment, the human CRBN protein is expressed from a mouse-human chimeric CRBN gene that comprises a portion of the mouse CRBN cDNA and a portion of the human CRBN genomic DNA. In a particular embodiment, the human CRBN protein is expressed from a mouse-human chimeric CRBN gene that comprises a portion of the mouse CRBN genomic DNA and a portion of the human CRBN cDNA. In one specific embodiment, the human CRBN protein is expressed from a mouse-human chimeric CRBN gene that comprises a portion of the mouse CRBN genomic DNA and a portion of the human CRBN cDNA, wherein the portion of the human CRBN cDNA comprises a nucleic acid sequence of SEQ ID NO:7. In another specific embodiment, the human CRBN protein is expressed from a mouse-human chimeric CRBN gene that is generated by homologous recombination between the mouse CRBN genomic DNA and a targeting construct comprising a portion of human CRBN cDNA, wherein targeting construct comprises a nucleic acid sequence of SEQ ID NO:8.

In certain embodiments, a fragment of human CRBN protein is expressed from a fragment of human CRBN gene. In some embodiments, a fragment of human CRBN protein is expressed from a fragment of human CRBN cDNA. In one embodiment, a fragment of human CRBN protein is expressed from a fragment of human CRBN isoform 1 cDNA. In another embodiment, a fragment of human CRBN protein is expressed from a fragment of human CRBN isoform 2 cDNA. In some embodiments, a fragment of human CRBN protein is expressed from a fragment of human CRBN cDNA, wherein of the human CRBN cDNA comprises a nucleic acid sequence of SEQ ID NO:5. In other embodiments, a fragment of human CRBN protein is expressed from a fragment of human CRBN cDNA, wherein of the human CRBN cDNA comprises a nucleic acid sequence of SEQ ID NO:6. In some embodiments, a fragment of human CRBN protein is expressed from a fragment of a mouse-human chimeric CRBN gene. In yet other embodiments, a fragment of human CRBN protein is expressed from a fragment of a mouse-human chimeric CRBN gene that comprises a portion of the mouse CRBN cDNA and a portion of the human CRBN cDNA. In still other embodiments a fragment of human CRBN protein is expressed from a fragment of a mouse-human chimeric CRBN gene that comprises a portion of the mouse CRBN genomic DNA and a portion of the human CRBN genomic DNA. In one embodiment, a fragment of human CRBN protein is expressed from a fragment of a mouse-human chimeric CRBN gene that comprises a portion of the mouse CRBN cDNA and a portion of the human CRBN genomic DNA. In a particular embodiment, a fragment of human CRBN protein is expressed from a fragment of a mouse-human chimeric CRBN gene that comprises a portion of the mouse CRBN genomic DNA and a portion of the human CRBN cDNA. In one specific embodiment, a fragment of human CRBN protein is expressed from a fragment of a mouse-human chimeric CRBN gene that comprises a portion of the mouse CRBN genomic DNA and a portion of the human CRBN cDNA, wherein the portion of the human CRBN cDNA comprises a nucleic acid sequence of SEQ ID NO:7. In another specific embodiment, a fragment of human CRBN protein is expressed from a fragment of a mouse-human chimeric CRBN gene that is generated by homologous recombination between the mouse CRBN genomic DNA and a targeting construct comprising a portion of human CRBN cDNA, wherein targeting construct comprises a nucleic acid sequence of SEQ ID NO:8.

Also provided herein are isolated cells, cell lines, tissues, or organs obtained or derived from a transgenic animal. In certain embodiments, provided are isolated cells obtained from a transgenic animal. In some embodiments, provided are isolated cell lines derived from a transgenic animal. In other embodiments, provided are isolated tissues obtained from a transgenic animal. In yet other embodiments, provided are isolated organs obtained from a transgenic animal.

In one aspect, provided is a cell derived from a transgenic mouse provided herein, wherein the cell comprises a nucleic acid sequence encoding human CRBN or a fragment thereof. In certain embodiments, the cell is obtained from the transgenic mouse. In one embodiment, the cell is an isolated cell. In one embodiment, the nucleic acid sequence encodes human CRBN. In certain embodiments, the nucleic acid sequence encoding the human CRBN is stably integrated into a chromosome of the transgenic mouse. In another embodiment, the nucleic acid sequence encodes a fragment of human CRBN. In certain embodiments, the nucleic acid sequence encoding the fragment of the human CRBN is stably integrated into a chromosome of the transgenic mouse. In certain embodiments, the nucleic acid sequence encodes a fragment of human CRBN that comprises a polypeptide that starts at codon 24 Glutamate of human CRBN isoform 1 and ends at the last codon of human CRBN isoform 1. In certain embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In some embodiments, full-length human CRBN is expressed. In other embodiments, a fragment of human CRBN is expressed. In yet other embodiments, mouse CRBN is not expressed. In still other embodiments, full-length human CRBN is expressed but mouse CRBN is not expressed. In again other embodiments, a fragment of human CRBN is expressed but mouse CRBN is not expressed.

In another aspect, provided is a cell line derived from a transgenic mouse provided herein, wherein the cell line comprises a nucleic acid sequence encoding human CRBN or a fragment thereof. In one embodiment, the cell line is an isolated cell line. In one embodiment, the nucleic acid sequence encodes human CRBN. In certain embodiments, the nucleic acid sequence encoding the human CRBN is stably integrated into a chromosome of the transgenic mouse. In another embodiment, the nucleic acid sequence encodes a fragment of human CRBN. In certain embodiments, the nucleic acid sequence encoding the fragment of the human CRBN is stably integrated into a chromosome of the transgenic mouse. In certain embodiments, the nucleic acid sequence encodes a fragment of human CRBN that comprises a polypeptide that starts at codon 24 Glutamate of human CRBN isoform 1 and ends at the last codon of human CRBN isoform 1. In certain embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In certain embodiments, the cell lines is a transformed cell line. In some embodiments, full-length human CRBN is expressed. In other embodiments, a fragment of human CRBN is expressed. In yet other embodiments, mouse CRBN is not expressed. In still other embodiments, full-length human CRBN is expressed but mouse CRBN is not expressed. In again other embodiments, a fragment of human CRBN is expressed but mouse CRBN is not expressed.

In another aspect, provided is a tissue derived from a transgenic mouse provided herein, wherein the tissue comprises a nucleic acid sequence encoding human CRBN or a fragment thereof. In certain embodiments, the tissue is obtained from the transgenic mouse. In one embodiment, the tissue is an isolated tissue. In one embodiment, the nucleic acid sequence encodes human CRBN. In certain embodiments, the nucleic acid sequence encoding the human CRBN is stably integrated into a chromosome of the transgenic mouse. In another embodiment, the nucleic acid sequence encodes a fragment of human CRBN. In certain embodiments, the nucleic acid sequence encoding the fragment of the human CRBN is stably integrated into a chromosome of the transgenic mouse. In certain embodiments, the nucleic acid sequence encodes a fragment of human CRBN that comprises a polypeptide that starts at codon 24 Glutamate of human CRBN isoform 1 and ends at the last codon of human CRBN isoform 1. In certain embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In some embodiments, full-length human CRBN is expressed. In other embodiments, a fragment of human CRBN is expressed. In yet other embodiments, mouse CRBN is not expressed. In still other embodiments, full-length human CRBN is expressed but mouse CRBN is not expressed. In again other embodiments, a fragment of human CRBN is expressed but mouse CRBN is not expressed.

In another aspect, provided is an organ derived from a transgenic mouse provided herein, wherein the organ comprises a nucleic acid sequence encoding human CRBN or a fragment thereof. In certain embodiments, the organ is obtained from the transgenic mouse. In one embodiment, the organ is an isolated organ. In one embodiment, the nucleic acid sequence encodes human CRBN. In certain embodiments, the nucleic acid sequence encoding the human CRBN is stably integrated into a chromosome of the transgenic mouse. In another embodiment, the nucleic acid sequence encodes a fragment of human CRBN. In certain embodiments, the nucleic acid sequence encoding the fragment of the human CRBN is stably integrated into a chromosome of the transgenic mouse. In certain embodiments, the nucleic acid sequence encodes a fragment of human CRBN that comprises a polypeptide that starts at codon 24 Glutamate of human CRBN isoform 1 and ends at the last codon of human CRBN isoform 1. In certain embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8. In some embodiments, full-length human CRBN is expressed. In other embodiments, a fragment of human CRBN is expressed. In yet other embodiments, mouse CRBN is not expressed. In still other embodiments, full-length human CRBN is expressed but mouse CRBN is not expressed. In again other embodiments, a fragment of human CRBN is expressed but mouse CRBN is not expressed.

5.3 Method of Producing Transgenic Mouse Expressing Human CRBN

In another aspect, provided herein is a method for producing a transgenic mouse expressing human CRBN, comprising: (a) introducing a polynucleotide construct into a mouse egg, wherein the polynucleotide construct comprises a nucleic acid sequence encoding human CRBN or a fragment thereof; and (b) transferring the mouse egg into a female mouse. Also provided herein is a method for producing a transgenic mouse expressing human CRBN, comprising: (a) introducing a polynucleotide construct into a mouse embryo, wherein the polynucleotide construct comprises a nucleic acid sequence encoding human CRBN or a fragment thereof; and (b) transferring the mouse embryo into a female mouse. Also provided herein is a method for producing a transgenic mouse expressing human CRBN, comprising: (a) introducing a polynucleotide construct into a mouse embryonic stem (ES) cell, wherein the polynucleotide construct comprises a nucleic acid sequence encoding human CRBN or a fragment thereof; and (b) transferring the mouse ES cell into a female mouse. In certain embodiments, the nucleic acid sequence encodes human CRBN. In certain embodiments, the nucleic acid sequence encoding the human CRBN is stably integrated into a chromosome of the egg, embryo, or ES cell. In other embodiments, the nucleic acid sequence encodes a fragment of human CRBN. In certain embodiments, the nucleic acid sequence encoding the fragment of the human CRBN is stably integrated into a chromosome of the egg, embryo, or ES cell. In certain embodiments, the nucleic acid sequence encodes a fragment of human CRBN that comprises a polypeptide that starts at codon 24 Glutamate of human CRBN isoform 1 and ends at the last codon of human CRBN isoform 1. In certain embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8.

In certain embodiments, the method further comprises breeding the female mouse. In other embodiments, the method further comprises selecting offspring having the nucleic acid sequence encoding the human CRBN or a fragment thereof. In some embodiments, the method further comprises breeding the female mouse, and selecting offspring having the nucleic acid sequence encoding the human CRBN or a fragment thereof. Thus, further provided herein is a method for producing a transgenic mouse expressing human CRBN, comprising: (a) introducing a polynucleotide construct into a mouse egg, wherein the polynucleotide construct comprises a nucleic acid sequence encoding human CRBN or a fragment thereof; (b) transferring the mouse egg into a female mouse, and (c) breeding the female mouse, and selecting an offspring transgenic mouse expressing the human CRBN or fragment thereof. Also provided herein is a method for producing a transgenic mouse expressing human CRBN, comprising: (a) introducing a polynucleotide construct into a mouse embryo, wherein the polynucleotide construct comprises a nucleic acid sequence encoding human CRBN or a fragment thereof; (b) transferring the mouse embryo into a female mouse, and (c) breeding the female mouse, and selecting an offspring transgenic mouse expressing the human CRBN or fragment thereof. Also provided herein is a method for producing a transgenic mouse expressing human CRBN, comprising: (a) introducing a polynucleotide construct into a mouse ES cell, wherein the polynucleotide construct comprises a nucleic acid sequence encoding human CRBN or a fragment thereof; (b) transferring the mouse ES cell into a female mouse, and (c) breeding the female mouse, and selecting an offspring transgenic mouse expressing the human CRBN or fragment thereof.

In yet another aspect, provided herein is a transgenic mouse expressing human CRBN or a fragment thereof produced by a method, comprising: (a) introducing a polynucleotide construct into a mouse egg, wherein the polynucleotide construct comprises a nucleic acid sequence encoding human CRBN or a fragment thereof; and (b) transferring the mouse egg into a female mouse. Also provided herein is a transgenic mouse expressing human CRBN or a fragment thereof produced by a method, comprising: (a) introducing a polynucleotide construct into a mouse embryo, wherein the polynucleotide construct comprises a nucleic acid sequence encoding human CRBN or a fragment thereof; and (b) transferring the mouse embryo into a female mouse. Also provided herein is a transgenic mouse expressing human CRBN or a fragment thereof produced by a method, comprising: (a) introducing a polynucleotide construct into a mouse ES cell, wherein the polynucleotide construct comprises a nucleic acid sequence encoding human CRBN or a fragment thereof; and (b) transferring the mouse ES cell into a female mouse. Further provided herein is a transgenic mouse expressing human CRBN or a fragment thereof produced by a method, comprising: (a) introducing a polynucleotide construct into a mouse egg, wherein the polynucleotide construct comprises a nucleic acid sequence encoding human CRBN or a fragment thereof; (b) transferring the mouse egg into a female mouse; and (c) breeding the female mouse, and selecting an offspring transgenic mouse expressing the human CRBN or fragment thereof. Also provided herein is a transgenic mouse expressing human CRBN or a fragment thereof produced by a method, comprising: (a) introducing a polynucleotide construct into a mouse embryo, wherein the polynucleotide construct comprises a nucleic acid sequence encoding human CRBN or a fragment thereof; (b) transferring the mouse embryo into a female mouse; and (c) breeding the female mouse, and selecting an offspring transgenic mouse expressing the human CRBN or fragment thereof. Also provided herein is a transgenic mouse expressing human CRBN or a fragment thereof produced by a method, comprising: (a) introducing a polynucleotide construct into a mouse ES cell, wherein the polynucleotide construct comprises a nucleic acid sequence encoding human CRBN or a fragment thereof (b) transferring the mouse ES cell into a female mouse; and (c) breeding the female mouse, and selecting an offspring transgenic mouse expressing the human CRBN or fragment thereof. In certain embodiments, the nucleic acid sequence encodes human CRBN. In certain embodiments, the nucleic acid sequence encoding the human CRBN is stably integrated into a chromosome of the egg, embryo, or ES cell. In other embodiments, the nucleic acid sequence encodes a fragment of human CRBN. In certain embodiments, the nucleic acid sequence encoding the fragment of the human CRBN is stably integrated into a chromosome of the egg, embryo, or ES cell. In certain embodiments, the nucleic acid sequence encodes a fragment of human CRBN that comprises a polypeptide that starts at codon 24 Glutamate of human CRBN isoform 1 and ends at the last codon of human CRBN isoform 1. In certain embodiments, the nucleic acid sequence encodes a fragment of human CRBN that comprises a polypeptide that starts at codon 23 Glutamate of human CRBN isoform 2 and ends at the last codon of human CRBN isoform 2. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8.

In specific embodiments herein, reference to a "human CRBN" refers to a full-length human CRBN.

In still another aspect, provided herein is a method for producing a transgenic mouse expressing human CRBN in a particular genetic background, wherein the method comprises breeding a transgenic mouse expressing human CRBN or a fragment thereof provided herein with a mouse of the genetic background. Also provided herein is a transgenic mouse expressing human CRBN in a particular genetic background produced by a method, comprising breeding a transgenic mouse expressing human CRBN or a fragment thereof provided herein with a mouse of the genetic background. In certain embodiments, the mouse of a genetic background is a NSG/NOG mouse model. In other embodiments, the mouse of a genetic background is a Vk*myc multiple myeloma mouse model. In yet other embodiments, the mouse of a genetic background is a Eu-v-abl/Eu-c-Myc multiple myeloma mouse model. In still other embodiments, the mouse of a genetic background is a Eu-c-Myc lymphoma mouse model. In one embodiment, the mouse of a genetic background is a human IKZF1 transgenic mouse model. In another embodiment, the mouse of a genetic background is a human IKZF3 transgenic mouse model.

In yet another aspect, provided herein is a method for producing a transgenic mouse expressing human CRBN in a particular genetic background, wherein the method comprises breeding a transgenic mouse whose genome comprises a nucleic acid encoding human CRBN or a fragment thereof, as provided in Section 5.2, with a mouse of the genetic background. Also provided herein is a transgenic mouse expressing human CRBN in a particular genetic background produced by a method, comprising breeding a transgenic mouse whose genome comprises a nucleic acid encoding human CRBN or a fragment thereof, as provided in Section 5.2, with a mouse of the genetic background. In certain embodiments, the mouse of a genetic background is a NSG/NOG mouse model. In other embodiments, the mouse of a genetic background is a Vk*myc multiple myeloma mouse model. In yet other embodiments, the mouse of a genetic background is a Eu-v-abl/Eu-c-Myc multiple myeloma mouse model. In still other embodiments, the mouse of a genetic background is a Eu-c-Myc lymphoma mouse model. In one embodiment, the mouse of a genetic background is a human IKZF1 transgenic mouse model. In another embodiment, the mouse of a genetic background is a human IKZF3 transgenic mouse model.

Techniques for producing transgenic animals are well known in the art. See, e.g., Houdebine, *Transgenic animals—Generation and Use* (Harwood Academic, 1997); Hogan et al., *Manipulating the Mouse Embryo: A Laboratory Manual Cold Spring Harbor Laboratory*, 2d ed., (Cold Spring Harbor Laboratory, 1994); Krimpenfort et al., *Bio/Technology* 1991, 9:844; Palmiter et al., *Cell* 1985, 41:343; Hammer et al., *Nature* 1985, 315:680; U.S. Pat. Nos. 5,602,299; 5,175,384; 6,066,778 and 6,037,521, which are incorporated herein in their entirety. Technologies used in generating transgenic animals include, but are not limited to, pronuclear injection (Gordon, *Proc. Nat. Acad. Sci. USA* 1980, 77:7380-7384; U.S. Pat. No. 4,873,191), electroporation (Lo, *Mol. Cell. Biol.* 1983, 3:1803-1814), homologous recombination (Thompson et al., *Cell* 1989, 56:313-321; Hanks et al., *Science* 1995, 269: 679-682), retrovirus gene transfer into germ lines (Van der Putten et al., *Proc. Nat. Acad. Sci. USA* 1985, 82:6148-6152), and sperm-mediated gene transfer (Lavitrano et al., *Cell* 1989, 57:717-723).

In certain embodiments, transgenic animals are produced by pronuclear injection. A zygote is usually the best target for pronuclear injection. For example, a male mouse pronucleus is approximately 20 μm in diameter, suitable for injection of 1-2 pL of DNA solution. Using a zygote as a target for pronuclear injection has great advantage. The injected DNA, in most cases, is incorporated into the host gene before the first cell division. As a result, almost all cells of the transgenic animal carry the incorporated transgene. Because nearly 50% of the germ cells contain the transgene, the transmission of the transgene to offspring of the founder is highly efficient. In certain embodiments, a vector containing the gene of interest (e.g., hCRBN) is injected into pronuclei (i.e., mouse fertilized eggs at a pronuclear state). The injected pronuclei are subsequently planted into the uterus of a pseudopregnant female mouse. Offspring generated can have one or more copies of the transgene.

In some embodiments, transgenic animals are produced by introduction of a gene of interest into embryonic stem (ES) cells. ES cells are obtained from pre-implantation embryos cultured in vitro under appropriate conditions. See Evans et al., *Nature* 1981, 292:154-156; Bradley et al., *Nature* 1984, 309:255-258; Gossler et al., *Proc. Natl. Acad. Sci U.S.A.* 1986, 83:9065-9069; Robertson et al., *Nature* 1986, 322:445-448. In certain embodiments, transgenes are efficiently introduced into the ES cells by DNA transfection using a variety of methods known to the art, including but not limited to, electroporation, calcium phosphate co-precipitation, protoplast or spheroplast fusion, lipofection and DEAE-dextran-mediated transfection. In some embodiments, transgenes are introduced into ES cells by retrovirus-mediated transduction. In other embodiments, transgenes are introduced into ES cells by microinjection. Then, the transformed ES cells carrying the transgene are combined with blastocysts from a non-human animal (e.g., mouse). The ES cells thereafter colonize the embryo and contribute to the germ line of the resulting chimeric animals. For review see Jaenisch, *Science* 1988, 240:1468-1474. Before introducing the transformed ES cells into the blastocoel, the transformed ES cells can be subjected to various selection protocols to enrich for ES cells that have integrated the transgene if the transgene provides a means for such selection (e.g., the transgene construct contains a Neomycin selection cassette). The resulting offspring are chimeric with respect to the ES and host cells. Nonchimeric strains that exclusively comprise the ES progeny can be obtained by cross-breeding. This technique is described, for example, in WO91/10741.

In other embodiments, transgenic animals are produced by retroviral infection. A developing non-human (e.g., mouse) embryo can be cultured to the blastocyst stage in vitro. Blastomeres are suitable targets for retroviral infection. To increase the efficiency of infection, enzymatic treatment of blastomeres to remove the zona pellucida is preferred. The viral vector used is usually a replication-defective retrovirus that carries the transgene. The blastomeres are cultured on a monolayer of virus-producing cells, and infection can be easily and efficiently achieved. Alternatively, infection can be performed at a later stage, for example, virus or virus-producing cells can be injected into the blastocoel. Founder animals produced by retroviral infection are mostly chimeric for the transgene because incorporation occurs only in a portion of the cells that form the transgenic animals. In some embodiments, the founder animals can have retroviral insertions of the transgene at a variety of positions in the genome. In another embodiment, transgenes can be introduced into the germ line by intra-uterine retroviral infection of the midgestation embryo, although the efficiency is much lower.

In yet other embodiments, transgenic animals can be produced by nuclear transfer technology as described in Schnieke et al., *Science* 1997, 278:2130 and Cibelli et al., *Science* 1998, 280:1256. Using this method, somatic cells (e.g., primary fetal fibroblasts) from donor animals (e.g., mouse) are stably transfected with a construct containing the coding sequence for a gene of interest (e.g., human CRBN). Stably transfected fibroblasts are then fused to enucleated oocytes, cultured, and transferred into female mouse to produce transgenic mice.

Vectors for introducing an exogenous DNA include, but are not limited to, plasmids, retroviruses and other animal viruses, BACs, YACs, and the like. Methods for manipulating these vectors, including but not limited to, construction, molecular cloning, amplification, production, transfection, transformation, transduction, infection, electroporation, etc., are well known in the art.

A transgenic gene construct or targeting construct can be generated by inserting a gene of interest (e.g., hCRBN) or a fragment thereof into a suitable vector (e.g., plasmids, retroviruses and other animal viruses, BACs, YACs) using conventional molecular biological techniques. In some embodiments, the targeting construct contains a full-length hCRBN gene. In certain embodiments, the targeting construct contains a full-length hCRBN cDNA. In other embodiments, the targeting construct contains a fragment of hCRBN gene. In yet other embodiments, the targeting construct contains a fragment of hCRBN cDNA. The targeting construct can also contain a poly(A) sequence (e.g., bGH pA) after the gene of interest (e.g., hCRBN). Further, the targeting construct can contain a selection marker (e.g., Neomycin selection cassette) so that transformed host cells (e.g., ES cells) can be subjected to various selection protocols to enrich for transformed cells that have integrated the transgene.

In certain other embodiments, the targeting construct further contains mouse homologous arms flanking the gene of interest (e.g., hCRBN), the poly(A) sequence (e.g., bGH pA), and the selection marker (e.g., Neomycin selection cassette). In one embodiment, the flanking mouse homologous arms comprise a 5' homology arm and a 3' homology arm. In a specific embodiment, the flanking mouse homologous arms are mouse genomic DNA, which will determine where in the mouse genome the gene of interest (e.g., hCRBN) is going to be stably integrated. In another embodiment, the stable integration of the gene of interest (e.g., hCRBN) into the mouse genome is through homologous recombination.

In a specific embodiment, the targeting construct comprises a gene of interest, a poly(A) sequence, a selection marker, a 5' homology arm, and a 3' homology arm. In one embodiment, the targeting construct comprises hCRBN cDNA or a fragment thereof, a bGH pA sequence, a Neomycin selection cassette, a 5' homology arm, and a 3' homology arm. In another embodiment, the targeting construct comprises a full-length hCRBN cDNA, a bGH pA sequence, a Neomycin selection cassette, a 5' homology arm, and a 3' homology arm. In yet another embodiment, the targeting construct comprises a fragment of hCRBN cDNA, a bGH pA sequence, a Neomycin selection cassette, a 5' homology arm, and a 3' homology arm. In still another embodiment, the targeting construct comprises a fragment of hCRBN cDNA encoding a polypeptide that starts at codon 24 of human CRBN isoform 1 and ends at the last codon of the human CRBN isoform 1, a bGH pA sequence, a Neomycin selection cassette, a 5' homology arm, and a 3' homology arm. In still another embodiment, the targeting construct comprises a fragment of hCRBN cDNA encoding a polypeptide that starts at codon 23 of human CRBN isoform 2 and ends at the last codon of the human CRBN isoform 2, a bGH pA sequence, a Neomycin selection cassette, a 5' homology arm, and a 3' homology arm. In one embodiment, the targeting construct comprises hCRBN isoform 1 cDNA with a nucleic acid sequence of SEQ ID NO:5, a bGH pA sequence, a Neomycin selection cassette, a 5' homology arm, and a 3' homology arm. In another embodiment, the targeting construct comprises hCRBN isoform 2 cDNA with a nucleic acid sequence of SEQ ID NO:6, a bGH pA sequence, a Neomycin selection cassette, a 5' homology arm, and a 3' homology arm. In one particular embodiment, the targeting construct comprises a fragment of hCRBN cDNA with a nucleic acid sequence of SEQ ID NO:7, a bGH pA sequence, a Neomycin selection cassette, a 5' homology arm, and a 3' homology arm. In another particular embodiment, the targeting construct comprises a nucleic acid sequence of SEQ ID NO:8. In some embodiments, the targeting construct is stably integrated into a mouse chromosome.

It has been shown that leaving the selection marker in the genomic DNA can cause many unanticipated problems. For example, the presence of the Neomycin cassette can change the expression of neighboring loci. This can be particularly problematic in gene clusters where neighbouring genes are in the same family, because the neighboring genes affected may have similar or identical functions. In that case, a slight difference in targeting constructs can lead to marked differences in phenotype. Thus, targeting constructs usually contain two loxP sites flanking the Neomycin selection cassette, so that the Neomycin cassette can be removed after targeting by transient expression of the Cre recombinase. This will leave one loxP site in the genomic DNA. Although theoretically even a small loxP site could cause alterations in the expression of neighboring genes, no such cases have yet been reported.

Various gene editing methods can be used to enhance targeting of the transgene in host cells. Non-limiting examples of gene editing methods include transcription activator-like effector nucleases (TALENs), clustered regularly interspaced short palindromic repeat (CRISPR/Cas9), and zinc finger nuclease (ZFN) gene editing procedures. TALENs are artificial restriction enzymes generated by fusing a transcription activator-like effector DNA-binding domain to a DNA cleavage domain. By combining such an engineered transcription activator-like effector with a DNA cleavage domain (which cuts DNA strands), one can engineer restriction enzymes that are specific for any desired DNA sequence. When these restriction enzymes are introduced into cells, they can be used for genome editing in situ. The CRISPR/Cas9 system is another system commonly used for gene editing (adding, disrupting, or changing the sequence of specific genes). The CRISPR/Cas9 system is a prokaryotic immune system that confers resistance to foreign genetic elements, such as plasmids and phages. CRISPR spacers recognize and cut these exogenous genetic elements in a manner analogous to RNAi in eukaryotic organisms. By delivering the Cas9 protein and appropriate guide RNAs into a cell, the host genome can be cut at any desired location. Zinc finger nucleases (ZFNs) are artificial restriction enzymes generated by fusing a zinc finger DNA-binding domain to a DNA-cleavage domain. Zinc finger domains can be engineered to target specific desired DNA sequences. This enables zinc finger nucleases to target unique sequences within the genome.

The various gene editing procedures have different advantages and disadvantages. CRISPR/Cas9 based engineering is the newest, and its pitfalls are just being discovered, for example, nonspecific site selection has been reported. CRISPR/Cas9 system also tends not to be very effective, if the targeted area is bigger than a few hundred base pairs. In general, genetically engineering mouse is unpredictable with regard to which gene editing method would work or why one method would work better than the others.

In some embodiments, the TALENs gene editing procedure is used. In certain embodiments, various TALENs and corresponding TALENs target sites are designed to select TALENs with the most activity. The pair of TALEN and TALEN target site with the most activity is then used for subsequent gene targeting. In other embodiments, the CRISPR/Cas9 gene editing procedure is used. In certain embodiments, various guide RNAs and corresponding CRISPR target sites are designed to select guide RNAs with the most activity. The pair of guide RNA and CRISP target site with the most activity is then used for subsequent gene targeting. In still other embodiments, the ZFNs gene editing procedure is used. In certain embodiments, various ZFNs and corresponding ZFNs target sites are designed to select ZFNs with the most activity. The pair of ZFN and ZFN target site with the most activity is then used for subsequent gene targeting. In one specific embodiment, the CRISPR/Cas9 gene editing procedure did not generate desired gene targeting. Surprisingly, in another specific embodiment, the TALENs gene editing procedure generated desired gene targeting.

In one embodiment, ES cells are transfected with the desired DNA by electroporation, and transgenic animals are produced from the transfected ES cells. In another embodiment, the appropriate DNAs are coinjected into the pronucleus or cytoplasm of embryos, preferably at the single cell stage, and the embryos are allowed to develop into mature transgenic animals.

In a specific embodiment, TALENs gene editing procedure is used in combination with transfection of ES cells to generate transgenic mice. In another specific embodiment, TALENs gene editing procedure is used in combination with pronuclear injection to generate transgenic mice. In yet another specific embodiment, CRISPR/Cas9 gene editing procedure is used in combination with transfection of ES cells to generate transgenic mice. In still another specific embodiment, CRISPR/Cas9 gene editing procedure is used in combination with pronuclear injection to generate transgenic mice. In a specific embodiment, ZFNs gene editing procedure is used in combination with transfection of ES cells to generate transgenic mice. In another specific embodiment, ZFNs gene editing procedure is used in combination with pronuclear injection to generate transgenic mice. In one embodiment, CRISPR/Cas9 gene editing procedure in combination with transfection of ES cells or pronuclear injection was not successful in producing desired transgenic mice. Surprisingly, in another embodiment, TALENs gene editing procedure in combination with transfection of ES cells produced desired transgenic mice.

Transgenic animals can be screened for the presence and/or expression of the transgene by any suitable methods known in the art. In certain embodiments, screening is accomplished by Southern blot or Northern blot analysis, using an oligonucleotide probe that is complementary to at least a portion of the DNA or RNA of the transgene. In other embodiments, screening is accomplished by Western blot analysis using an antibody specific binding to the protein encoded by the transgene. In some embodiments, DNA is prepared from tail tissue of the transgenic animal (e.g., transgenic mouse) and analyzed by Southern blot analysis or PCR for the transgene. In other embodiments, the cells, tissues, or organs believed to express the transgene at the highest levels are tested for the presence and expression of the transgene using PCR or Southern, Northern, or Western blot analysis. In yet other embodiments, any cells, tissues, or organs that express the transgene can be tested for the presence and expression of the transgene using such methods.

Founder animals can be bred, inbred, outbred, or crossbred to produce colonies of the desired transgenic animals. Non-limiting examples of such breeding strategies include: outbreeding of founder animals with more than one integration sites to establish separate lines; inbreeding of separate lines to produce compound transgenics that express the transgene at higher levels because of the additive effect of each transgene; crossing of heterozygous transgenic mice to increase expression of the transgene and/or to produce mice homozygous for a given integration site; crossing of separate homozygous lines to produce compound heterozygous or homozygous lines; breeding animals to different inbred genetic backgrounds to study effects of modifying alleles on expression of the transgene and the physiological effects of expression of the transgene.

Mouse strains that can be used for generating transgenic mice include, but are not limited to, CD-1® Nude mice, CD-1 mice, NU/NU mice, BALB/C Nude mice, BALB/C mice, NIH-III mice, SCID™ mice, outbred SCID™ mice, SCID™ Beige mice, C3H mice, C57BL/6 mice, DBA/2 mice, FVB mice, CB17 mice, 129 mice, SJL mice, B6C3F1 mice, BDF1 mice, CDF1 mice, CB6F1 mice, CF-1 mice, Swiss Webster mice, SKH1 mice, PGP mice, and B6SJL mice. Additionally, various substrains (e.g., J or N substrain) within each mouse strain can be used. In certain embodiments, albino B6N mice are used. In some embodiments, C57BL/6J mice are used. In other embodiments, C57BL/6N mice are used. In a specific embodiment, C57BL/6NTac mice are used.

5.4 Method of Using Transgenic Mouse Expressing Human CRBN

Transgenic mice expressing human CRBN can be used for a variety of studies, such as evaluating compounds in treating various diseases (e.g., cancer), which includes but is not limited to efficacy, specificity, toxicity, pharmacokinetics, pharmacodynamics, mechanism of action, optimizing dosing regimens, and studying combinational therapies with other therapeutics for such diseases.

5.4.1 Biomarkers as Readouts in Methods of Using Transgenic Mouse

In many of these studies using transgenic mice that express human CRBN, biomarkers provide important information to the researchers and guide them in designing and developing safe and effective therapeutics. Detectable increase or decrease in certain biomarkers are observed in subjects with particular diseases (e.g., cancer), who are responsive to a given treatment (e.g., a compound, or a stereoisomer or a mixture of stereoisomers, tautomer, pharmaceutically acceptable salt, solvate, isotopologue, prodrug, hydrate, co-crystal, clathrate, or a polymorph thereof), and that the levels of these biomarkers can be used for monitoring the responsiveness of the subjects to the treatment.

A "biological marker" or "biomarker" is a substance, the change and/or the detection of which indicates a particular biological state. In some embodiments, the indication is the responsiveness of a disease (e.g., cancer), to a given treatment (e.g., a compound, or a pharmaceutically acceptable salt, solvate, stereoisomer, isotopologue, prodrug, hydrate, co-crystal, clathrate, or a polymorph thereof).

In certain embodiments of the various methods provided herein, the biomarker is a protein that is directly or indirectly affected by cereblon (CRBN), for example through protein-protein interactions (e.g., certain CRBN substrates or downstream effectors thereof), or through various cellular pathways (e.g., signal transduction pathways). In specific embodiments, the biomarker is a CRBN-associated protein (CAP). In some embodiments, the biomarker is mRNA of a protein that is directly or indirectly affected by CRBN. In other embodiments, the biomarker is cDNA of a protein that is directly or indirectly affected by CRBN. In certain embodiments, the biomarker is directly or indirectly affected by one or more isoforms of CRBN. In some embodiments, the biomarker is directly or indirectly affected by one but not other isoforms of CRBN.

Each of the biomarkers provided herein includes various isoforms, phosphorylated forms, cleaved forms, modified forms, and splicing variants thereof.

In some embodiments, the biomarker provided herein is selected from the group consisting of eRF3a (GSPT-1), eRF3b, eRF3c, IKZF1 (Ikaros), IKZF3 (Aiolos), CK1a, PABP1, eRF1, BIP, eEF1α, PERK, GCN2, eIF2a, ATF4, ATF3, DDIT3, PPP1R15A, TNFRSF10B, GADD45A, TNFRSF1A, TNFRSF1B, FAS, FADD, IRE1, XBP1, SEC24D, DNAJB9, EDEM1, EDEM2, HYOU1, ATF6, HSPA5, Caspase 8, BID, Caspase 9, Caspase 7, Caspase 3, PARP, Mcl-1, and BAD.

In certain embodiments, the biomarker is CDKN1A, Myc, IRF4, IRF7, IFIT1, IFIT3, RIG-I, MDA-5, TBK1, IKKe, ZFP91, ZNF198, MVP, Parp4, Ron, PDE6D, TLR3, STAT1, STAT2, STAT3, IFNa, IFNb, OAS1, OAS2, OAS3, IFIT2, ISG15, ISG20, IFI21, IFI35, IFI6, IFITM3, IFITM2WIZ, GBP2, GBP4, SELL, SNX20, KLF13, GBP1, MARCKS, SLAMF1, SASH1, or any combination thereof.

In other embodiments, the biomarker is ABCE1, ACLY, ACTB, ALDOA, ARID1A, C7ORF42, COPS6, CPSF6, CSNK1A1, CSNK2A1, CTPS, CRBN, DDB1, DDIT4, DDX17, DDX21, DDX58, DDX58, DDX60, DDX60L, DHX9, DNAJC1, DUT, EEF1A1, EEF1AL3, EEF1G, EIF2S1, E1F2S2, EIF3J, EIF4A1, EWSR1, FASN, FBXO21, FERMT3, FUBP1, G3BP1, G3BP2, GBE1, GBP1, GNAS, GNB2L1, GNB3, H2AFJ, H2AFX, H2AFZ, HIST1H1A, HIST1H1B, HIST1H1C, HIST1H1D, HIST1H1E, HIST1H2AA, HNRNPA2B1, HNRNPC, HNRNPH2, HNRNPR, HSPA1A, HSPA1B, HSPA8, HSPA9, IFI16, IFI27, IFI27L2, IFI35, IFI44, IFI44L, IFI6, IFIH1, IFIT1, IFIT2, IFIT3, IFIT5, IFITM2, IFITM3, IFN, IFNA16, IFNA5, IFNG, IFNGR1, IGF2BP2, IKKE, IKZF1 (Ikaros), IKZF3 (Aiolos), ILF3, IPO5, IRF1, IRF2, IRF3, IRF4, IRF7, IRF8, IRF9, ISG15, ISG20, KCNAB2, MACF1, MCM2, MCM1, MX1, MX2, MYH10, NACA, NAP1L2, NCL, NEDD8, NUP88, OAS1, OAS2, OAS3, OASL, PABPC1, PABPC4, PCM1, PDXK, PPAT, PRKDC, PTPRC, PTRH2, RPL10A, RPL11, RPL12, RPL13A, RPL14, RPL15, RPL18A, RPL19, RPL21, RPL3, RPL30, RPL4, RPL7, RPL7A, RPL9, RPLP1, RPLP2, RPS13, RPS16, RPS19, RPS2, RPS6, SEC23B, SEC24A, SEC24C, SMC4, SND1, a STAT, a STAT-PO4, STAT3, SYNCRIP, TBK1, TBK1-PO4, TBL1XR1, TLR1, TLR3, TLR4, TLR7, TLR8, TPD52, TUBA1A, TUBA1B, TUBA1C, UAP1, UBA52, UBAP2L, UBB, UBE2O, UBE2Q1, USP15, VAPA, XAF1, XRCC6, YWHAE, ZFP91, or any combination thereof.

In yet other embodiments, the biomarker is ARHGAP18, CASS4, CCNA2, CORO1B, CSNK1A1, CYTL1, DAB2, HSPB1, IKZF1, ITM2C, PPFIBP1, SERPINH1, YEATS2, ZFP91, or any combination thereof.

In still other embodiments, the biomarker is ARHGAP18, CALM1, CASS4, CCNA2, CORO1B, CSNK1A1, DAB2, HSPB1, IKZF1, ITM2C, PPFIBP1, SERPINH1, ZFP91, or any combination thereof.

In some embodiments, the biomarker is AHNAK, ALOX5, AMPD3, ANXA4, ANXA6, ATP2B4, BMF, BST2, C10orf76, C19orf66, CD36, CLN3, CNN3, CORO1B, CPNE2, CSRP2, CTNND1, CTSH, DAPK2, DDX58, DHX58, DLG2, DTX3L, EIF2AK2, EPB41L1, ETV6, EXTL2, F13A1, FAM65B, FCGR2B, FES, FMNL3, GBP1, GMFG, GMPR, HIP1, HLA-B, HLA-DMA, HPSE, ID3, IFI35, IFIH1, IFIT1, IFIT3, IFIT5, IFITM2, IL4I1, IRF7, IRF9, ISG15, ISG20, ITGB7, JAK3, LAP3, LGALS1, LGALS3BP, LIMD1, MAN2A2, MARCKS, MFI2, MGARP, MOV10, MPP7, MUC1, MX1, MX2, MYO1G, NCF2, NME3, NMI, NT5C3A, OAS1, OAS2, OAS3, PARP14, PARP9, PBXIP1, PLD4, PLEKHO1, PLSCR1, PLXNB2, POMP, PPFIBP1, PTMS, QPRT, RAB13, RCN1, RGCC, RNF213, S100A13, SAMD9L, SAMHD1, SERPINH1, SLFN11, SLFN13, SLFN5, SP110, SP140, SPN, SPR, STAP1, STAT1, STAT2, TAP1, TAX1BP3, THEMIS2, THTPA, TNFAIP8L2, TNFSF8, TP53I3, TREX1, TRIM22, TTC39C, TXNIP, UBA7, UBE2L6, USP41, VCL, VNN2, ZBTB38, ARHGAP19, ASNS, ASPM, B4GALT3, BANK1, BCDIN3D, BLZF1, CA2, CA8, CAMSAP3, CCDC69, CCNB1, CDC7, CDCA3, CENPF, CSNK1A1, DHPS, DLGAP5, DOK3, ECT2, EFCAB4B, EHMT1, EHMT2, EPCAM, ESRP1, FAM195A, FBRSL1, FHOD1, FIGNL1, GPT2, GRAMD1A, GRAMD1B, GRPEL2, HJURP, HMCES, HMMR, HOXC4, ICAM2, IKZF1, IKZF3, IRS2, KIF18B, KIF22, KIF2C, LIPG, LPXN, MINA, MIS18BP1, NEIL 1, NFKBID, NPIPB5, OMA1, ORC6, PARVB, PBK, PDE6D, PKMYT1, PLK1, PODXL, PODXL2, POLE2, PRDM15, PRNP, PTAFR, PTTG1, PYROXD1, RASA4B, RASSF6, RGS1, RGS2, SEC14L1, SGOL1, SGOL2, SLCO3A1, SLCO4A1, TACC3, TIMM8B, TOP2A, TPX2, TRIB3, WIZ, WSB1, WWC1, ZFP91, ZMYM2, ZNF385B, ZNF581, ZNF644, or any combination thereof.

In one embodiment, the biomarker is ADAM19, AIF1, ALDH1A1, ALDH2, ALOX5, AMPD3, APOBEC3G, APOE, APOH, ARHGAP10, ATP2B4, BST2, C4A, C4BPA, C4orf33, biomarkerN2, CASP4, CCR7, CD1D, CD63, CD86, CDR2, CORO1B, CPNE2, CYTH4, DAPK2, DDX58, DDX60, DDX60L, DHX58, DNASE1L3, DTX3L, EIF2AK2, ELOVL7, EPB41L1, F13A1, FAM129A, FBLN1, FCRLA, FERMT3, FGD6, FLNA, GALNT7, GBP1, GBP2, GBP4, GIPC1, GPD1, GPX3, HABP2, HBA1, HBD, HERC3, HERC6, HGF, HIGD1A, HMOX1, HSPA8, HSPB1, IFI35, IFI44, IFI44L, IFIH1, IFIT1, IFIT2, IFIT3, IFIT5, IFITM3, IL3RA, IRF7, IRF9, ISG15, ISG20, ITGA1, ITGB3, ITGB7, ITPKB, KIAA1618, L1TD1, LAP3, LDB3, LGALS1, LGALS3BP, LGALS9, LGALS9B, LMNA, LPIN1, MAP3K11, MCAM, MCM8, MGLL, MPP7, MUC1, MX1, MX2, MYL4, NCF4, NMI, NQO1, NUB1, OAS1, OAS2, OAS3, OASL, ORMDL2, OTOF, P2RY6, PAPSS2, PARP14, PARP9, PBXIP1, PHF11, PHF15, PLG, PLSCR1, PREX1, PREX2, PRIC285, PRKCI, PSAP, PTMS, RAB13, RASSF4, RCN1, RGL1, RGS13, RNF213, RTN2, RTP4, RUNX3, S100A13, SAMD9, SAMD9L, SAMHD1, SERPINA7, SERPINF2, SERPINH1, SIPA1L3, SLAMF1, SLC1A3, SLC23A2, SLC27A3, SLFN5, SOD2, SPN, SPR, SRC, STAT1, STAT2, SYNJ2BP, TAX1BP3, TBC1D13, TDRD7, TGOLN2, TLR7, TMEM87A, TMOD2, TNFAIP2, TNFAIP8L2, TRANK1, TRIM14, TRPC4, TRPM4, TSPAN14, TSPAN3, UBA7, UBE2L6, USP18, USP41, VNN2, VTN, XAF1, ZCCHC2, ZER1, ZNF385A, ZNF480, ZNF770, 3-Sep, ADIPOR2, AHR, ALCAM, ALDOC, ALKBH6, ALPL, AP1S3, APBB1IP, ARHGAP24, ARHGAP27, ARNT, BCL11A, BCL2A1, BCL2L1, BCLAF1, BNIP3L, C19orf22, C9orf40, CANX, CD22, CD44, CD5, CDC42SE2, CENPJ, CEP97, CFLAR, CLDN23, CLEC17A, COX17, CROCC, CRYM, CSNK1A1, DBN1, DENND1C, DNM2, DOK3, DTWD1, EHD1, EIF4H, ENO2, EPHA4, EPHA7, EPHB1, ERCC6, ETS1, EVI2B, EVL, FAR1, FCRL2, FCRL3, FCRL5, GABPB1, GAMT, GAPT, GAS7, GATM, GLRX, GNG2, GRPEL2, GYPC, GZMB, HK2, HLTF, HTRA3, IFNAR2, IKZF1, IKZF3, IL16, INF2, IQSEC1, IRF4, ISYNA1, ITGAL, ITGB2, KDM5B, KHK, L1CAM, LAT2, LBH, LNX1, LRRC25, LUC7L, LYSMD2, MEF2B, MEF2D, MICAL3, MYH11, NARF, NBR1, NEDD9, NEFL, OMA1, PARVB, PDK1, PFKFB4, PGM1, PIR, PLEKHG1, PMS2CL, PODXL2, POU2AF1, PPP1R2, PTPR, PTPRE, PTPRF, PTPRO, PTTG1, PVRL1, RAB33A, RANBP3, RASGRP3, RASSF6, RBBP5, RHOF, RPS29, RPS4Y2, SAMD1, SC5DL, SEC14L1, SEMA7A, SERPINB9, SETD8, SH2D3C, SIT1, SLAMF7, SLC16A3, SLC19A2, SNAP23, SNX11, SP140, SPIB, SPTAN1, SPTB, SSBIP1, STK17B, SYNCRIP, TCP11L1, TGM2, TJAP1, TNFAIP3, TNFRSF13B, TNFRSF1B, TOM1, TOR1AIP1, TP53I11, TSTD1, TUBB2B, UBE2J1, VAT1, VIM, WIPF1, WIZ, ZBTB32, ZFP91, ZMYM2, ZNF316, ZNF644, ZNF805, or any combination thereof.

In some embodiments, the biomarker is ACSS1, ACY3, ADAM19, ADCY7, AIF1, ALDH2, AMPD3, ANK3, ANXA4, ANXA6, ANXA6, APOBEC3G, APOBR, B2M, BCL9L, BST2, C19orf66, CASP10, CCDC28B, CD40, CD59, CD83, CGN, CLSTN1, CMPK2, COL23A1, CORO1B, CORO1C, CTNND1, CTSH, CTTNBP2NL, CYTH1, CYTH4, DDX58, DDX60, DTX3L, EIF2AK2, ETHE1, F11R, FADS2, FAM76A, FDFT1, FGD4, FLNA, FLNB, FRRS1, FSCN1, GCH1, GMFG, GNB4, GNG2, H1F0, HECTD1, HELZ2, HGF, HGSNAT, HLA-A, HLA-B, HLA-G, HSPB1, HYI, IFI35, IFIT1, IFIT3, IFIT5, IL4I1, IPCEF1, IRF9, ISG15, ISG20, JADE2, KIAA0101, LAT2, LGALS1, LGALS3BP, LGALS9, LGALS9B, LMCD1, LMNA, LY75, LYSMD2, MAGED4, MAPK10, MBD1, MEA1, MT2A, MX1, MX2, MYBPC2, NCOA7, NCOA7, NEXN, NT5C3A, OAS1, OAS2, OAS3, OSBPL10, PARP10, PARP14, PARP9, PCDHGC3, PLG, PLSCR1, PRCP, PTTG1IP, PYGO2, QPCT, S100A13, SAMHD1, SERPINH1, SIRPB1, SLC23A2, SLC25A33, SLC7A7, SLFN5, SOWAHD, SP110, SP140, SPR, STAT1, STAT2, STK3, SYBU, TAP1, TAP2, TDRD7, THEMIS2, TNFAIP8L2, TNFSF9, TRIM14, TRIM21, TRIM22, TYMP, UBE2L6, USP40, VPREB1, ADIPOR2, ATF5, BACH2, BANK1, BCDIN3D, CD320, CSNK1A1, DEPTOR, ETS1, GLIPR1L1, GNG7, GPT2, HSBP1, ICAM2, IKZF1, IKZF3, KRT1, KRT14, KRT2, KRT6B, KRT9, MED12L, NEIL 1, NUGGC, OMA1, PDE6D, PDZRN3, PODXL, SYNGR3, SYTL1, WIZ, ZFP91, ZMYM2, or any combination thereof.

In other embodiments, the biomarker is ADIPOR2, ATF5, BACH2, BANK1, BCDIN3D, CD320, CSNK1A1, DEPTOR, ETS1, GLIPR1L1, GNG7, GPT2, HSBP1, ICAM2, IKZF1, IKZF3, KRT1, KRT14, KRT2, KRT6B, KRT9, MED12L, NEIL 1, NUGGC, OMA1, PDE6D, PDZRN3, PODXL, SYNGR3, SYTL1, WIZ, ZFP91, ZMYM2, or any combination thereof.

In certain embodiments, the biomarker is AMPK, CUL4A, CUL4B, DDB1, DDB2, DUS3L, FAS1, GSK3B, IRF4, NFkB, PHGDH, RANBP6, XBP-1, or any combination thereof.

In some embodiments, the biomarker is a mouse equivalent of any of the above mentioned biomarker.

In some embodiments, the biomarker measured comprises one biomarker. In certain embodiments, the biomarkers measured comprise two biomarkers. In other embodiments, the biomarkers measured comprise three biomarkers. In certain embodiments, the biomarkers measured comprise four biomarkers. In some embodiments, the biomarkers measured comprise five biomarkers. In other embodiments, the biomarkers measured comprise six biomarkers. In yet other embodiments, the biomarkers measured comprise seven biomarkers. In certain embodiments, the biomarkers measured comprise eight biomarkers. In other embodiments, the biomarkers measured comprise nine biomarkers. In another embodiment, the biomarkers measured comprise ten or more biomarkers.

In certain embodiments, provided herein are methods of detecting and quantifying the protein level of biomarker, such as CRBN or a protein that is directly or indirectly affected by CRBN, from a biological sample, comprising contacting proteins within the sample with a first antibody that immunospecifically binds to the biomarker protein. In some embodiments, the methods provided herein further comprise (i) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody; (ii) detecting the presence of the second antibody bound to the biomarker protein; and (iii) determining the amount of the biomarker protein based on the amount of detectable label in the second antibody. In other embodiments, the methods provided herein further comprise (i) contacting the biomarker protein bound to the first antibody with a second antibody with a detectable label, wherein the second antibody immunospecifically binds to the first antibody; (ii) detecting the presence of the second antibody bound to the first antibody; and (iii) determining the amount of the biomarker protein based on the amount of detectable label in the second antibody.

In some embodiments of the various methods provided herein, the method comprises using dual staining immunohistochemistry to determine the level of a biomarker, such as CRBN or a protein that is directly or indirectly affected by CRBN. In a dual staining immunohistochemistry assay, a biomarker provided herein and another disease-specific biomarker (e.g., cancer biomarker) are simultaneously detected using a first labeled antibody targeting a biomarker provided herein and a second labeled antibody targeting a cancer biomarker. Such assay can improve the specificity, accuracy, and sensitivity for detecting and measuring a biomarker provided herein. In certain embodiments, the cancer biomarker is a solid cancer biomarker. In other embodiments, the cancer biomarker is a blood cancer biomarker. In some embodiments, the cancer biomarker is a lymphoma biomarker. In other embodiments, the cancer biomarker is a leukemia biomarker. In yet other embodiments, the cancer biomarker is a multiple myeloma biomarker.

Thus, in some embodiments, the method provided herein comprises (i) contacting proteins within a sample with a first antibody that immunospecifically binds to a biomarker provided herein, the first antibody being coupled with a first detectable label; (ii) contacting the proteins within the sample with a second antibody that immunospecifically binds to a cancer biomarker, the second antibody being coupled with a second detectable label; (iii) detecting the presence of the first antibody and the second antibody bound to the proteins; and (iv) determining the level of the biomarker provided herein based on the amount of detectable label in the first antibody, and determining the level of the cancer biomarker based on the amount of detectable label in the second antibody. In certain embodiments, the cancer biomarker is a solid cancer biomarker. In other embodiments, the cancer biomarker is a blood cancer biomarker. In some embodiments, the cancer biomarker is a lymphoma biomarker. In other embodiments, the cancer biomarker is a leukemia biomarker. In yet other embodiments, the cancer biomarker is a multiple myeloma biomarker.

In certain embodiments, provided herein are methods of detecting and quantifying the RNA (e.g., mRNA) level of a biomarker, such as CRBN or a biomarker provided herein, from a biological sample, comprising: (a) obtaining RNA from the sample; (b) contacting the RNA with a primer that specifically binds to a sequence in the RNA to generate a first DNA molecule having a sequence complementary to said RNA; (c) amplifying the DNA corresponding to a segment of a gene encoding the biomarker; and (d) determining the RNA level of the biomarker based on the amount of the amplified DNA.

In some embodiments, the biomarker(s) are evaluated in combination with other biomarker(s) provided herein, such as CRBN, eRF3a, eRF3b, eRF3c, ATF4, ATF3, and DDIT3.

In certain embodiments of the various methods provided herein, the two or more of the steps are performed sequentially. In other embodiments of the methods provided herein, two or more of steps are performed in parallel (e.g., at the same time).

Exemplary assays provided herein for the methods of detecting and quantifying the protein level of a biomarker, such as eRF3a, eRF3b, eRF3c, IKZF1, IKZF3, CK1a, PABP1, eRF1, BIP, eEF1α, PERK, GCN2, eIF2a, ATF4, ATF3, DDIT3, PPP1R15A, TNFRSF10B, GADD45A, TNFRSF1A, TNFRSF1B, FAS, FADD, IRE1, XBP1, SEC24D, DNAJB9, EDEM1, EDEM2, HYOU1, ATF6, HSPA5, Caspase 8, BID, Caspase 9, Caspase 7, Caspase 3, PARP, Mcl-1, BAD, CDKN1A, Myc, IRF4, IRF7, IFIT1, IFIT3, RIG-I, MDA-5, TBK1, IKKe, ZFP91, ZNF198, MVP, Parp4, Ron, PDE6D, TLR3, STAT1, STAT2, STAT3, IFNa, IFNb, OAS1, OAS2, OAS3, IFIT2, ISG15, ISG20, IFI21, IFI35, IFI6, IFITM3, IFITM2WIZ, GBP2, GBP4, SELL, SNX20, KLF13, GBP1, MARCKS, SLAMF1, SASH1, or a combination thereof, are immunoassays, such as western blot analysis and enzyme-linked immunosorbent assay (ELISA) (e.g., a sandwich ELISA). An exemplary assay provided herein for the methods of detecting and quantifying the RNA level of a biomarker, such as eRF3a, eRF3b, eRF3c, IKZF1, IKZF3, CK1a, PABP1, eRF1, BIP, eEF1α, PERK, GCN2, eIF2a, ATF4, ATF3, DDIT3, PPP1R15A, TNFRSF10B, GADD45A, TNFRSF1A, TNFRSF1B, FAS, FADD, IRE1, XBP1, SEC24D, DNAJB9, EDEM1, EDEM2, HYOU1, ATF6, HSPA5, Caspase 8, BID, Caspase 9, Caspase 7, Caspase 3, PARP, Mcl-1, and BAD, CDKN1A, Myc, IRF4, IRF7, IFIT1, IFIT3, RIG-I, MDA-5, TBK1, IKKe, ZFP91, ZNF198, MVP, Parp4, Ron, PDE6D, TLR3, STAT1, STAT2, STAT3, IFNa, IFNb, OAS1, OAS2, OAS3, IFIT2, ISG15, ISG20. IFI21, IFI35, IFI6, IFITM3, IFITM2WIZ, GBP2, GBP4, SELL, SNX20, KLF13, GBP1, MARCKS, SLAMF1, SASH1, or a combination thereof, is reverse transcription polymerase chain reaction (RT-PCR), e.g., quantitative RT-PCR (qRT-PCR).

5.4.2 Treatment Compounds

Various compounds provided herein contain one or more chiral centers, and can exist as mixtures of enantiomers (e.g., racemic mixtures) or mixtures of diastereomers. The methods provided herein encompass the use of stereomerically pure forms of such compounds as well as mixtures of those forms. For example, mixtures comprising equal or unequal amounts of the enantiomers of a particular compound may be used in methods provided herein. These isomers may be asymmetrically synthesized or resolved using standard techniques, such as chiral columns or chiral resolving agents. See, Jacques et al., *Enantiomers, Racemates and Resolutions* (Wiley-Interscience, New York, 1981); Wilen et al., *Tetrahedron* 1977, 33:2725-2736; Eliel, *Stereochemistry of Carbon Compounds* (McGraw-Hill, N Y, 1962); Wilen, *Tables of Resolving Agents and Optical Resolutions*, p. 268 (Eliel, ed., Univ. of Notre Dame Press, Notre Dame, IN, 1972).

In certain embodiments, the compound provided herein is a CRBN E3 ubiquitin ligase modulating compound (CMC), which directly or indirectly modulating the CRBN E3 ubiquitin ligase complex. In some embodiments, the CMC can bind directly to CRBN. In other embodiments, the CMC can induce conformational change in the CRBN protein. In yet other embodiments, the CMC can bind directly to CRBN and induce conformational change in the CRBN protein. In still other embodiments, the CMC can bind directly to other subunits in the CRBN E3 ubiquitin ligase complex.

In some embodiments, the compound provided herein is an immunomodulatory compounds (e.g., thalidomide, lenalidomide, or pomalidomide). In one embodiment, the compound provided herein is thalidomide. In another embodiment, the compound provided herein is lenalidomide. In yet another embodiment, the compound provided herein is pomalidomide.

In certain embodiments, the CMC provided herein is an immunomodulatory compound. In other embodiments, the CMC provided herein is not an immunomodulatory compound. In some embodiments, the immunomodulatory compound provided herein is a CMC. In other embodiments, the immunomodulatory compounds provided herein is not a CMC.

As used herein and unless otherwise indicated, the term "immunomodulatory compound" can encompass certain small organic molecules that inhibit LPS induced monocyte TNF-α, IL-1ß, IL-12, IL-6, MIP-1α, MCP-1, GM-CSF, G-CSF, and Cox-2 production.

Without being limited by a particular theory, one of the biological effects exerted by the immunomodulatory compounds disclosed herein is the reduction of myeloid cell TNF-α production. Immunomodulatory compounds disclosed herein may enhance the degradation of TNF-α mRNA.

Further, without being limited by theory, immunomodulatory compounds disclosed herein may also be potent co-stimulators of T cells and increase cell proliferation dramatically in a dose dependent manner. Immunomodulatory compounds disclosed herein may also have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

In other embodiments, the compound provided herein is selected from the group consisting of 3-(5-amino-2-methyl-4-oxo-4H-quinazolin-3-yl)-piperidine-2,6-dione ("Compound A"), which has the following structure:

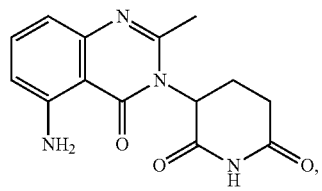 [SMILES: Cc1nc2cccc(N)c2c(=O)n1C1CCC(=O)NC1=O]

3-(4-((4-(morpholinomethyl)benzyl)oxy)-1-oxoisoindolin-2-yl)piperidine-2,6-dione ("Compound B"), which has the following structure:

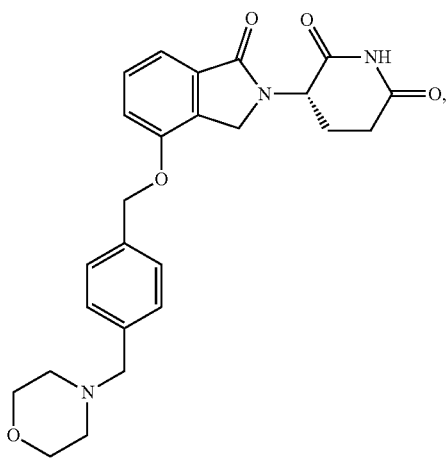 [SMILES: O=C1CC[C@H](N2Cc3c(OCc4ccc(CN5CCOCC5)cc4)cccc3C2=O)C(=O)N1]

1-(3-chloro-4-methylphenyl)-3-((2-(2,6-dioxopiperidin-3-yl)-1-oxoisoindolin-5-yl)methyl)urea ("Compound C"), which has the following structure:

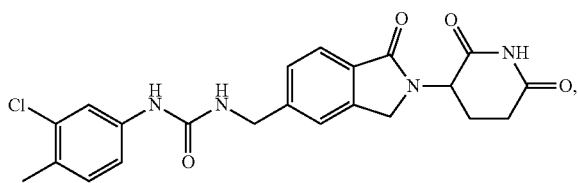 [SMILES: Cc1ccc(NC(=O)NCc2ccc3c(c2)CN(C2CCC(=O)NC2=O)C3=O)cc1Cl]

2-(4-chlorophenyl)-N-((2-(2,6-dioxopiperidin-3-yl)-1-oxoisoindolin-5-yl)methyl)-2,2-difluoroacetamide ("Compound D"), which has the following structure:

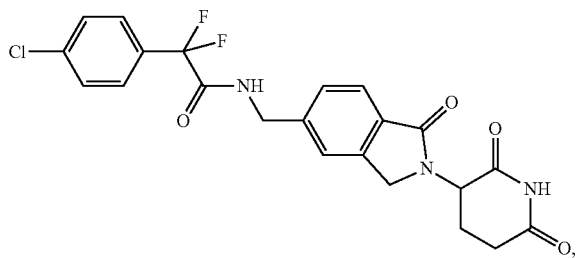 [SMILES: O=C1CCC(N2Cc3cc(CNC(=O)C(F)(F)c4ccc(Cl)cc4)ccc3C2=O)C(=O)N1]

and
2-(4-flurophenyl)-N-((2-(2,6-dioxopiperidin-3-yl)-1-oxoisoindolin-5-yl)methyl)-2,2-difluoroacetamide ("Compound E"), which has the following structure:

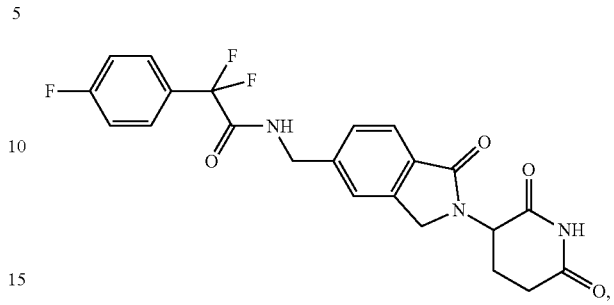

or a stereoisomer or a mixture of stereoisomers, tautomer, pharmaceutically acceptable salt, solvate, isotopologue, prodrug, hydrate, co-crystal, clathrate, or a polymorph thereof.

Compound A can be prepared as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Pat. No. 8,802,685, which is incorporated herein by reference in its entirety. In some embodiments, the hydrochloride salt of Compound A is used in the methods provided herein. Methods of treating, preventing and/or managing cancers and other diseases using Compound A are described in U.S. Pat. No. 8,906,932, which is incorporated herein by reference in its entirety.

Compound B and methods of preparing the same are described in U.S. Pat. No. 8,518,972, which is incorporated herein by reference in its entirety.

Compound C and methods of preparing the same are described in U.S. Pat. No. 8,877,780, which is incorporated herein by reference in its entirety.

Compounds D and E and methods of preparing the same are described in U.S. Pat. No. 9,499,514, which is incorporated herein by reference in its entirety.

In one embodiment, the compound provided herein is Compound A, or a stereoisomer or a mixture of stereoisomers, tautomer, pharmaceutically acceptable salt, solvate, isotopologue, prodrug, hydrate, co-crystal, clathrate, or a polymorph thereof. In another embodiment, the compound provided herein is Compound B, or a stereoisomer or a mixture of stereoisomers, tautomer, pharmaceutically acceptable salt, solvate, isotopologue, prodrug, hydrate, co-crystal, clathrate, or a polymorph thereof. In yet another embodiment, the compound provided herein is Compound C, or a stereoisomer or a mixture of stereoisomers, tautomer, pharmaceutically acceptable salt, solvate, isotopologue, prodrug, hydrate, co-crystal, clathrate, or a polymorph thereof. In still another embodiment, the compound provided herein is Compound D, or a stereoisomer or a mixture of stereoisomers, tautomer, pharmaceutically acceptable salt, solvate, isotopologue, prodrug, hydrate, co-crystal, clathrate, or a polymorph thereof. In again another embodiment, the compound provided herein is Compound E, or a stereoisomer or a mixture of stereoisomers, tautomer, pharmaceutically acceptable salt, solvate, isotopologue, prodrug, hydrate, co-crystal, clathrate, or a polymorph thereof.

In certain embodiments, the compound provided herein is a compound with increased anti-multiple myeloma activity, increased anti-B-cell malignancy activity, or enhanced immunomodulatory activity. In some embodiments, the compound has increased anti-multiple myeloma activity. In other embodiments, the compound has increased anti-B-cell malignancy activity. In yet other embodiments, the compound has enhanced immunomodulatory activity. In still other embodiments, the compound has increased anti-multiple myeloma activity and increased anti-B-cell malignancy activity. In certain embodiments, the compound has increased anti-multiple myeloma activity and enhanced immunomodulatory activity. In some embodiments, the compound has increased anti-B-cell malignancy activity and enhanced immunomodulatory activity. In other embodiments, the compound has increased anti-multiple myeloma activity, increased anti-B-cell malignancy activity, and enhanced immunomodulatory activity.

In some embodiments, the compound provided herein can also be an antibody or a fragment thereof. In certain embodiments, the compound provided herein is a monoclonal antibody. In other embodiments, the compound provided herein is a polyclonal antibody. In yet other embodiments, the compound provided herein is a humanized, human, or chimeric antibody. In one embodiment, the compound provided herein is a humanized antibody. In another embodiment, the compound provided herein is a human antibody. In yet another embodiment, the compound provided herein is a chimeric antibody. In still another embodiment, the compound provided herein is a deimmunized antibody. In one embodiment, the compound provided herein is a composite human antibody.

In certain embodiments, the compound provided herein is a Fab, a Fab', a F(ab')2, a Fv, a scFv, a dsFv, a diabody, a triabody, a tetrabody, or a multispecific antibody formed from antibody fragments.

In some embodiments, the compound provided herein is an antibody conjugated to an agent. In other embodiments, the compound provided herein is an antibody conjugated to an agent selected from the group consisting of a radioisotope, a metal chelator, an enzyme, a fluorescent compound, a bioluminescent compound, and a chemiluminescent compound.

In other embodiments of the various methods provided herein, the compound is an antibody. In some embodiments, the antibody is selected from the group consisting of PD-1 antibody, PD-L1 antibody, PD-L2 antibody, CTLA-4 antibody, CD38 antibody, and SLAMF7 antibody. In another embodiment, the antibody is PD-1 antibody. In another embodiment, the antibody is PD-L1 antibody. In yet another embodiment, the antibody is PD-L2 antibody. In still another embodiment, the antibody is CTLA-4 antibody. In one embodiment, the antibody is CD38 antibody. In another embodiment, the antibody is SLAMF7 antibody.

In some embodiments, the antibody is selected from the group consisting of nivolumab (i.e., BMS-936558, MDX-1106, ONO-4538), MK-3475 (i.e., pembrolizumab, lambrolizumab), pidilizumab (i.e., CT-011), MEDI-0680 (i.e., AMP-514), PDR-001, durvalumab (i.e., MEDI-4736), BMS-936559 (i.e., MDX-1105), avelumab (i.e., MSB0010718C), atezolizumab (i.e., MPDL-3280A), ipilimumab, daratumumab, and elotuzumab. In one embodiment, the antibody is nivolumab. In another embodiment, the antibody is MK-3475. In yet another embodiment, the antibody is pidilizumab. In still another embodiment, the antibody is MEDI-0680. In one embodiment, the antibody is PDR-001. In another embodiment, the antibody is durvalumab. In yet another embodiment, the antibody is BMS-936559. In still another embodiment, the antibody is avelumab. In one embodiment, the antibody is atezolizumab. In another embodiment, the antibody is ipilimumab. In yet another embodiment, the antibody is daratumumab. In still another embodiment, the antibody is elotuzumab.

In certain embodiments of the various methods provided herein, the compound is a Pattern Recognition Receptor (PRR) agonist. In some embodiments, the PRR agonist is selected from the group consisting of TLR3 agonist, TLR7 agonist, TLR8 agonist, TLR9 agonist, RIG-1 agonist, MDA5 agonist, and AIM2 agonist. In one embodiment, the PRR agonist is TLR3 agonist. In another embodiment, the PRR agonist is TLR7 agonist. In yet another embodiment, the PRR agonist is TLR8 agonist. In still another embodiment, the PRR agonist is TLR9 agonist. In one embodiment, the PRR agonist is RIG-1 agonist. In another embodiment, the PRR agonist is MDA5 agonist. In yet another embodiment, the PRR agonist is AIM2 agonist.

In yet other embodiments of the various methods provided herein, the compound is a molecular mimic. In some embodiments, the molecular mimic is selected from the group consisting of azacytidine, romidepsin, ATRA, cyclophosphamid, and Celebrex®. In one embodiment, the molecular mimic is azacytidine. In another embodiment, the molecular mimic is romidepsin. In yet another embodiment, the molecular mimic is ATRA. In still another embodiment, the molecular mimic is cyclophosphamid. In one embodiment, the molecular mimic is Celebrex®.

In still other embodiments of the various methods provided herein, the compound is an inhibitor of an enzyme (e.g., histone deacetylase (HDAC)) or a protein degradation apparatus (e.g., proteasome). In some embodiments, the compound is an inhibitor of a HDAC. In a particular embodiment, the compound is an inhibitor of HADC6. In a specific embodiment, the compound is ACY-241. In other embodiments, the compound is an inhibitor of a proteasome. In one embodiment, the compound is carfilzomib. In another embodiment, the compound is ixazomib.

In some embodiments, the compound is an anti-cancer compound. In certain embodiments, the compound is an anthracycline.

Various compounds provided herein can be used individually or in combination in any of the methods provided herein. In certain embodiments, various compounds provided herein are used individually in any of the methods provided herein. In other embodiments, various compounds provided herein are used in combination in any of the methods provided herein. In some embodiments, two of the compounds provided herein are used in combination. In certain embodiments, three of the compounds provided herein are used in combination. In other embodiments, four of the compounds provided herein are used in combination. In yet other embodiments, five of the compounds provided herein are used in combination. In still other embodiments, six or more of the compounds provided herein are used in combination.

In some embodiments of the methods provided herein, administering a treatment compound is performed in vitro (e.g., administering a compound to isolated cells, cell lines, tissues, or organs derived from transgenic mice). In other embodiments, administering a treatment compound is performed in vivo (e.g., administering a compound to transgenic mice). In one embodiment, the isolated cells, cell lines, tissues, or organs are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2, 3, or more days.

5.4.3 Methods for Optimizing Dosing Amounts and/or Schedules of Treatment Compounds In another aspect, provided herein is a method for optimizing dosing amounts and/or schedules of a compound in a transgenic mouse expressing human CRBN or a fragment thereof, comprising:

(a) administering the compound to the transgenic mouse;
(b) obtaining a sample from the transgenic mouse;
(c) measuring the level of a biomarker in the sample; and
(d) adjusting the dosing amount and/or schedule of the compound based on the level of the biomarker;
wherein the biomarker is a CRBN-associated protein (CAP).

In certain embodiments, the method is a method for optimizing dosing amounts. In other embodiments, the method is a method for optimizing dosing schedules. In certain embodiments, the method is a method for optimizing dosing schedules and dosing amounts. In certain embodiments, the transgenic mouse used herein comprises a nucleic acid sequence encoding human CRBN. In certain embodiments, the nucleic acid sequence encoding the human CRBN is stably integrated into a mouse chromosome. In other embodiments, the nucleic acid sequence encodes a fragment of human CRBN. In certain embodiments, the nucleic acid sequence encoding the fragment of the human CRBN is stably integrated into a mouse chromosome. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8.

In some embodiments of the various methods provided herein, the biomarker comprises a biomarker provided in Section 5.4.1. In certain embodiments, the dosing amount of the compound is adjusted if the level of the biomarker is higher than a base level of the biomarker. In other embodiments, the dosing schedule of the compound is adjusted if the level of the biomarker is higher than a base level of the biomarker. In other embodiments, both the dosing amount and the dosing schedule of the compound are adjusted if the level of the biomarker is higher than a base level of the biomarker. In certain embodiments, the dosing amount of the compound is adjusted if the level of the biomarker is lower than a base level of the biomarker. In other embodiments, the dosing schedule of the compound is adjusted if the level of the biomarker is lower than a base level of the biomarker. In other embodiments, both the dosing amount and the dosing schedule of the compound are adjusted if the level of the biomarker is lower than a base level of the biomarker.

In some embodiments, the base level of the biomarker is an arbitrary level determined by scientists. In other embodiments, the base level of the biomarker is an empirical level based on prior measurement. In certain embodiments, the base level of the biomarker is an average or a mean level based on two or more prior measurements. In some embodiments, the base level of the biomarker is the level of the biomarker in a sample from a mouse that does not carry a human CRBN transgene. In other embodiments, the base level of the biomarker is the level of the biomarker in a sample from a mouse that expresses a human CRBN transgene. In yet other embodiments, the base level of the biomarker is the level of the biomarker in a sample from a transgenic mouse expressing human CRBN that has not been treated by a compound. In still other embodiments, the base level of the biomarker is the level of the biomarker in a sample from a transgenic mouse expressing human CRBN that has been treated by a compound.

In some embodiments, the biomarker measured comprises one biomarker. In certain embodiments, the biomarkers measured comprise two or more biomarkers. In some embodiments, the levels of the biomarkers are measured by detecting and quantifying the protein levels of the biomarkers. In other embodiments, the levels of the biomarkers are measured by detecting and quantifying the nucleic acid levels of the biomarkers. In one embodiment, the levels of the biomarkers are measured by detecting and quantifying the cDNA levels of the biomarkers. In another embodiment, the levels of the biomarkers are measured by detecting and quantifying the mRNA levels of the biomarkers. Any suitable methods of measuring biomarkers provided herein or well know in the art can be used to detect and quantify the levels of the biomarkers.

To transgenic mice, a treatment compound provided herein, or a stereoisomer or a mixture of stereoisomers, tautomer, pharmaceutically acceptable salt, solvate, isotopologue, prodrug, hydrate, co-crystal, clathrate, or a polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The treatment compound, or a stereoisomer or a mixture of stereoisomers, tautomer, pharmaceutically acceptable salt, solvate, isotopologue, prodrug, hydrate, co-crystal, clathrate, or a polymorph thereof, may be formulated, alone or together, in suitable dosage unit with pharmaceutically acceptable excipients, carriers, adjuvants, and vehicles, appropriate for each route of administration.

In one embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered orally. In another embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered parenterally. In yet another embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered intravenously.

The treatment compounds used herein are any compounds disclosed in Section 5.4.2.

In certain embodiments, the compound used is a CMC, which directly or indirectly modulating the CRBN E3 ubiquitin ligase complex. In some embodiments, the CMC can bind directly to CRBN. In other embodiments, the CMC can induce conformational change in the CRBN protein. In yet other embodiments, the CMC can bind directly to CRBN and induce conformational change in the CRBN protein. In still other embodiments, the CMC can bind directly to other subunits in the CRBN E3 ubiquitin ligase complex.

In some embodiments, the compound used is an immunomodulatory compounds (e.g., thalidomide, lenalidomide, or pomalidomide). In one embodiment, the compound provided herein is thalidomide. In another embodiment, the compound provided herein is lenalidomide. In yet another embodiment, the compound provided herein is pomalidomide.

In other embodiments, the compound used is a compound selected from the group consisting of 3-(5-amino-2-methyl-4-oxo-4H-quinazolin-3-yl)-piperidine-2,6-dione ("Compound A"), which has the following structure:

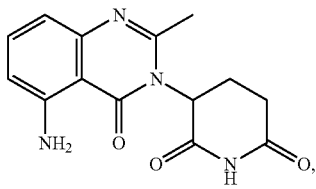 [SMILES: Cc1nc2cccc(N)c2c(=O)n1C1CCC(=O)NC1=O]

3-(4-((4-(morpholinomethyl)benzyl)oxy)-1-oxoisoindolin-2-yl)piperidine-2,6-dione ("Compound B"), which has the following structure:

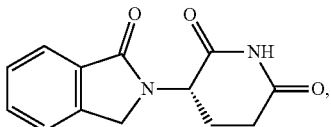

1-(3-chloro-4-methylphenyl)-3-((2-(2,6-dioxopiperidin-3-yl)-1-oxoisoindolin-5-yl)methyl)urea ("Compound C"), which has the following structure:

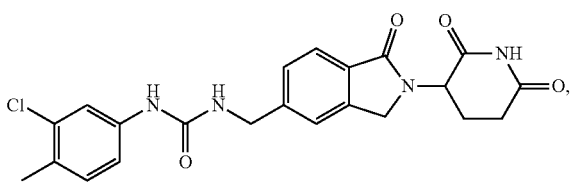 [SMILES: Cc1ccc(NC(=O)NCc2ccc3c(c2)CN(C2CCC(=O)NC2=O)C3=O)cc1Cl]

2-(4-chlorophenyl)-N-((2-(2,6-dioxopiperidin-3-yl)-1-oxoisoindolin-5-yl)methyl)-2,2-difluoroacetamide ("Compound D"), which has the following structure:

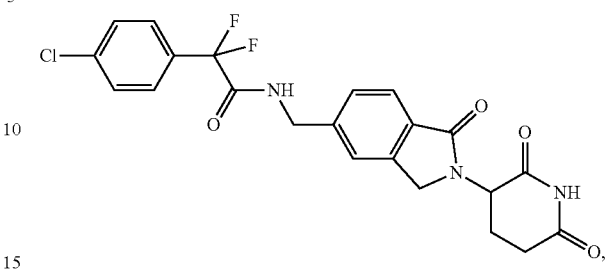

and
2-(4-flurophenyl)-N-((2-(2,6-dioxopiperidin-3-yl)-1-oxoisoindolin-5-yl)methyl)-2,2-difluoroacetamide ("Compound E"), which has the following structure:

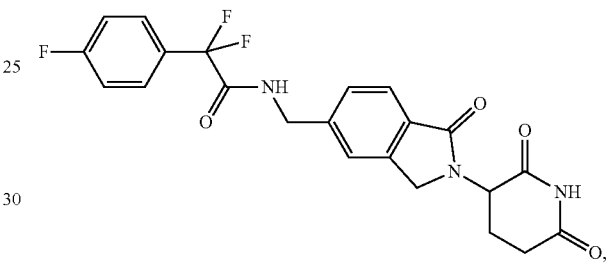

or a stereoisomer or a mixture of stereoisomers, tautomer, pharmaceutically acceptable salt, solvate, isotopologue, prodrug, hydrate, co-crystal, clathrate, or a polymorph thereof.

In one embodiment, the compound used is Compound A, or a stereoisomer or a mixture of stereoisomers, tautomer, pharmaceutically acceptable salt, solvate, isotopologue, prodrug, hydrate, co-crystal, clathrate, or a polymorph thereof. In another embodiment, the compound used is Compound B, or a stereoisomer or a mixture of stereoisomers, tautomer, pharmaceutically acceptable salt, solvate, isotopologue, prodrug, hydrate, co-crystal, clathrate, or a polymorph thereof. In yet another embodiment, the compound used is Compound C, or a stereoisomer or a mixture of stereoisomers, tautomer, pharmaceutically acceptable salt, solvate, isotopologue, prodrug, hydrate, co-crystal, clathrate, or a polymorph thereof. In still another embodiment, the compound used is Compound D, or a stereoisomer or a mixture of stereoisomers, tautomer, pharmaceutically acceptable salt, solvate, isotopologue, prodrug, hydrate, co-crystal, clathrate, or a polymorph thereof. In again another embodiment, the compound used is Compound E, or a stereoisomer or a mixture of stereoisomers, tautomer, pharmaceutically acceptable salt, solvate, isotopologue, prodrug, hydrate, co-crystal, clathrate, or a polymorph thereof.

In one embodiment, the treatment compound is Compound A or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1. In another embodiment, the treatment compound is Compound B or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1. In still another embodiment, the treatment compound is Compound C or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1. In yet another embodiment, the treatment compound is Compound D or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1. In one embodiment, the treatment compound is Compound E or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1.

In certain embodiments, the amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, the amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the amount of the compound is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the daily dose range of a compound, or a stereoisomer or a mixture of stereoisomers, tautomer, pharmaceutically acceptable salt, solvate, isotopologue, prodrug, hydrate, co-crystal, clathrate, or a polymorph thereof, for the conditions described herein lie within the range of from about 0.5 mg to about 50 mg per day, for example given as a single once-a-day dose, or in divided doses throughout a day. In some embodiments, the dosage ranges from about 1 mg to about 50 mg per day. In other embodiments, the dosage ranges from about 0.5 mg to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg per day.

In a specific embodiment, the recommended starting dosage may be 0.5, 1, 2, 3, 4, 5, 10, 15, 20, 25, or 50 mg per day. In another embodiment, the recommended starting dosage may be 0.5, 1, 2, 3, 4, or 5 mg per day. The dose may be escalated to 15, 20, 25, 30, 35, 40, 45, or 50 mg/day.

In certain embodiments, the amount of the compound is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m2/day. One of ordinary skill in the art would readily know how to convert doses from mg/kg/day to mg/m2/day to given either the height or weight of a subject or both (see, www.fda.gov/cder/cancer/animalframe.htm).

In certain embodiments, the amount of the compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM, or from about 50 to about 100 nM.

As used herein, the term "plasma concentration at steady state" is the concentration reached after a period of administration of a compound provided herein, or a stereoisomer or a mixture of stereoisomers, tautomer, pharmaceutically acceptable salt, solvate, isotopologue, prodrug, hydrate, co-crystal, clathrate, or a polymorph thereof. Once steady state is reached, there are minor peaks and troughs on the time-dependent curve of the plasma concentration of the compound.

In certain embodiments, the amount of the compound administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the compound administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

The treatment compound, or a stereoisomer or a mixture of stereoisomers, tautomer, pharmaceutically acceptable salt, solvate, isotopologue, prodrug, hydrate, co-crystal, clathrate, or a polymorph thereof, can be delivered as a single dose (e.g., a single bolus injection), or over time (e.g., divided bolus doses over time). The compound can be administered repeatedly if necessary, for example, until the mice experience some detectable stable biological effects, or until the mice experience disease progression or unacceptable toxicity. Stable disease or lack thereof is determined by methods known in the art such as evaluation of mice symptoms, measurement of biomarkers, and visualization of the tumor that has been imaged using X-ray, CAT, PET, MRI scan, or other commonly accepted evaluation modalities.

The treatment compound, or a stereoisomer or a mixture of stereoisomers, tautomer, pharmaceutically acceptable salt, solvate, isotopologue, prodrug, hydrate, co-crystal, clathrate, or a polymorph thereof, can be administered once daily (QD) or divided into multiple daily doses such as twice daily (BID), three times daily (TID), and four times daily (QID). In addition, the administration can be continuous (i.e., daily for consecutive days or every day) or intermittent, e.g., in cycles (i.e., including days, weeks, or months of rest without drug). As used herein, the term "daily" is intended to mean that a therapeutic compound, or a stereoisomer or a mixture of stereoisomers, tautomer, pharmaceutically acceptable salt, solvate, isotopologue, prodrug, hydrate, co-crystal, clathrate, or a polymorph thereof, is administered once or more than once each day, for example, for a period of time. The term "continuous" is intended to mean that a therapeutic compound, or a stereoisomer or a mixture of stereoisomers, tautomer, pharmaceutically acceptable salt, solvate, isotopologue, prodrug, hydrate, co-crystal, clathrate, or a polymorph thereof, is administered daily for an uninterrupted period of at least 10 days to 52 weeks. The term "intermittent" or "intermittently" as used herein is intended to mean stopping and starting at either regular or irregular intervals. For example, intermittent administration of the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administration for one to six days per week, administration in cycles (e.g., daily administration for two to eight consecutive weeks, then a rest period with no administration for up to one week), or administration on alternate days. The term "cycling" as used herein is intended to mean that a treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered daily or continuously but with a rest period. In certain embodiments, the rest period is the same length as the treatment period. In other embodiments, the rest period has different length from the treatment period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered once a day. In another embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered twice a day. In yet another embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered three times a day. In still another embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered four times a day.

In certain embodiments, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered once per day from one day to six months, from one week to three months, from one week to four weeks, from one week to three weeks, or from one week to two weeks. In certain embodiments, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered once per day for one week, two weeks, three weeks, or four weeks. In one embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered once per day for one week. In another embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered once per day for two weeks. In yet another embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered once per day for three weeks. In still another embodiment, the treatment compound, or a stereoisomer or a mixture of stereoisomers, tautomer, pharmaceutically acceptable salt, solvate, isotopologue, prodrug, hydrate, co-crystal, clathrate, or a polymorph thereof, is administered once per day for four weeks.

Also provided herein are methods for optimizing dosing amounts and/or schedules of a treatment compound in a transgenic mouse expressing human CRBN, comprising:
(a) administering the compound to the transgenic mouse expressing human CRBN;
(b) observing the physical appearance of the transgenic mouse; and
(c) adjusting the dosing amounts and/or schedule of the compound if the physical appearance of the transgenic mouse expressing human CRBN does or does not meet a standard.

In certain embodiments of the various methods provided herein, the two or more of the steps are performed sequentially. In other embodiments of the methods provided herein, two or more of steps are performed in parallel (e.g., at the same time).

In certain embodiments, the dosing amount of the compound is adjusted if the physical appearance of the transgenic mouse meets a standard. In some embodiments, the dosing schedule of the compound is adjusted if the physical appearance of the transgenic mouse meets a standard. In other embodiments, the dosing amount and the schedule of the compound are adjusted if the physical appearance of the transgenic mouse meets a standard. In certain embodiments, the dosing amount of the compound is adjusted if the physical appearance of the transgenic mouse does not meet a standard. In some embodiments, the dosing schedule of the compound is adjusted if the physical appearance of the transgenic mouse does not meet a standard. In other embodiments, the dosing amount and the schedule of the compound are adjusted if the physical appearance of the transgenic mouse does not meet a standard.

Further provided herein are methods for optimizing dosing amounts and/or schedules of a treatment compound in a transgenic mouse expressing human CRBN, comprising:
 (a) administering the compound to the transgenic mouse;
 (b) measuring a biological parameter of the transgenic mouse; and
 (c) adjusting the dosing amounts and/or schedule of the compound if the biological parameter of the transgenic mouse expressing CRBN does or does not meet a standard.

In certain embodiments of the various methods provided herein, the two or more of the steps are performed sequentially. In other embodiments of the methods provided herein, two or more of steps are performed in parallel (e.g., at the same time).

In certain embodiments, the dosing amount of the compound is adjusted if the biological parameter of the transgenic mouse meets a standard. In some embodiments, the dosing schedule of the compound is adjusted if the biological parameter of the transgenic mouse meets a standard. In other embodiments, the dosing amount and the schedule of the compound are adjusted if the biological parameter of the transgenic mouse meets a standard. In certain embodiments, the dosing amount of the compound is adjusted if the biological parameter of the transgenic mouse does not meet a standard. In some embodiments, the dosing schedule of the compound is adjusted if the biological parameter of the transgenic mouse does not meet a standard. In other embodiments, the dosing amount and the schedule of the compound are adjusted if the biological parameter of the transgenic mouse does not meet a standard.

Non-limiting examples of a biological parameter of the transgenic mouse include metabolic parameters, neurologic parameters, cognitive parameters, behavioral parameters, gene and protein expression/modification, epigenetic parameters, tumor growth, immunological parameters, histological parameters, blood parameters, and tissue parameters.

5.4.4 Methods for Evaluating Effects of a Compound or a Combination of Compounds In another aspect, provided herein is a method for evaluating the effect of a compound in a transgenic mouse expressing human CRBN or a fragment thereof, comprising:
 (a) administering the compound to the transgenic mouse;
 (b) obtaining a sample from the transgenic mouse;
 (c) measuring the level of a biomarker in the sample; and
 (d) comparing the level of the biomarker with a base level of the biomarker;
 wherein the biomarker is a CAP.

In yet another aspect, provided herein is a method for evaluating the effect of a combination of compounds in a transgenic mouse expressing human CRBN or a fragment thereof, comprising:
 (a) administering a first compound and a second compound to the transgenic mouse;
 (b) obtaining a sample from the transgenic mouse;
 (c) measuring the level of a biomarker in the sample; and
 (d) comparing the level of the biomarker with a base level of the biomarker;
 wherein the biomarker is a CAP.

In some embodiments, the method for evaluating the effect of a combination of compounds comprises administering a first compound, a second compound, and a third compound in the combination. In other embodiments, the method comprises administering more than three compounds in the combination. In certain embodiments, the compounds are administered concurrently. In other embodiments, the compounds are administered sequentially.

In certain embodiments, various transgenic mice used herein comprise a nucleic acid sequence encoding human CRBN. In certain embodiments, the nucleic acid sequence encoding the human CRBN is stably integrated into a mouse chromosome. In other embodiments, the nucleic acid sequence encodes a fragment of human CRBN. In certain embodiments, the nucleic acid sequence encoding the fragment of the human CRBN is stably integrated into a mouse chromosome. In one embodiment, the nucleic acid sequence encoding a full-length human CRBN protein comprises SEQ ID NO:5. In another embodiment, the nucleic acid sequence encoding a full-length human CRBN protein comprises SEQ ID NO:6. In one embodiment, the nucleic acid sequence encoding a fragment of human CRBN protein comprises SEQ ID NO:7. In another embodiment, the targeting construct encompassing the nucleic acid sequence encoding human CRBN or a fragment thereof comprises SEQ ID NO:8.

In some embodiments, the base level of the biomarker is an arbitrary level determined by scientists. In other embodiments, the base level of the biomarker is an empirical level based on prior measurement. In certain embodiments, the base level of the biomarker is an average or a mean level based on two or more prior measurements. In some embodiments, the base level of the biomarker is the level of the biomarker in a sample from a mouse that does not carry a human CRBN transgene. In other embodiments, the base level of the biomarker is the level of the biomarker in a sample from a mouse that expresses a human CRBN transgene. In yet other embodiments, the base level of the biomarker is the level of the biomarker in a sample from a transgenic mouse expressing human CRBN that has not been treated by any compounds. In still other embodiments, the base level of the biomarker is the level of the biomarker in a sample from a transgenic mouse expressing human CRBN that has been treated by one or more compounds.

In certain embodiments, the base level of the biomarker is the level of the biomarker when no compound is administered to the transgenic mouse. In some embodiments, the base level of the biomarker is the level of the biomarker when only one compound is administered to the transgenic mouse. In certain embodiments, the only one compound is the first compound. In other embodiments, the only one compound is the second compound. In yet other embodiments, the only one compound is the third compound. In still other embodiments, the only one compound is a control compound. In some embodiments, the base level of the biomarker is the level of the biomarker when a reference combination of two compounds is administered to the transgenic mouse. In certain embodiments, the reference combination comprises the first compound and another compound. In other embodiments, the reference combination comprises the second compound and another compound. In yet other embodiments, the reference combination comprises the third compound and another compound. In still other embodiments, the reference combination comprises the first compound and the second compound. In certain embodiments, the reference combination comprises two or more other compounds (i.e., not the first compound or the second compound).

In certain embodiments, the effect of a compound (or a combination of compounds) is the effect on antigen-specific T-cell killing.

In some embodiments, the compounds in the combination are administered either concurrently or sequentially. In certain embodiments, the compounds are administered concurrently. In other embodiments, the compounds are administered sequentially. In yet another embodiment of the methods, the compounds are administered in a particular order. In still another embodiment, the compounds are administered in a different order. In a specific embodiment, the compounds are administered in an order that is reverse to the particular order.

In some embodiments, a treatment compound comprises a compound provided in Section 5.4.2.

In any one of the methods for evaluating the effect of a combination of compounds, the compounds can be chosen from the same or different type of molecules (e.g., small molecule chemicals, or biologics, such as proteins, peptides, nucleic acids, or oligonucleotides). In some embodiments, the compounds are chosen from the same type of molecules. In other embodiments, the compounds are chosen from different type of molecules. In certain embodiments, the compounds can be chosen from immunomodulatory compounds, antibodies, PRR agonists, molecular mimics, inhibitors of enzymes, inhibitors of protein degradation apparatuses, and any type of anti-cancer drugs. In some embodiments, the compounds can be chosen from any two types of immunomodulatory compounds, antibodies, PRR agonists, molecular mimics, inhibitors of enzymes, inhibitors of protein degradation apparatuses, and any type of anti-cancer drugs. In other embodiments, the compounds can be chosen from any three types of immunomodulatory compounds, antibodies, PRR agonists, molecular mimics, inhibitors of enzymes, inhibitors of protein degradation apparatuses, and any type of anti-cancer drugs. In yet other embodiments, the compounds can be chosen from any four types of immunomodulatory compounds, antibodies, PRR agonists, molecular mimics, inhibitors of enzymes, inhibitors of protein degradation apparatuses, and any type of anti-cancer drugs. In yet other embodiments, the compounds can be chosen from any five types of immunomodulatory compounds, antibodies, PRR agonists, molecular mimics, inhibitors of enzymes, inhibitors of protein degradation apparatuses, and any type of anti-cancer drugs. In yet other embodiments, the compounds can be chosen from any six types of immunomodulatory compounds, antibodies, PRR agonists, molecular mimics, inhibitors of enzymes, inhibitors of protein degradation apparatuses, and any type of anti-cancer drugs. In yet other embodiments, the compounds can be chosen from all seven types of immunomodulatory compounds, antibodies, PRR agonists, molecular mimics, inhibitors of enzymes, inhibitors of protein degradation apparatuses, and any type of anti-cancer drugs.

In certain embodiments, the compound used is a CMC, which directly or indirectly modulating the CRBN E3 ubiquitin ligase. In some embodiments, the CMC can bind directly to CRBN. In other embodiments, the CMC can induce conformational change in the CRBN protein. In yet other embodiments, the CMC can bind directly to CRBN and induce conformational change in the CRBN protein. In still other embodiments, the CMC can bind directly to other subunits in the CRBN E3 ubiquitin ligase complex.

In some embodiments, the compound used is an immunomodulatory compound (e.g., thalidomide, lenalidomide, or pomalidomide). In one embodiment, the compound provided herein is thalidomide. In another embodiment, the compound provided herein is lenalidomide. In yet another embodiment, the compound provided herein is pomalidomide.

In other embodiments, the compound used is a compound selected from the group consisting of 3-(5-amino-2-methyl-4-oxo-4H-quinazolin-3-yl)-piperidine-2,6-dione ("Compound A"), which has the following structure:

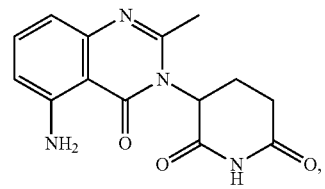 [SMILES: Cc1nc2cccc(N)c2c(=O)n1C1CCC(=O)NC1=O]

3-(4-((4-(morpholinomethyl)benzyl)oxy)-1-oxoisoindolin-2-yl)piperidine-2,6-dione ("Compound B"), which has the following structure:

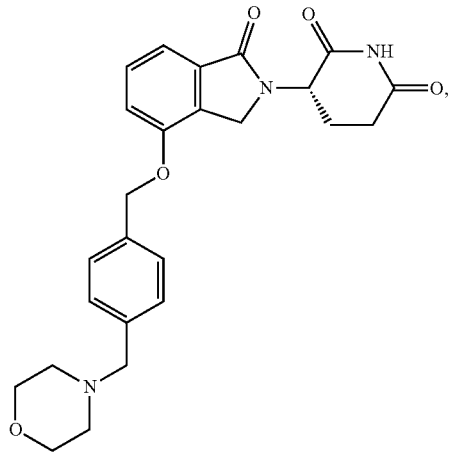 [SMILES: O=C1CC[C@H](N2Cc3c(OCc4ccc(CN5CCOCC5)cc4)cccc3C2=O)C(=O)N1]

1-(3-chloro-4-methylphenyl)-3-((2-(2,6-dioxopiperidin-3-yl)-1-oxoisoindolin-5-yl)methyl)urea ("Compound C"), which has the following structure:

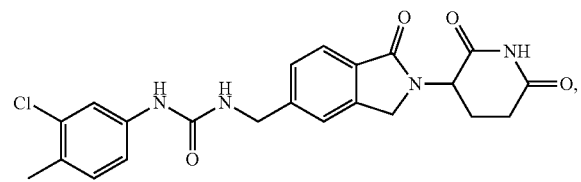 [SMILES: Cc1ccc(NC(=O)NCc2ccc3c(c2)CN(C2CCC(=O)NC2=O)C3=O)cc1Cl]

2-(4-chlorophenyl)-N-((2-(2,6-dioxopiperidin-3-yl)-1-oxoisoindolin-5-yl)methyl)-2,2-difluoroacetamide ("Compound D"), which has the following structure:

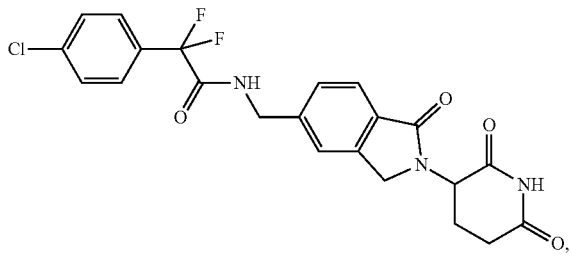

and
2-(4-flurophenyl)-N-((2-(2,6-dioxopiperidin-3-yl)-1-oxoisoindolin-5-yl)methyl)-2,2-difluoroacetamide ("Compound E"), which has the following structure:

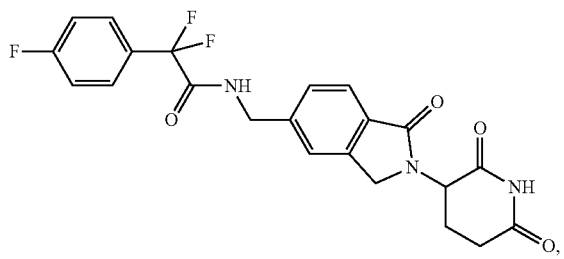 [SMILES: O=C1CCC(N2Cc3cc(CNC(=O)C(F)(F)c4ccc(F)cc4)ccc3C2=O)C(=O)N1]

or a pharmaceutically acceptable salt, solvate, stereoisomer, isotopologue, prodrug, hydrate, co-crystal, clathrate, or a polymorph thereof.

In one embodiment, the compound used is Compound A or a stereoisomer or a mixture of stereoisomers, tautomer, pharmaceutically acceptable salt, solvate, isotopologue, prodrug, hydrate, co-crystal, clathrate, or a polymorph thereof. In another embodiment, the compound used is Compound B, or a stereoisomer or a mixture of stereoisomers, tautomer, pharmaceutically acceptable salt, solvate, isotopologue, prodrug, hydrate, co-crystal, clathrate, or a polymorph thereof. In yet another embodiment, the compound used is Compound C, or a stereoisomer or a mixture of stereoisomers, tautomer, pharmaceutically acceptable salt, solvate, isotopologue, prodrug, hydrate, co-crystal, clathrate, or a polymorph thereof. In still another embodiment, the compound used is Compound D, or a stereoisomer or a mixture of stereoisomers, tautomer, pharmaceutically acceptable salt, solvate, isotopologue, prodrug, hydrate, co-crystal, clathrate, or a polymorph thereof. In again another embodiment, the compound used is Compound E, or a stereoisomer or a mixture of stereoisomers, tautomer, pharmaceutically acceptable salt, solvate, isotopologue, prodrug, hydrate, co-crystal, clathrate, or a polymorph thereof.

In certain embodiments of the methods for evaluating the effect of a combination of compounds, the combination of compounds comprises two compounds. In some embodiments, the combination of compounds comprises three compounds. In other embodiments, the combination of compounds comprises four compounds. In yet other embodiments, the combination of compounds comprises five compounds. In still other embodiments, the combination of compounds comprises six or more compounds.

In one embodiment, one of the compounds in the combination is dexamethasone. In another embodiment, one of the compounds in the combination is a CMC. In yet another embodiment, one of the compounds in the combination is an immunomodulatory compound. In still another embodiment, one of the compounds in the combination is an immunomodulatory compound selected from the group consisting of thalidomide, lenalidomide, and pomalidomide. In one embodiment, one of the compounds in the combination is thalidomide. In another embodiment, one of the compounds in the combination is lenalidomide. In yet another embodiment, one of the compounds in the combination is pomalidomide. In one embodiment, one of the compounds in the combination is a compound with anti-B-cell malignancy activity. In another embodiment, one of the compounds in the combination is a compound with anti-multiple myeloma activity.

In certain embodiments, one of the compounds in the combination is selected from the group consisting of ixazomib, carfilzomib, elotuzumab, daratumumab, azacytidine, ACY-241, cyclophosphamide, durvalumab, abraxane, and nivolumab. In one embodiment, one of the compounds in the combination is ixazomib. In another embodiment, one of the compounds in the combination is carfilzomib. In yet another embodiment, one of the compounds in the combination is elotuzumab. In still another embodiment, one of the compounds in the combination is daratumumab. In one embodiment, one of the compounds in the combination is azacytidine. In another embodiment, one of the compounds in the combination is ACY-241. In yet another embodiment, one of the compounds in the combination is cyclophosphamide. In still another embodiment, one of the compounds in the combination is durvalumab. In one embodiment, one of the compounds in the combination is abraxane. In another embodiment, one of the compounds in the combination is nivolumab.

In certain embodiments, the combination of compounds includes a CMC and dexamethasone. In some embodiments, the combination of compounds includes an immunomodulatory compound and dexamethasone. In other embodiments, the combination of compounds includes an immunomodulatory compound selected from the group consisting of thalidomide, lenalidomide, and pomalidomide, and dexamethasone. In yet other embodiments, the combination of compounds includes a compound with anti-B-cell malignancy activity and dexamethasone. In still other embodiments, the combination of compounds includes a compound with anti-multiple myeloma activity and dexamethasone. In one embodiment, the combination of compounds includes thalidomide and dexamethasone. In another embodiment, the combination of compounds includes lenalidomide and dexamethasone. In yet another embodiment, the combination of compounds includes pomalidomide and dexamethasone.

In certain embodiments, the combination of compounds includes a CMC, dexamethasone, and a compound selected from the group consisting of ixazomib, carfilzomib, elotuzumab, daratumumab, azacytidine, ACY-241, cyclophosphamide, durvalumab, abraxane, and nivolumab. In some embodiments, the combination of compounds includes an immunomodulatory compound, dexamethasone, and a compound selected from the group consisting of ixazomib, carfilzomib, elotuzumab, daratumumab, azacytidine, ACY-241, cyclophosphamide, durvalumab, abraxane, and nivolumab. In other embodiments, the combination of compounds includes dexamethasone, an immunomodulatory compound selected from the group consisting of thalidomide, lenalidomide, and pomalidomide, and a compound selected from the group consisting of ixazomib, carfilzomib, elotuzumab, daratumumab, azacytidine, ACY-241, cyclophosphamide, durvalumab, abraxane, and nivolumab. In yet other embodiments, the combination of compounds includes a compound with anti-B-cell malignancy activity, dexamethasone, and a compound selected from the group consisting of ixazomib, carfilzomib, elotuzumab, daratumumab, azacytidine, ACY-241, cyclophosphamide, durvalumab, abraxane, and nivolumab. In still other embodiments, the combination of compounds includes a compound with anti-multiple myeloma activity, dexamethasone, and a compound selected from the group consisting of ixazomib, carfilzomib, elotuzumab, daratumumab, azacytidine, ACY-241, cyclophosphamide, durvalumab, abraxane, and nivolumab. In one embodiment, the combination of compounds includes thalidomide, dexamethasone, and a compound selected from the group consisting of ixazomib, carfilzomib, elotuzumab, daratumumab, azacytidine, ACY-241, cyclophosphamide, durvalumab, abraxane, and nivolumab. In another embodiment, the combination of compounds includes lenalidomide, dexamethasone, and a compound selected from the group consisting of ixazomib, carfilzomib, elotuzumab, daratumumab, azacytidine, ACY-241, cyclophosphamide, durvalumab, abraxane, and nivolumab. In yet another embodiment, the combination of compounds includes pomalidomide, dexamethasone, and a compound selected from the group consisting of ixazomib, carfilzomib, elotuzumab, daratumumab, azacytidine, ACY-241, cyclophosphamide, durvalumab, abraxane, and nivolumab.

In one embodiment, the combination of compounds comprises dexamethasone, a CMC, and ixazomib. In another embodiment, the combination of compounds comprises dexamethasone, a CMC, and carfilzomib. In yet another embodiment, the combination of compounds comprises dexamethasone, a CMC, and elotuzumab. In still another embodiment, the combination of compounds comprises dexamethasone, a CMC, and daratumumab. In one embodiment, the combination of compounds comprises dexamethasone, a CMC, and azacytidine. In another embodiment, the combination of compounds comprises dexamethasone, a CMC, and ACY-241. In yet another embodiment, the combination of compounds comprises dexamethasone, a CMC, and a cyclophosphamide. In still another embodiment, the combination of compounds comprises dexamethasone, a CMC, and durvalumab. In one embodiment, the combination of compounds comprises dexamethasone, a CMC, and abraxane. In another embodiment, the combination of compounds comprises dexamethasone, a CMC, and nivolumab.

In one embodiment, the combination of compounds comprises dexamethasone, an immunomodulatory compound, and ixazomib. In another embodiment, the combination of compounds comprises dexamethasone, an immunomodulatory compound, and carfilzomib. In yet another embodiment, the combination of compounds comprises dexamethasone, an immunomodulatory compound, and elotuzumab. In still another embodiment, the combination of compounds comprises dexamethasone, an immunomodulatory compound, and daratumumab. In one embodiment, the combination of compounds comprises dexamethasone, an immunomodulatory compound, and azacytidine. In another embodiment, the combination of compounds comprises dexamethasone, an immunomodulatory compound, and ACY-241. In yet another embodiment, the combination of compounds comprises dexamethasone, an immunomodulatory compound, and a cyclophosphamide. In still another embodiment, the combination of compounds comprises dexamethasone, an immunomodulatory compound, and durvalumab. In one embodiment, the combination of compounds comprises dexamethasone, an immunomodulatory compound, and abraxane. In another embodiment, the combination of compounds comprises dexamethasone, an immunomodulatory compound, and nivolumab.

In one embodiment, the combination of compounds comprises dexamethasone, lenalidomide, and ixazomib. In another embodiment, the combination of compounds comprises dexamethasone, lenalidomide, and carfilzomib. In yet another embodiment, the combination of compounds comprises dexamethasone, lenalidomide, and elotuzumab. In still another embodiment, the combination of compounds comprises dexamethasone, lenalidomide, and daratumumab. In one embodiment, the combination of compounds comprises dexamethasone, lenalidomide, and azacytidine. In another embodiment, the combination of compounds comprises dexamethasone, lenalidomide, and ACY-241. In yet another embodiment, the combination of compounds comprises dexamethasone, lenalidomide, and a cyclophosphamide. In still another embodiment, the combination of compounds comprises dexamethasone, lenalidomide, and durvalumab. In one embodiment, the combination of compounds comprises dexamethasone, lenalidomide, and abraxane. In another embodiment, the combination of compounds comprises dexamethasone, lenalidomide, and nivolumab.

In one embodiment, the combination of compounds comprises dexamethasone, thalidomide, and ixazomib. In another embodiment, the combination of compounds comprises dexamethasone, thalidomide, and carfilzomib. In yet another embodiment, the combination of compounds comprises dexamethasone, thalidomide, and elotuzumab. In still another embodiment, the combination of compounds comprises dexamethasone, thalidomide, and daratumumab. In one embodiment, the combination of compounds comprises dexamethasone, thalidomide, and azacytidine. In another embodiment, the combination of compounds comprises dexamethasone, thalidomide, and ACY-241. In yet another embodiment, the combination of compounds comprises dexamethasone, thalidomide, and a cyclophosphamide. In still another embodiment, the combination of compounds comprises dexamethasone, thalidomide, and durvalumab. In one embodiment, the combination of compounds comprises dexamethasone, thalidomide, and abraxane. In another embodiment, the combination of compounds comprises dexamethasone, thalidomide, and nivolumab.

In one embodiment, the combination of compounds comprises dexamethasone, pomalidomide, and ixazomib. In another embodiment, the combination of compounds comprises dexamethasone, pomalidomide, and carfilzomib. In yet another embodiment, the combination of compounds comprises dexamethasone, pomalidomide, and elotuzumab. In still another embodiment, the combination of compounds comprises dexamethasone, pomalidomide, and daratumumab. In one embodiment, the combination of compounds comprises dexamethasone, pomalidomide, and azacytidine. In another embodiment, the combination of compounds comprises dexamethasone, pomalidomide, and ACY-241. In yet another embodiment, the combination of compounds comprises dexamethasone, pomalidomide, and a cyclophosphamide. In still another embodiment, the combination of compounds comprises dexamethasone, pomalidomide, and durvalumab. In one embodiment, the combination of compounds comprises dexamethasone, pomalidomide, and abraxane. In another embodiment, the combination of compounds comprises dexamethasone, pomalidomide, and nivolumab.

In one embodiment, the combination of compounds comprises dexamethasone, a compound with anti-B-cell malignancy activity, and ixazomib. In another embodiment, the combination of compounds comprises dexamethasone, a compound with anti-B-cell malignancy activity, and carfilzomib. In yet another embodiment, the combination of compounds comprises dexamethasone, a compound with anti-B-cell malignancy activity, and elotuzumab. In still another embodiment, the combination of compounds comprises dexamethasone, a compound with anti-B-cell malignancy activity, and daratumumab. In one embodiment, the combination of compounds comprises dexamethasone, a compound with anti-B-cell malignancy activity, and azacytidine. In another embodiment, the combination of compounds comprises dexamethasone, a compound with anti-B-cell malignancy activity, and ACY-241. In yet another embodiment, the combination of compounds comprises dexamethasone, a compound with anti-B-cell malignancy activity, and a cyclophosphamide. In still another embodiment, the combination of compounds comprises dexamethasone, a compound with anti-B-cell malignancy activity, and durvalumab. In one embodiment, the combination of compounds comprises dexamethasone, a compound with anti-B-cell malignancy activity, and abraxane. In another embodiment, the combination of compounds comprises dexamethasone, a compound with anti-B-cell malignancy activity, and nivolumab.

In one embodiment, the combination of compounds comprises dexamethasone, a compound with anti-multiple myeloma activity, and ixazomib. In another embodiment, the combination of compounds comprises dexamethasone, a compound with anti-multiple myeloma activity, and carfilzomib. In yet another embodiment, the combination of compounds comprises dexamethasone, a compound with anti-multiple myeloma activity, and elotuzumab. In still another embodiment, the combination of compounds comprises dexamethasone, a compound with anti-multiple myeloma activity, and daratumumab. In one embodiment, the combination of compounds comprises dexamethasone, a compound with anti-multiple myeloma activity, and azacytidine. In another embodiment, the combination of compounds comprises dexamethasone, a compound with anti-multiple myeloma activity, and ACY-241. In yet another embodiment, the combination of compounds comprises dexamethasone, a compound with anti-multiple myeloma activity, and a cyclophosphamide. In still another embodiment, the combination of compounds comprises dexamethasone, a compound with anti-multiple myeloma activity, and durvalumab. In one embodiment, the combination of compounds comprises dexamethasone, a compound with anti-multiple myeloma activity, and abraxane. In another embodiment, the combination of compounds comprises dexamethasone, a compound with anti-multiple myeloma activity, and nivolumab.

In some embodiments, the biomarker measured comprises a biomarker provided in Section 5.4.1.

In certain embodiments of the various methods provided herein, the biomarker is a protein that is directly or indirectly affected by CRBN, for example through protein-protein interactions (e.g., certain CRBN substrates or downstream effectors thereof), or through various cellular pathways (e.g., signal transduction pathways). In specific embodiments, the biomarker is a CAP. In some embodiments, the biomarker is mRNA of a protein that is directly or indirectly affected by CRBN. In other embodiments, the biomarker is cDNA of a protein that is directly or indirectly affected by CRBN. In certain embodiments, the biomarker is directly or indirectly affected by one or more isoforms of CRBN. In some embodiments, the biomarker is directly or indirectly affected by one but not other isoforms of CRBN.

In some embodiments, the biomarker measured comprises one biomarker. In certain embodiments, the biomarkers measured comprise two or more biomarkers. In some embodiments, the levels of the biomarkers are measured by detecting and quantifying the protein levels of the biomarkers. In other embodiments, the levels of the biomarkers are measured by detecting and quantifying the nucleic acid levels of the biomarkers. In one embodiment, the levels of the biomarkers are measured by detecting and quantifying the cDNA levels of the biomarkers. In another embodiment, the levels of the biomarkers are measured by detecting and quantifying the mRNA levels of the biomarkers. Any suitable methods of measuring biomarkers provided herein or well know in the art can be used to detect and quantify the levels of the biomarkers.

In one embodiment, the treatment compound is Compound A or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1. In another embodiment, the treatment compound is Compound B or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1. In still another embodiment, the treatment compound is Compound C or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1. In yet another embodiment, the treatment compound is Compound D or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1. In one embodiment, the treatment compound is Compound E or a stereoisomer or a mixture of stereoisomers, tautomer, pharmaceutically acceptable salt, solvate, isotopologue, prodrug, hydrate, co-crystal, clathrate, or a polymorph thereof, and the biomarker is one or more biomarkers selected from the group consisting of Aiolos, Ikaros, and GSPT1.

5.4.5 Methods for Evaluating Effects of Compounds on Antigen Specific T-Cell Killing In certain embodiments of various methods provided herein, the effect of a compound or a combination of compounds is the effect on antigen specific T-cell killing. T-cell mediated cytotoxicity can be induced by antigen-presenting cells (APCs) that bring a variety of specific antigens to naive T-cells. Non-limiting examples of APCs include dendritic cells (DCs), macrophages, certain B-cells, and certain activated epithelial cells. Activated cytotoxic T-cells then kill the target cells (e.g., tumor cells) that have specific antigens (e.g., tumor antigens) on their surface. Various methods for evaluating antigen specific T-cell killing in vivo or in vitro are disclosed in scientific literature, for example, in vitro analysis of T-cell responses induced by breast tumor cell lysate pulsed with autologous dendritic cells. See Delirezh et al., *Advances in Biosci. Biotechnol.* 2012, 3:126-136.

In certain embodiments of the methods, the APC is DCs. In some embodiments, the APC is macrophages. In certain embodiments, the APC is isolated from an animal. In other embodiments, the APC is derived in vitro from isolated peripheral blood mononuclear cells (PBMC) from an animal. In yet other embodiments, the APC is derived in vitro from isolated programmable cell of monocyte origin (PCMO) from an animal.

The maturation of APC (e.g., DCs) can be induced by a variety of factors (e.g., TNF-α) and/or conditioned media (e.g., monocyte conditioned medium (MCM), fibroblast conditioned medium (FCM), PHA-activated T-cell conditioned medium (TCM), or fibroblast and T-cell conditioned medium (FCM-TCM)). Unfractionated tumor derived antigens, such as tumor cell lysate, peptides eluted from tumor cell membrane, apoptotic tumor cell, tumor peptide pulsed DC derived exosomes, fusion of tumor and DCs, and tumor cell RNA, can be used in pulsing DCs. In various embodiments, the tumor cell can be any kind of tumor cells, such as solid tumor cells or blood cancer cells. In some embodiments, the tumor cell is multiple myeloma cell. In other embodiments, the tumor cell is B-cell malignancy cell.

Pulsed DCs then are able to elicit T-cell responses in proliferation, cytotoxicity, an cytokine release against autologous tumor cells. Thus, T-cell proliferation, T-cell cytotoxicity, and cytokine release can be measured using well-known assays disclosed in literature. See Delirezh et al., *Advances in Biosci, Biotechnol.* 2012, 3:126-136.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations, methods of producing a transgenic mouse, and/or methods of use provided herein, may be made without departing from the spirit and scope thereof. U.S. patents and publications referenced herein are incorporated by reference.

It is noted that any combination of the above-listed embodiments, for example, with respect to one or more reagents (e.g., TALENs, CRISPR/Cas9, ZFNs, nucleic acid primers, etc.), one or more procedures (e.g., transfection, electroporation, etc.), or one or more steps (e.g., step (a), step (b), step (c), step (d) in various methods provided herein) are also contemplated in relation to any of the various methods provided herein.

Certain embodiments of the invention are illustrated by the following non-limiting examples.

6. EXAMPLES

The examples below are carried out using standard techniques, which are well known and routine to those of skill in the art, except where otherwise described in detail. The examples are intended to be merely illustrative.

6.1 Generation of Targeting Construct for Producing Human CRBN Transgenic Mouse

The first 23 amino acids of the human CRBN isoform 1 and the mouse CRBN isoform 2 (corresponding to the human CRBN isoform 1) are identical. These 23 amino acids are encoded by exon 1 of the human or the mouse CRBN gene. Alternative splicing mechanism removes the 23rd amino acid to generate the human CRBN isoform 2 or the mouse CRBN isoform 1, which are one amino acid shorter than the human CRBN isoform 1 or the mouse CRBN isoform 2, respectively. Thus, the mouse exon 1/intron 1/exon 2 splicing can be maintained. The knock-in strategy is to insert the human cDNA that encodes CRBN beginning at exon 2. This should help ensure sufficient expression of the human cDNA from the endogenous mouse promoter by including an intron, which is important for in vivo expression of the cDNA. A poly(A) sequence after the human CRBN cDNA coding sequence will terminate the transcript and disrupt any further splicing or expression of the mouse gene. The alternative splicing mechanism in the host mouse will be able to generate the human CRBN isoform 1 and the human CRBN isoform 2 in the transgenic mouse. Exon 3 is out of fame with exon 1, so aberrant splicing would not result in a functional CRBN protein.

Figure 1:
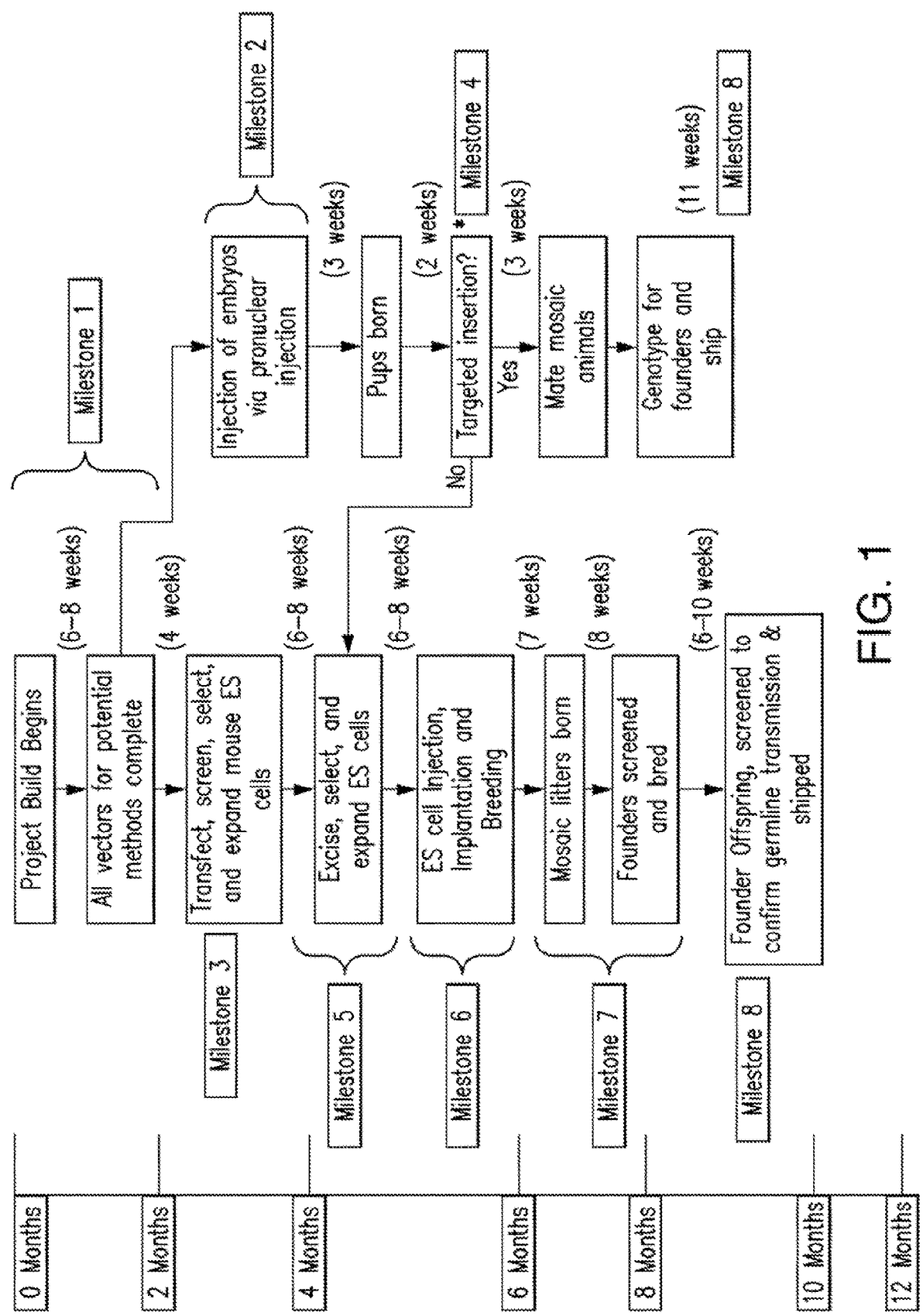

FIG. 1 shows the flow chart of producing a human CRBN knock-in transgenic mouse, which includes generation of targeting construct, introduction of targeting construct to ES cells or embryos, production of chimeras, and germline transmission.

FIG. 2 shows the design of knocking in human CRBN in a mouse genome. Part A of FIG. 2 illustrates part of the mouse CRBN gene (including exon 2 and exon 3) in a mouse genome. Part B of FIG. 2 illustrates a targeting construct containing a portion of the human CRBN isoform 1 cDNA (starting from codon 24, Glutamate, and ending at the stop codon), followed by a recombinant poly(A) sequence (e.g., bGH pA) and Neomycin selection cassette flanked by two loxP sites, and 5' homology arm and 3' homology arm. The dotted lines between Part A and Part B illustrate the replacement of a portion of the mouse genome (including exon 2 of the mouse CRBN gene) with the targeting construct containing the human CRBN cDNA, bGH pA, lox-flanked Neomycin selection cassette, and 5' homology arm and 3' homology arm. Part C illustrates the targeted genome after human CRBN knock-in, in which the targeting construct sequence is stably integrated into the mouse genome. Part D illustrates the targeted genome after Cre excision of the Neomycin selection cassette.

Figure 3A:
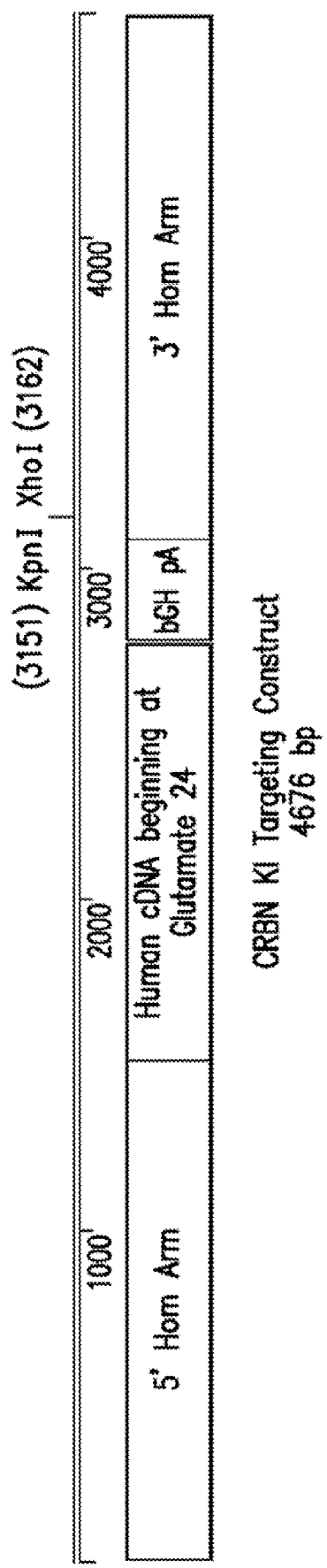
Figure 3B:
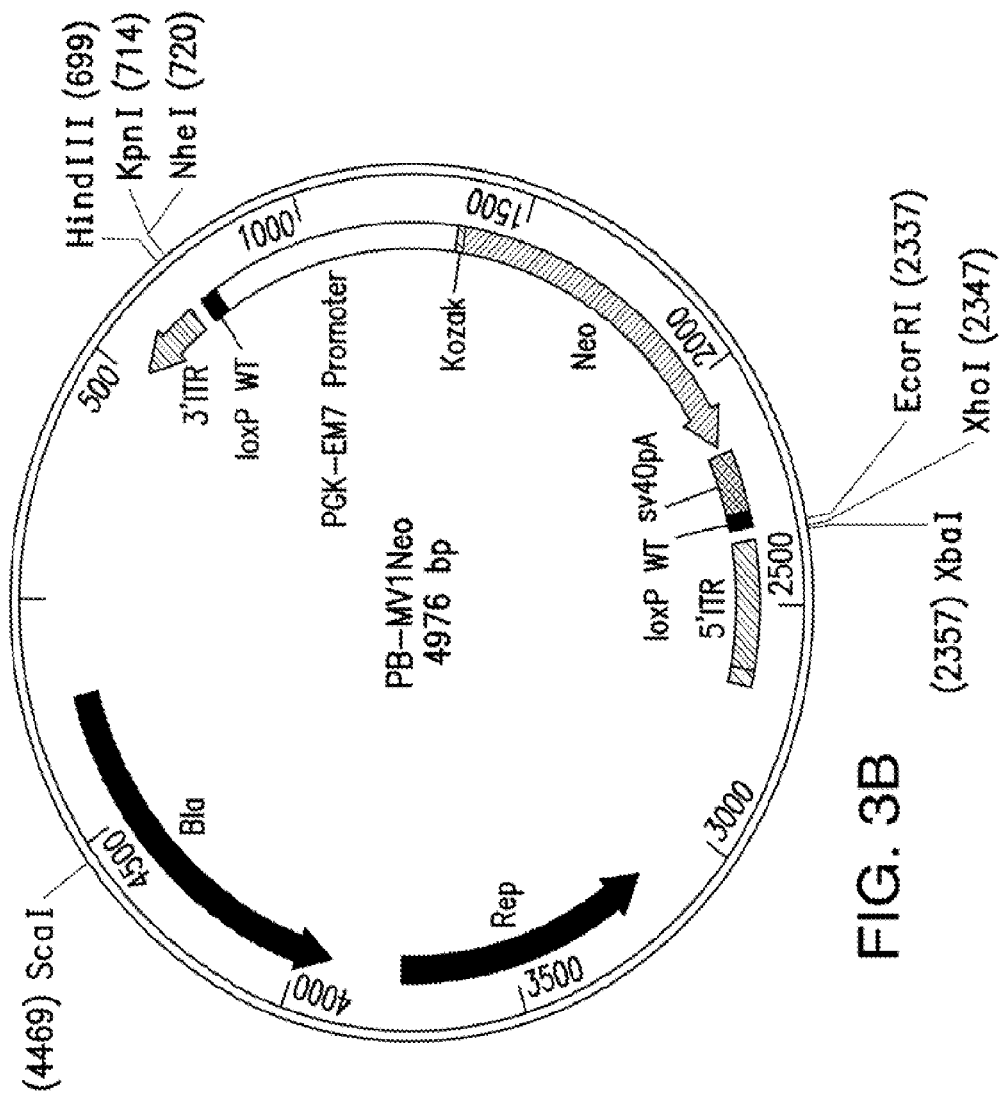
Figure 3C:
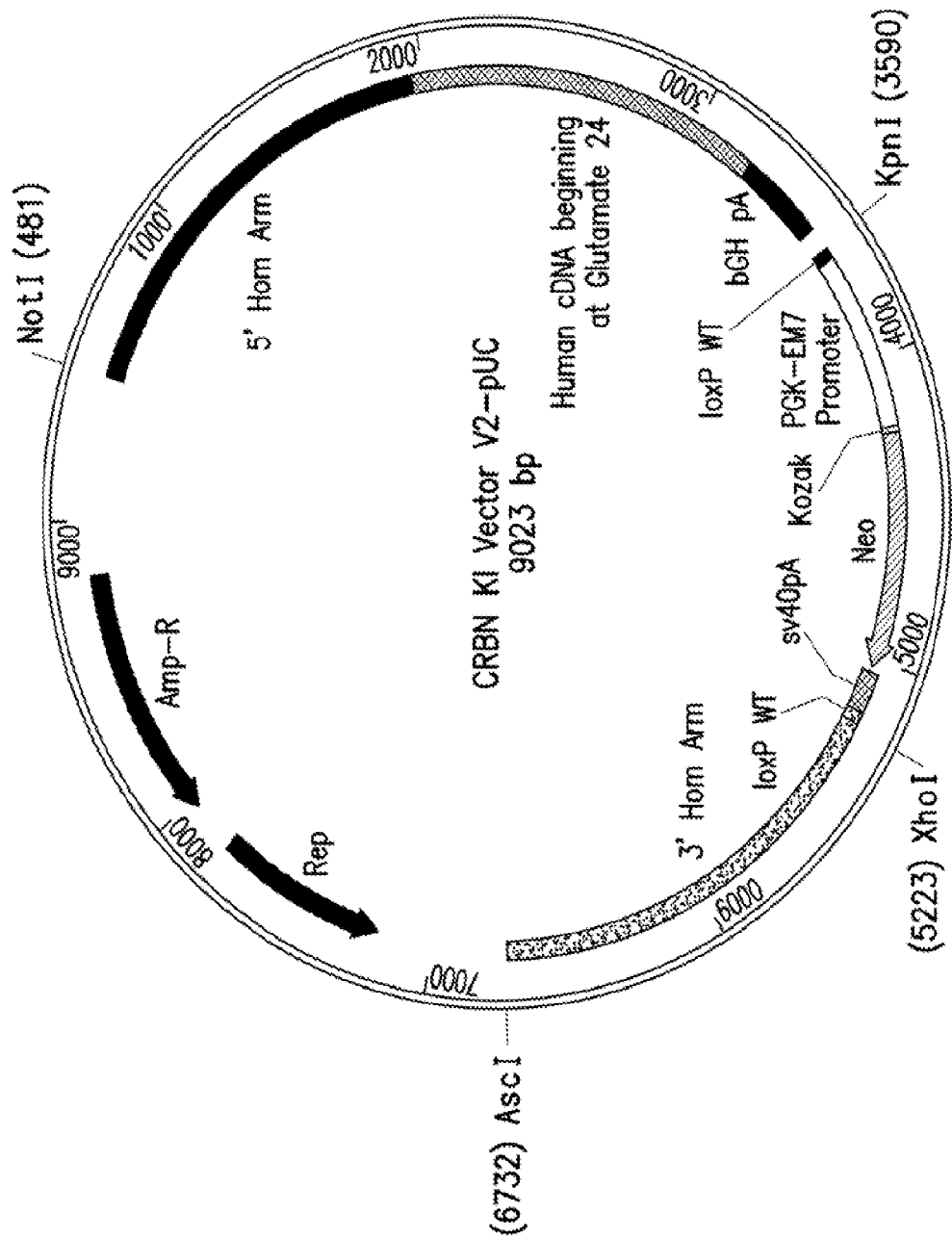

FIGS. 3A-3C illustrate the cloning strategy for one example of donor vectors, CRBN KI Vector V2-pUC. FIG. 3C shows that CRBN KI Vector V2-pUC comprises (1) the backbone of a pUC57-Simple cloning vector, (2) a human cDNA sequence encoding a fragment of CRBN (starting from codon 24, Glutamate, and ending at the stop codon) consisting of the nucleic acid sequence of SEQ ID NO: 7, followed by a recombinant poly(A) sequence (e.g., bGH pA) and a Neomycin selection cassette controlled by a PGK-EM7 promoter and flanked by two loxP sites, and (3) a 5' homology arm and a 3' homology arm at the 5'-end and the 3'-end of (2), respectively. The homology arms match the intron sequences flanking the exon 2 of the mouse CRBN gene and facilitate homologous recombination with the mouse genome. The 5' homology arm comprises nucleotides 1-1508 of SEQ ID NO: 8. The 3' homology arm comprises nucleotides 4782-6282 of SEQ ID NO: 8. The region of CRBN KI Vector V2-pUC that comprises components (2) and (3) corresponds to the targeting construct illustrated in FIG. 2B. The nucleic acid sequence of this targeting construct is set forth in SEQ ID NO: 8.

CRBN KI Vector V2-pUC was generated as follows: (1) a synthetic DNA encompassing 1.5 kb of the mouse CRBN intron 1 and the beginning of mouse CRBN exon 2, followed by the human CRBN isoform 1 cDNA beginning at the codon 24 glutamate through the stop codon, the bovine growth hormone poly(A) signal, and 1.5 kb of mouse CRBN intron 3 (FIG. 3A) was synthesized by Genscript, Inc. (Piscataway, NJ), Kpn I and Xho I restriction sites were included in the beginning of intron 3 to enable cloning of a neomycin selection cassette; (2) CRBN KI Targeting Construct was cloned into plasmid pUC57-Simple at EcoRV restriction site to generate plasmid CRBN-pUC (map not shown); (3) then a 1637 bp Kpn I/Xho I piece of PB-MV1Neo (FIG. 3B), which includes a PGK promoter, a neomycin selection cassette, and an SV40 poly(A), was cloned into CRBN-pUC at Kpn I and Xho I restriction sites to generate the donor vector CRBN KI Vector-V2-pUC (FIG. 3C). The donor vector CRBN KI Vector-V2-pUC was then electroporated into mouse ES cells.

6.2 Design of XTN™ TALENs and Testing of Their Activity

Three XTN™ TALENs were designed to target Neomycin cassette insertion site to enhance targeting. XTN™ TALEN 1 targets a nucleic acid sequence of TATGCGGACCTTTATCTAtggctggaatttcctaAGTGCAGG-GAGCCACA (SEQ ID NO:9). XTN™ TALEN 2 targets a nucleic acid sequence of TGCAGTATGCGGACCTTtatc-tatggctggaatTTCCTAAGTGCAGGGA (SEQ ID NO:10). XTN™ TALEN 3 targets a nucleic acid sequence of TCTGCCAACCTCACATacagtatgtggtttaGTCATT-GAGCAAATGCA (SEQ ID NO:11).

Figure 4:
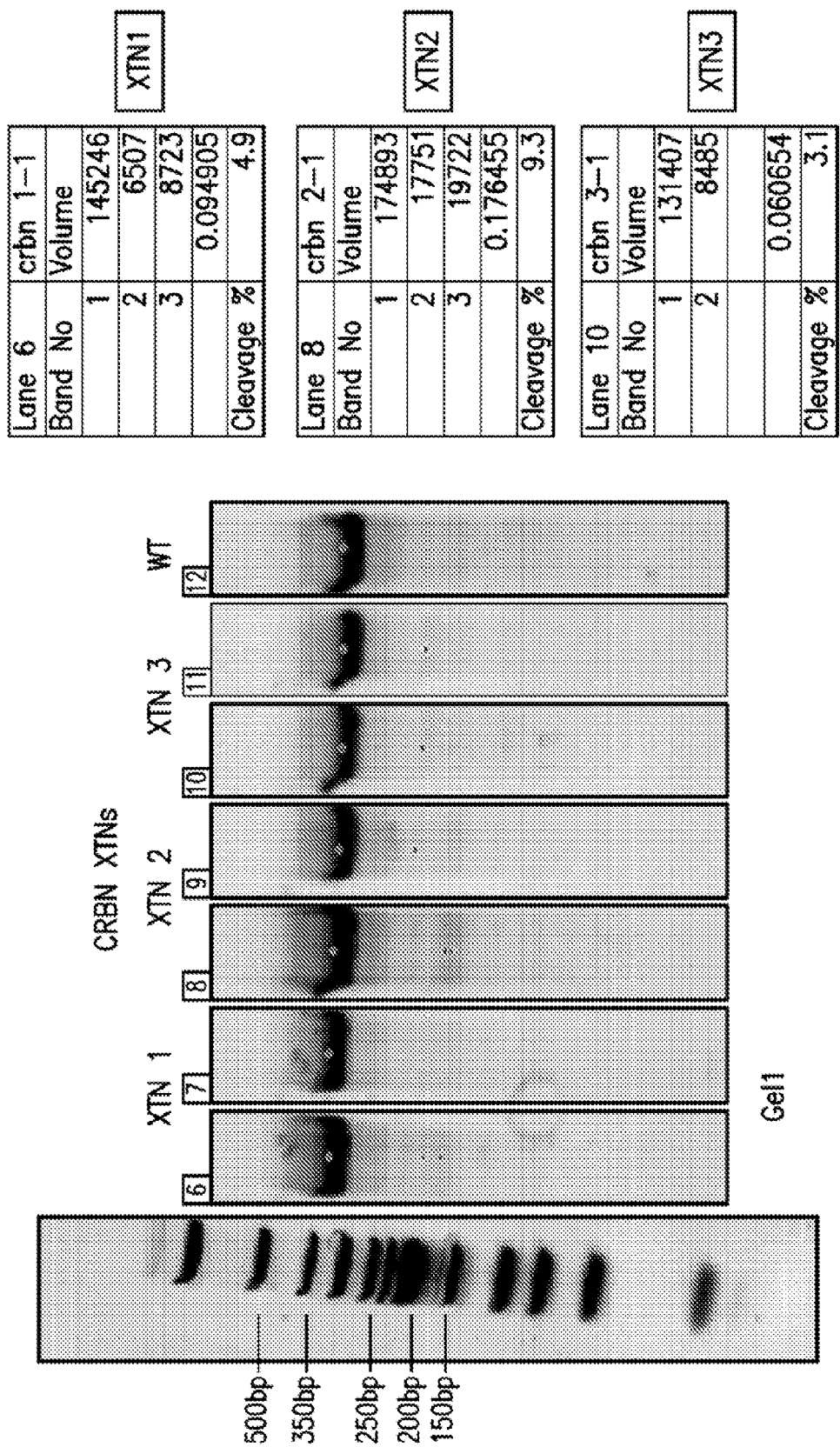
FIG. 4 shows reagent activity testing of three XTN™ TALENs. The Cel-1 assay indicates that XTN™ TALEN2 has the most activity.

FIG. 4 shows reagent activity testing of three XTN™ TALENs using the Cel-1 assay. Expected band sizes are 170 bp and 160 bp for XTN™ TALENs 1 and 2, and 200 bp and 130 bp for XTN™ TALEN 3. The results indicate that XTN™ TALEN 1 had 5% activity, XTN™ TALEN 2 had 9% activity, and XTN™ TALEN 3 had 3% activity. Thus, XTN™ TALEN 2 had the most activity and was electroporated into mouse ES cells together with the donor vector CRBN KI Vector-V2-pUC.

6.3 Electroporation of Mouse ES Cells and Identification of Clones Containing the Human CRBN Gene C57BL/6NTac JM8 ES cells were electroporated with the donor vector CRBN KI Vector-V2-pUC and XTN™ TALEN 2. Twenty-four ES clones were screened for targeting using primers to detect correct 5' and 3' targeting. The PCR primers for detecting the 5' and 3' targeting are listed in Table 1.

TABLE 1

PCR Primers for Detecting the 5' and 3' Targeting

| Primer | Sequence | Size of expected product |
|---|---|---|
| CRBN 5' targcheckF1 | ctgcattaccggggttttta (SEQ ID NO: 12) | 1968 bp |
| CRBN 5' targcheckR1 | GCTGTTGTTCCAAACTGTGC (SEQ ID NO: 13) | |
| CRBN 3' targcheckF1 | CGGACCGCTATCAGGACATA (SEQ ID NO: 14) | 1939 bp |
| CRBN 3' targcheckR1 | gccttccaattgctttcact (SEQ ID NO: 15) | |

Figure 5:
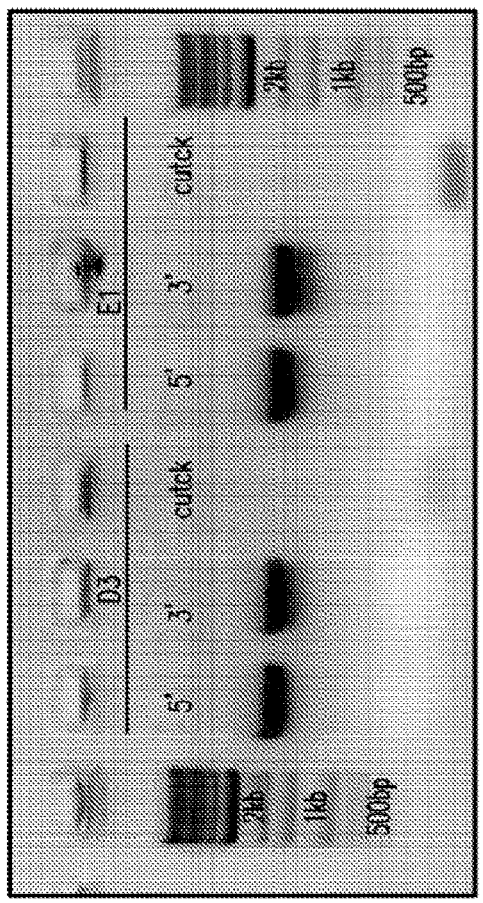
FIG. 5 shows two of three mouse ES clones, D3 and E1, that have correct 5' and 3' targeting, confirmed by PCR.

Three ES clones were identified with correct targeting on both 5' and 3' ends. Results for two clones (D3 and E1) are shown as in FIG. 5. The left half of the gel shows the PCR products of ES clone D3, and the right half of the gel shows the PCR products of ES clone E1. The 5' PCR product has an expected size of approximately 1968 bp, and the 3' PCR product has an expected size of approximately 1939 bp.

Sequence of the PCR products confirmed targeting on the 5' and 3' ends for clones E1, D2, and D3. For example, the PCR product of the 5' targeting showed the junction of the targeting arm and the genomic sequence at the 5' end and the human CRBN cDNA at the 3' end. These ES clones were karyotyped and expanded.

6.4 Implantation of ES Cells and Generation of Chimeras

Two ES clones (D2 and E1) were injected into C57BL/6NTac blasts. Mouse embryos (blastocysts) of 3.5 days old were used in the standard method of injection of ES cells from clones D2 and E1. Injected blastocytes then were implanted into pseudopregnant female mice. Chimeras were born and confirmed by either Nnt genotyping or coat color. Clone E1 yielded the highest level of chimerism. These chimeras were chosen to breed for germline transmission.

6.5 Germline Transmission of the Human CRBN Gene

Chimeras from clone E1 were bred to Cre recombinase deleter mice (Cre expressed from a ROSA26 locus) to achieve deletion of the Neomycin resistance cassette and to determine germline transmission. Offspring were evaluated using PCR primers that are specific to the human cDNA insert. Three pups (two female and one male) were identified by PCR and sequence verified to contain the human cDNA-bGH pA, one loxP site, and without Neomycin cassette.

Figure 6:
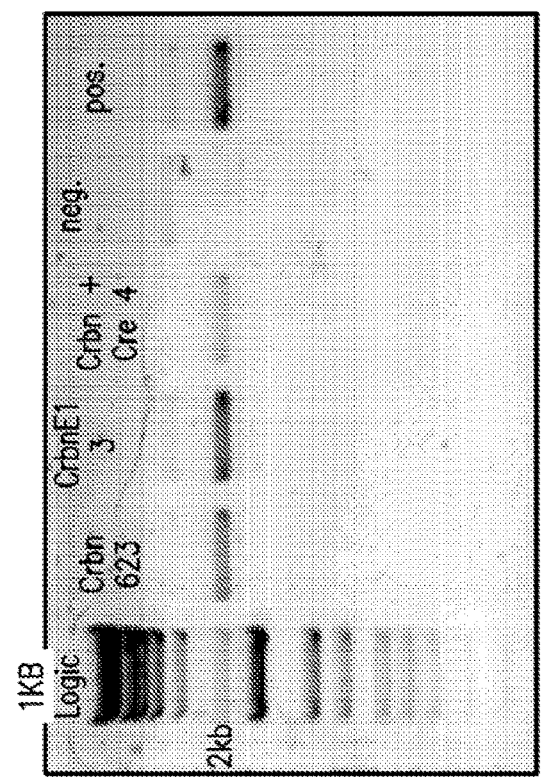
FIG. 6 shows three human CRBN transgenic mice with germline transmission, confirmed by 5' targeting PCR.

FIG. 6 shows 5' targeting PCR confirmation of three germline animals. Lane 1 is molecular weight marker. Lanes 2-4 are PCR product from three germline animals generated from clone E1 chimeras. Lane 2 is PCR product from CRBN623; Lane 3 is PCR product from 3; Lane 4 is PCR product from CRBN+Cre 4. Lanes 5 and 6 are negative and positive controls, respectively.

Figure 7:
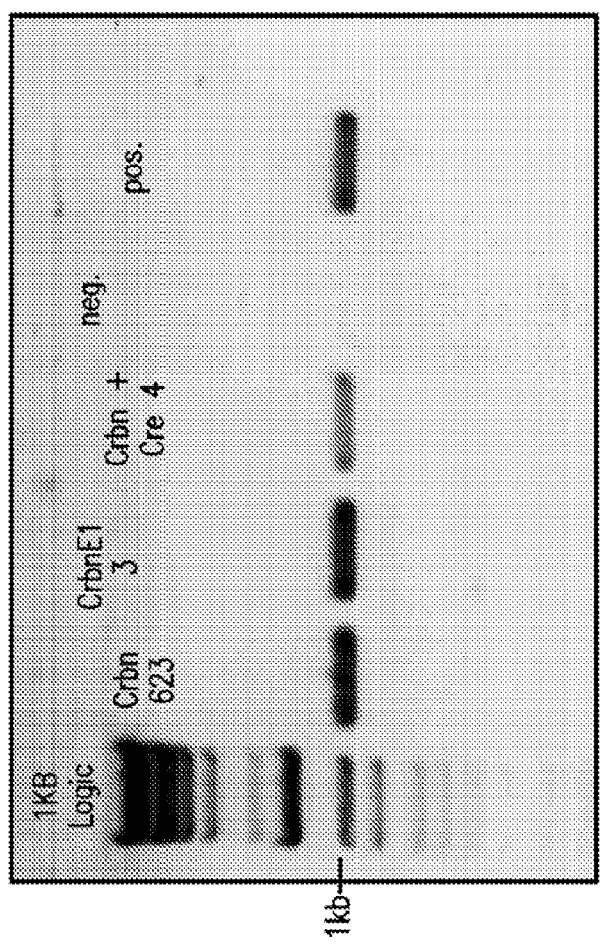
FIG. 7 shows three human CRBN transgenic mice with germline transmission, confirmed by human cDNA PCR.

FIG. 7 shows hu-cDNA-pA PCR confirmation of three germline animals using genotyping primers. Lane 1 is molecular weight marker. Lanes 2-4 are PCR product from three germline animals generated from clone E1 chimeras. Lane 2 is PCR product from CRBN623; Lane 3 is PCR product from 3; Lane 4 is PCR product from CRBN+Cre 4. Lanes 5 and 6 are negative and positive controls, respectively.

The genotyping primers used are as follows: The forwarding primer is CRBNhu-cDNA-F1, comprising a nucleic acid sequence of TGTGTTGCCTTCAACCATGT (SEQ ID NO:16). The reverse primer is bGHpA-R1, comprising a nucleic acid sequence of CAGCATGCCTGCTATTGTCT (SEQ ID NO:17).

6.6 Breeding and Identification of Mice Homozygous for the Human CRBN Gene

The above two heterozygous female mice with germline transmission of the human CRBN gene were used for expansion breeding. This was to secure and establish a stable line of mice expressing the human CRBN gene. The goal was to establish a cohort of homozygous mice with the human CRBN gene and to cross out the Cre recombinase allele. The female mice were bred with non-Cre C57BL/6NTac mice to remove Cre gene to generate heterozygous human CRBN knock-in mice. Matings between the heterozygous human CRBN knock-in mice produced homozygous human CRBN knock-in mice.

6.7 Breeding of Mice Homozygous for the Human CRBN Gene and Mice with Other Genetic Backgrounds Mice homozygous for the human CRBN gene can be bred with mice of other genetic backgrounds, e.g., NSG/NOG mice, Vk*myc multiple myeloid model, Eu-v-abl/Eu-c-Myc (virus inoculation+pristine) multiple myeloid model, Eu-c-Myc lymphoma model, human IKZF1/3 transgenic mice, etc. These bred mice are useful for further studies, including but not limited to, analysis of xenograft, anti-tumor effects, and immune cell effects.

6.8 Use of the Human CRBN Transgenic Mice in Studying Immunomodulatory Compounds Cells, cell lines, tissues, or organs derived from the human CRBN transgenic mice can be used to study compounds (e.g., immunomodulatory compounds, such as thalidomide, lenalidomide, pomalidomide, and other compounds provided in Section 5.4.2) in vitro or ex vivo. The human CRBN transgenic mice can be used to study compounds (e.g., immunomodulatory compounds, such as thalidomide, lenalidomide, pomalidomide, and other compounds provided in Section 5.4.2) in vivo. These studies include but are not limited to binding assays (e.g., CRBN binding assay, CAP binding assay), target protein degradation assays, downstream functional assays, biomarker assays, proteomics study, toxicity, pharmacokinetics, pharmacodynamics, efficacy of treating various diseases, optimizing dosing regimens, specificity of treatment, combinational therapy, mechanism of action, etc.

For example, degradation of CRBN substrate (e.g., Aiolos, Ikaros, or GSPT1) was evaluated by ex vivo compound treatment of splenocytes isolated from the human CRBN transgenic mice. Spleens from wild type (WT), heterozygous (HET), and homozygous human CRBN knock-in mice (HOM) were collected and dissociated in 5 mL PBS using gentleMACS™ Dissociator (Miltenyi Biotec, San Diego, CA). Spleen homogenates were filtered using 70 µm pre-separation filters (#130-095-823, Miltenyi Biotec) into 15-mL conical tubes and centrifuged at 1200 rpm for 5 min. After decanting, splenocytes were re-suspended in 1 mL of ACK Lysing Buffer (Gibco #A10492-01, Thermo Fisher Scientific, Waltham, MA) for 2 min. to lyse red blood cells. Ten mL of cold PBS was added to each conical tube to stop lysis, and splenocytes were again centrifuged at 1200 rpm for 5 min. After decanting, splenocytes were re-suspended in 1 mL PBS, filtered again, and pooled for each mouse phenotype to count and determine viability using Vi-Cell™ XR cell counter (Beckman Coulter, Indianapolis, IN). After counting and viability check, tubes with pooled splenocytes were centrifuged at 1200 rpm for 5 min., decanted, and resuspended in warm RPMI 1640 media supplemented with 10% FBS at a concentration of $5.5 \times 10^6$ splenocytes/mL (20-30 mL depending on number of splenocytes).

$15 \times 10^6$ WT, HET, or HOM splenocytes were plated in wells of separate 6-well plates. Compounds diluted in DMSO (final concentration 0.2%)/RPMI 1640 media were dispensed into wells at concentrations ranging from 10 µM to 1 nM. 0.2% DMSO was also dispensed in one well of each plate as a negative control. Splenocytes were treated with compounds from 4 to 24 hrs in incubators at 37° C. Compound-treated splenocytes were then collected in 15 mL conical tubes, centrifuged at 1500 rpm for 6 mins, media aspirated off, and washed once with 5 mL PBS. After washing, splenocytes were again centrifuged, PBS was aspirated off, and splenocyte pellets were flash frozen on dry ice.

Splenocyte pellets were lysed using cold 1× cell lysis buffer (#9803, Cell Signaling Technology, Danvers, MA), supplemented with cOmplete ULTRA protease inhibitor tablet (#05892920001, Roche Diagnostics Corporation, Indianapolis, IN) and phosphatase inhibitors (Pierce #78442, Thermo Fisher Scientific, Waltham, MA). Protein concentration of lysates was determined using BCA Protein Assay Kit (Pierce #A10492-01, Thermo Fisher Scientific, Waltham, MA) and western blots were run to evaluate substrate degradation resulting from ex vivo compound treatment. Twenty microgram of each splenoctye lysate was loaded onto 4-12% Criterion XT Bis Tris gels (Bio-Rad #3450124, Bio-Rad Laboratories, Hercules, CA) and run at 130 V for 1.5 hr and then transferred onto nitrocellulose membranes using Trans-Blot Turbo Transfer System (Bio-Rad Laboratories). After 1 hr of blocking in Odyssey® Blocking buffer (#927-40100, LI-COR Biotechnology, Lincoln, NE), membranes were incubated with primary antibodies for Aiolos (polyclonal goat, #sc-18683, Santa Cruz Biotechnology, Dallas, TX), Ikaros (monoclonal rabbit, #14859, Cell Signaling Technology), GSPT-1 (polyclonal rabbit, #ab49878, Abcam PLC, Cambridge, United Kingdom), GAPDH (monoclonal mouse, #AM4300, Thermo Fisher Scientific) overnight at 4° C. After washing in PBST, membranes were probed with a fluorescent secondary antibody, Alexa Fluor 680® goat anti-rabbit IgG (Invitrogen #A-21076, Thermo Fisher Scientific) or IRDye® 800CW goat anti-mouse IgG (#926-32210, LI-COR Biotechnology), for 1 hr at room temperature. Following incubation with secondary antibodies, membranes were again washed in PBST. Membranes were scanned using Odyssey® CLx Imaging System (LI-COR Biotechnology) and quantified using Image Studio™ software.

In the initial pilot experiment, ex vivo incubation with Compound B at 1 µM or 10 µM for 24 hrs resulted in significant degradation of Aiolos (FIGS. 8A and 8B) and Ikaros (FIGS. 9A and 9B) in HET and HOM splenocytes and only minimal degradation in WT splenocytes.

FIGS. 8A and 8B show that treatment of 10 µM Compound B resulted in 84% degradation in HOM splenocytes, 77% degradation in HET splenocytes, and 27% degradation in WT splenocytes, and that treatment of 1 µM Compound B resulted in 81% degradation in HOM splenocytes, 76% degradation in HET splenocytes, and 28% degradation in WT splenocytes.

FIGS. 9A and 9B show a similar trend of degradation for Ikaros following 24 hr ex vivo treatment with Compound B. At 10 µM of Compound B, 82% degradation of Ikaros was observed in HOM splenocytes, 68% degradation in HET splenocytes, and only 20% degradation in WT splenocytes. Similarly, 1 µM treatment of Compound B resulted in 76% Ikaros degradation in HOM splenocytes, 60% degradation in HET splenocytes, and 23% degradation in WT splenocytes.

A second ex vivo experiment using splenocytes from WT, HET, and HOM mice was conducted to study the dose dependency of Aiolos or Ikaros degradation in response to a range of Compound B concentrations. These doses included 1, 0.1, 0.01, and 0.001 µM of Compound B, and incubation time was reduced to 6 hr.

Following the ex vivo treatment in HOM splenocytes, 78%, 66%, 54%, and 28% degradation of Aiolos was observed at 1, 0.1, 0.01, and 0.001 µM of Compound B, respectively (FIG. 10A right panel and 10B). In HET splenocytes, 41%, 32%, 13%, and 0% degradation of Aiolos was observed at 1, 0.1, 0.01, and 0.001 µM of Compound B, respectively (FIG. 10A middle panel and 10B). In WT splenocytes, no degradation of Aiolos was observed at any concentration of Compound B in this experiment (FIG. 10A left panel and 10B).

A similar dose-dependent response was observed for Ikaros degradation in HOM and HET splenocytes. In HOM splenocytes, 59%, 55%, 41% and 14% degradation of Ikaros was observed at 1, 0.1, 0.01, and 0.001 µM of Compound B, respectively (FIG. 11A right panel and 11B). In HET splenocytes, 49%, 45%, 8% and 0% degradation of Ikaros was observed at 1, 0.1, 0.01, and 0.001 µM of Compound B, respectively (FIG. 11A middle panel and 11B). Similar to what was observed for Aiolos degradation, no degradation of Ikaros was observed in WT splenocytes at any concentration of Compound B (FIG. 11A left panel and 11B).

An additional ex vivo experiment using splenocytes from WT and HOM mice was conducted to evaluate GSPT1 degradation using Compound C and Compound E. Similar to the previous ex vivo experiments with Compound B, 15×10⁶ WT and HOM splenocytes in RPMI 1640 media supplemented with 10% FBS were plated in 6-well plates. WT and HOM splenocytes were treated with Compound C at 100 nM or 1 nM and with Compound E at 10 µM or 100 nM for 4 hr at 37° C. Splenocytes were collected and transferred into 15-mL conical tubes, centrifuged at 1500 rpm for 6 mins, media aspirated off, and washed once with 5 mL PBS. After washing, splenocytes were again centrifuged, PBS was aspirated off, and splenocyte pellets were flash frozen on dry ice. Splenocytes were lysed using lysis buffer indicated above and protein concentration was determined. Western blots using 20 µg of protein were run to determine GSPT1 degradation.

Western blot analysis showed significant degradation of GSPT1 in HOM splenocytes and only minimal degradation of GSPT1 in WT splenocytes following ex vivo treatment with Compound C. In HOM splenocytes, 65% and 89% degradation of GSPT1 was observed at 1 nM and 100 nM Compound C, respectively (FIG. 12A right panel and 12B). In contrast, only 11% and 7% degradation of GSPT1 was observed in WT splenocytes at 1 nM and 100 nM Compound C, respectively (FIG. 12A left panel and 12B).

Similarly, western blot analysis of splenocytes treated ex vivo with the other compound, Compound E, showed significant degradation of GSPT1 in HOM splenocytes, but not in WT splenocytes. At 10 µM and 100 nM of Compound E, 74% and 70% degradation of GSPT1 was observed in HOM splenocytes, respectively (FIG. 13A right panel and 13B). However in WT splenocytes, at 10 µM and 100 nM of Compound E, 6% and 0% degradation of GSPT1 was observed, respectively (FIG. 13A left panel and 13B).

These exemplary ex vivo results demonstrate that the human CRBN transgenic mice can be used, for example, in evaluating efficacy, specificity, toxicity, pharmacokinetics, pharmacodynamics, mechanism of action of certain compounds (e.g., immunomodulatory compounds, such as thalidomide, lenalidomide, pomalidomide, and other compounds provided in Section 5.4.2) in treating various diseases (such as cancer); optimizing dosing regimens of these compounds; and studying combinational therapies with other therapeutics for such diseases.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

7. SEQUENCE LISTING

The present specification is being filed with a computer readable form (CRF) copy of the Sequence Listing. The CRF entitled 12827-974-228_SEQLIST.txt, which was created on Jan. 12, 2017 and is 31,899 bytes in size, is identical to the paper copy of the Sequence Listing and is incorporated herein by reference in its entirety.

---

What is claimed is:

1. A transgenic mouse whose genome comprises a replacement of exon 2 but not exon 1 of an endogenous cereblon (CRBN) gene with an exogenous sequence consisting of cDNA encoding a human CRBN fragment having the nucleic acid sequence of SEQ ID NO: 7 and a polyadenylation sequence, wherein the mouse functionally expresses human CRBN isoforms 1 and 2.

2. The transgenic mouse of claim 1, wherein expression of human CRBN isoforms 1 and 2 is under the control of an endogenous CRBN promoter.

3. A cell isolated from the transgenic mouse of claim 1, wherein the cell functionally expresses human CRBN isoforms 1 and 2.

4. A cell line isolated from the transgenic mouse of claim 1, wherein the cell line functionally expresses human CRBN isoforms 1 and 2.

5. A tissue isolated from the transgenic mouse of claim 1, wherein the tissue functionally expresses human CRBN isoforms 1 and 2.

6. An organ isolated from the transgenic mouse of claim 1, wherein the organ functionally expresses human CRBN isoforms 1 and 2.

7. The transgenic mouse of claim 1, wherein the polyadenylation sequence is a bovine growth hormone polyadenylation sequence.

* * * * *